(12) United States Patent
Ma et al.

(10) Patent No.: US 7,981,866 B2
(45) Date of Patent: Jul. 19, 2011

(54) MG53 COMPOSITIONS AND METHODS OF USE

(75) Inventors: Jianjie Ma, Belle Mead, NJ (US); Noah Weisleder, Elizabeth, NJ (US); Chuanxi Cai, Highland Park, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 50 days.

(21) Appl. No.: 12/307,303

(22) PCT Filed: Jul. 11, 2007

(86) PCT No.: PCT/US2007/015815
§ 371 (c)(1),
(2), (4) Date: Jan. 2, 2009

(87) PCT Pub. No.: WO2008/054561
PCT Pub. Date: May 8, 2008

(65) Prior Publication Data
US 2009/0318348 A1      Dec. 24, 2009

Related U.S. Application Data

(60) Provisional application No. 60/830,013, filed on Jul. 11, 2006, provisional application No. 60/876,871, filed on Dec. 22, 2006.

(51) Int. Cl.
*A61K 38/17* (2006.01)
*A61K 38/39* (2006.01)

(52) U.S. Cl. .......... 514/19.1; 514/1.1; 514/1.2; 514/9.4; 514/21.2; 435/69.1; 435/69.7; 530/350

(58) Field of Classification Search .................. None
See application file for complete search history.

(56) References Cited

U.S. PATENT DOCUMENTS
6,943,241 B2 * 9/2005 Isogai et al. ............... 536/23.1

FOREIGN PATENT DOCUMENTS
EP        1 440 891 A2 *  7/2004

OTHER PUBLICATIONS

K.M. Short et al., "Subclassification of the RBCC/TRIM superfamily reveals a novel motif necessary for microtubule binding", Journal of Biological Chemistry 281(13):8970-8980, Mar. 31, 2006.*
*International Search Report* for PCT/US2007/015815.
*Supplementary European Search Report and Opinion* for: App. No. EP 07 86 7154.2-1212 / 2037737; PCT/US2007/015815.

* cited by examiner

*Primary Examiner* — Lorraine Spector
(74) *Attorney, Agent, or Firm* — McCarter & English, LLP

(57) ABSTRACT

Disclosed herein are nucleic acid sequences that encode novel polypeptides. Also disclosed are polypeptides encoded by these nucleic acid sequences, and antibodies, which immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of disorders involving any one of these novel human nucleic acids and proteins.

25 Claims, 22 Drawing Sheets

FIG. 1

```
                        10         20         30         40         50         60
                         |          |          |          |          |          |
Mouse          MSAAPGLLR---QELSCPLCLQLFDAPVTAECGHSFCRACLIRVAGEPAADGTVACPCCQ
Rat            MSTAPGLLR---QELSCPLCLQLFDAPVTAECGHSFCRACLIRVAGEPADDGTVACPCCQ
Human          MSAAPGLLH---QELSCPLCLQLFDAPVTAECGHSFCRACLGRVAGEPAADGTVLCPCCQ
Chimpanzee     MSAAPGLLH---QELSCPLCLQLFDAPVTAECGHSFCRACLGRVAGEPAADGTVLCPCCQ
Rhesus         MSAAPGLLH---QELSCPLCLQLFDAPVTAECGHSFCRACLGRVAGEPAADGTVLCPCCQ
Canine         MSAAPGLLH---QELSCPLCLQLFDAPVTAECGHSFCRACLSRVAGEPAADGTVPCPCCQ
Bovine         MSAAPGLLH---QELSCPLCLQLFDAPVTAECGHSFCRACLSRVAGEPAADGTVLCPSCQ
Rabbit         MSAAPGLLH---QELSCPLCLQLFDAPVTAECGHSFCRACLSRVAGEPAADGTVNCPCCQ
Opposum        MSGAPALMQGMYQDLSCPLCLKLFDAPITAECGHSFCRNCLLRLAPDPQAG-TVLCPSCQ
X. laevis      -MSTPQLMQGMQKDLTCQLCLELFRAPVTPECGHTFCQGCLTGVPKNQDQNGSTPCPTCQ
X. tropical    -MSTPQLMQGMQKDLTCPLCLELFRAPVTPECGHTFCQGCLTGAPKNQDQNGSTPCPTCQ
                 :* *::    ::*:* ***:** **:*.****:**: **   . :   . :. ** **
Prim.cons.     MSAAPGLLHGMQQELSCPLCLQLFDAPVTAECGHSFCRACLZRVAGEPAADGTVLCPCCQ
                              RING domain 70         80         90        100        110        120
                         |          |          |          |          |          |
Mouse          APTRPQALSTNLQLSRLVEGLAQVPQGHCEEHLDPLSIYCEQDRTLVCGVCASLGSHRGH
Rat            ASTRPQALSTNLQLARLVEGLAQVPQGHCEEHLDPLSIYCEQDRTLVCGVCASLGSHRGH
Human          APTRPQALSTNLQLARLVEGLAQVPQGHCEEHLDPLSIYCEQDRALVCGVCASLGSHRGH
Chimpanzee     APTRPQALSTNLQLARLVEGLAQVPQGHCEEHLDPLSIYCEQDRALVCGVCASLGSHRGH
Rhesus         APTRPQALSTNLQLARLVEGLAQVPQGHCEEHLDPLSIYCEQDRALVCGVCASLGSHRGH
Canine         ALTRPQALSTNQQLARLVEGLAQVPQGHCEEHLDPLSIYCEQDRALVCGVCASLGSHRGH
Bovine         APTRPQALSTNLQLARLVEGLAQVPQGHCEEHLDPLSIYCEQDRALVCGVCASLGSHRGH
Rabbit         APTRPQALSTNLQLARLVEGLAQVPQGHCEEHLDPLSIYCEQDRVLVCGVCASLGSHRGH
Opposum        APTKPDGLNTNQQLARLVESLAQVPQGHCEEHLDPLSVYCEQDRALICGVCASLGKHRGH
X. laevis      SPSRPETLQINRQLEHLVQSFKQVPQGHCLEHMDPLSVYCEQDKELICGVCASLGKHKGH
X. tropical    TPSRPETLQINRQLEHLVQSFKQVPKGHCLEHLDPLSVYCEQDKELICGVCASLGKHKGH
               : ::*: *. * ** :**:.: ***:*** **:****.***** *:*********.*.**
Prim.cons.     APTRPQALSTNLQLARLVEGLAQVPQGHCEEHLDPLSIYCEQDRALVCGVCASLGSHRGH
                                                B-box2

130        140        150        160        170        180
                         |          |          |          |          |          |
Mouse          RLLPAAEAQARLKTQLPQQKMQLQEACMRKEKTVAVLEHQLVEVEETVRQFRGAVGEQLG
Rat            RLLPAAEAHARLKTQLPQQKAQLQEACMRKEKSVAVLEHQLVEVEETVRQFRGAVGEQLG
Human          RLLPAAEAHARLKTQLPQQKLQLQEACMRKEKSVAVLEHQLVEVEETVRQFRGAVGEQLG
Chimpanzee     RLLPAAEAHARLKTQLPQQKLQLQEACMRKEKSVAVLEHQLVEVEETVRQFRGAVGEQLG
Rhesus         RLLPAAEAHARLKTQLPQQKLQLQEACMRKEKSVAVLEHQLVEVEETVRQFRGAVGEQLG
Canine         RLLPAAEAHARLKTQLPQQKLQLQEACMRKEKSVALLEHQLMEVEEMVRQFRGAVGEQLG
Bovine         RLLPAAEAHARLKTQLPQQKMQLQEACMRKEKSVALLEHQLLEVEETVRQFRGAVGEQLG
Rabbit         RLLPAAEAHSRLKTQLPQQKLQLQEASMRKEKSVAVLEHQLTEVEETVRQFRGAVGEQLG
Opposum        SVVTAAEAHQRMKKQLPQQRLQLQEACMRKEKTVALLDRQLAEVEETVRQFQRAVGEQLG
X. laevis      NIITASEAFAKLKRQLPQQQVILQEARLKKEKTVAVLDRQVAEVQDTVSRFKGNVKHQLN
X. tropical    NIITAAEAYAKLKRQLPQQQVILQEARLKKEKTVAVLDRQVAEVQDTVSRFKGNVKHQLN
               ::.*:**  ::.* *****: **** ::::***:**:::.*  **:: *  .:*  .**.
Prim.cons.     RLLPAAEAHARLKTQLPQQKLQLQEACMRKEKSVAVLEHQLVEVEETVRQFRGAVGEQLG
                                    Coiled-coil domain→
```

FIG. 1(CONT.)

```
                    190        200        210        220        230        240
                     |          |          |          |          |          |
Mouse         KMRMFLAALESSIDREAERVRGDAGVALRRELSSINSYLEQIRQMEKVLEEVADKPQTEF
Rat           KMRMFLAALESSIDREAERVRGEAGVALRRELSSINSYLEQIRQMEKVLEEVADKPQTEF
Human         KMRVFLAALEGSIDCEAERVRGEAGVALRRELGSINSYLEQIRQMEKVLEEVADKPQTEF
Chimpanzee    KMRVFLAALEGSIDREAERVRGEAGVALRRELGSINSYLEQIRQMEKVLEEVADKPQTEF
Rhesus        KMRVFLAALEGSIDREAERVRGEAGVALRRELGSINSYLEQIRQMEKVLEEVADKPQTEF
Canine        KMRVFLAALEGSIDREAERVRGEAGVALRRELGSINSYLEQIRQMEKVLEEVADKPQTEF
Bovine        KMRLFLAALEGSIDREAERVRGEAGVALRRELGSINSYLEQIRQMEKVLEEVADKPQTEF
Rabbit        KMRVFLAALEGSIDREAERVRSEAGVALRRELGGIHSYLEQIRQMEKVLEEVADKPQTEF
Opposum       VMRAFLAALESSIGKEAERVTGEAGTALKAERRITSYLDQIQQMEKVLDEVTDQPQTEF
X. laevis     AMRSYLNIMEASLGKEADKAESAATEALLVERKTMGHYLDQLRQMEGVLKDVEGQEQTEF
X. tropical   AMRSYLSIMEASLSKEADNAEHTATEALLVERKTMGHYLDQLRQMDGVLKDVESQEQTEF
                **  :*   :*.**. **:..    *  **  *   :  **:**:**: **.:*  .:  ****
Prim.cons.    KMRVFLAALEGSIDREAERVRGEAGVALRRELGSINSYLEQLRQMEKVLEEVADKPQTEF 250        260        270        280        290        300
                     |          |          |          |          |          |
Mouse         LMKFCLVTSRLQKILSESPPPARLDIQLPVISDDFKFQVWKKMFRALMPALEELTFDPSS
Rat           LMKFCLVTSRLQKILSESPPPARLDIQLPVISDDFKFQVWKKMFRALMPELEELTFDPSS
Human         LMKYCLVTSRLQKILAESPPPARLDIQLPIISDDFKFQVWRKMFRALMPALEELTFDPSS
Chimpanzee    LMKYCLVTSRLQKILAESPPPARLDIQLPIISDDFKFQVWRKMFRALMPALEELTFDPSS
Rhesus        LMKYCLVTSRLQKILAESPPPARLDIQLPIISDDFKFQVWRKMFRALMPALEELTFDPSS
Canine        LMKYCLVTSRLQKILAESPPPARLDIQLPVISDDFKFQVWRKMFRALMPVTKELTFDPSS
Bovine        LMKYCLVTSRLQKILAESPPPARLDIQLPIISDDFKFQVWRKMFRALMPARQELTFDPST
Rabbit        LMKYCLVTSRLQKILAESPPPARLDIQLPIISDDFKFQVWRKMFRALMPALEELTFDPSS
Opposum       LRKYCLVISRLQKILAESPPAARLDIQLPIISDDFKFQVWRKMFRALMPGMEVLTFDPAS
X. laevis     LRKYCVVAARLNKILSESPPPGRLDIQLPIISDEFKFQVWRKMFRALMPALENMTFDPDT
X. tropical   LRKYCVVAARLNKILAESPPPGRLDIQLPIISDEFKFQVWRKMFRALMPALENLTFDPDT
              * *:*:*  :**:***:****..*******:***:****** ******    :  :****  :
Prim.cons.    LMKYCLVTSRLQKILAESPPPARLDIQLPIISDDFKFQVWRKMFRALMPALEELTFDPSS 310        320        330        340        350        360
                     |          |          |          |          |          |
Mouse         AHPSLVVSSSGRRVECSDQKAPPAGEDTRQFDKAVAVVAQQLLSQGEHYWEVEVGDKPRW
Rat           AHPSLVVSASGRRVECSEQKAPPAGEDTCQFDKTVAVVAKQLLSQGEHYWEVEVGDKPRW
Human         AHPSLVVSSSGRRVECSEQKAPPAGEDPRQFDKAVAVVAHQQLSEGEHYWEVDVGDKPRW
Chimpanzee    AHPSLVVSSSGRRVECSEQKAPPAGEDPRQFDKAVAVVAHQQLSEGEHYWEVDVGDKPRW
Rhesus        AHPSLVVSSSGRRVECSEQKAPPAGEDPRQFDKAVAVVAHQQLSEGEHYWEVEVGDKPRW
Canine        AHPSLVLSPSGRRVECSDQKAPPAGEDPCQFDKAVAVVAQQVLSDGEHYWEVQVGEKPRW
Bovine        AHPSLVLSNSGRCVECSEQKAPPAGEDPRQFDKAVAVVTHQLLSEGEHYWEVEVGDKPRW
Rabbit        AHPSLVVSPTGRRVECSEQKAPPAGDDARQFDKAVAVVAQQLLSDGEHYWEVEVGDKPRW
Opposum       AHPSLLVSPSGRRVECVEQKAPPAGDDPQQFDKAVALVAKQQLSEGEHYWEVEVGDKPRW
X. laevis     AQQYLVVSSEGKSVECADQKQS-VSDEPNRFDKSNCLVSKQSFTEGEHYWEVIVEDKPRW
X. tropical   AQQNLVVFSDGKSVECSEQKQS-VSDEPNRFDKSNCLVSKESFTEGEHYWEVLVEDKPRW
              *:  *::    *: *** :**   ...::.:****  :.*:::  ::::*******  *  .****
Prim.cons.    AHPSLVVSSSGRRVECSEQKAPPAGEDPRQFDKAVAVVAQQLSEGEHYWEVEVGDKPRW
                                                              ←PRY domain
```

FIG. 1(CONT.)

```
                     370        380        390        400        410        420
                      |          |          |          |          |          |
Mouse        ALGVMAADASRRGRLHAVPSQGLWLLGLRDGKILEAHVEAKEPRALRTPERPPARIGLYL
Rat          ALGVMAADASRRGRLHAVPSQGLWLLGLRDGKILEAHVEAKEPRALRTPERPPARIGLYL
Human        ALGVIAAEAPRRGRLHAVPSQGLWLLGLREGKILEAHVEAKEPRALRSPERRPTRIGLYL
Chimpanzee   ALGVIAAEAPRRGRLHAVPSQGLWLLGLREGKILEAHVEAKEPRALRSPERRPTRIGLYL
Rhesus       ALGVIAAEGPRRGRLHAVPSQGLWLLGLREGKILEAHVEAKEPRALRSPERRPTRIGLYL
Canine       ALGVIAAQASRRGRLHAVPSQGLWLLGLRDGKILEAHVEAKEPRALRTPERRPTRIGIYL
Bovine       ALGVIGAQAGRRGRLHAVPSQGLWLLGLRDGKILEAHVEAKEPRALRTPERRPTRIGIYL
Rabbit       ALGVMASEASRRGRLHAVPSQGLWLLGLRDGKTLEAHVEAKEPRALRTPERRPTRLGLYL
Opposum      GLGLISADVSRRGKLHPTPSQGFWMLGLREGKVYEAHVESKEPKVLKVDGR-PSRIGLYL
X. laevis    ALGIISETANRKGKLHATPSNGFWIIGCKEGKVYEAHTEQKEPRVLRVEGR-PEKIGVYL
X. tropical  ALGVISETANRKGKLHASPSNGFWLIGCKEGKVYEAHTEQKEPRVLRVEGR-PEKIGIYL
              .**::.     *:*:**. **:*:::* ::**  ***.* ***:.*:    * * ::*:**
Prim.cons.   ALGVIAAEASRRGRLHAVPSQGLWLLGLREGKILEAHVEAKEPRALRTPERRPTRIGLYL
                                    < SPRY domain >

430        440        450        460        470        480
                      |          |          |          |          |          |
Mouse        SFADGVLAFYDASNPDVLTPIFSFHERLPGPVYPIFDVCWHDKGKNAQPLLLVGPE-----QEQA
(Seq Id No 3)
Rat          SFADGVLTFYDASNTDALTPLFSFHERLPGPVYPMFDVCWHDKGKNSQPLLLVGPD-----SEQA
(Seq Id No 14)
Human        SFGDGVLSFYDASDADALVPLFAFHERLPRPVYPFFDVCWHDKGKNAQPLLLVGPE-----GAEA
(Seq Id No 1)
Chimpanzee   SFGDGVLSFYDASDADALVPLFAFHERLPRPVYPFFDVCWHDKGKNAQPLLLVGPE-----GAEA
(Seq Id No 11)
Rhesus       SFGDGVLSFYDASDADALVPLFAFHERLPGPVYPFFDVCWHDKGKNSQPLLLVGSE-----GAEA
(Seq Id No 12)
Canine       SFGDGVLSFYDASDPDALELLFAFHERLPGPVYPFFDVCWHDKGKNAQPLLLVGPD-----GEEA
(Seq Id No 10)
Bovine       SFGDGVLSFYDASDPDALELLFAFHERLPGPVYPFFDVCWHDKGKNAQPLLLVGPEVSGGSGSEA
(Seq Id No 13)
Rabbit       SFGDGVLAFYDASDADALELLFAFRERLPGPVYPFFDVCWHDKGKNAQPLLLVGPD-----GQEA
(Seq Id No 5)
Opposum      SFRDGVLSFYDASDLDNLLPLYAFHERLPGPVYPFFDVCWHDKGKNAQPLLLLGPD-----GEQ-
(Seq Id No 9)
X. laevis    SFSDGVVSFFDSSDEDNLKLLYTFNERFSGRLHPFFDVCWHDKGKNSQPLKIFYPP-----AEQL
(Seq Id No 15)
X. tropical  SFSDGVVSFFDSSDEDNIKLLYTFNERFSGRLHPFFDVCWHDKGKNAQPLKIFYPP-----AEQL
(Seq Id No 16)
              ** ***:.*:*:*: *  :   :::*.**:.  ::*:*************.*** :. .
Prim.cons.   SFGDGVLSFYDASDADAL2PLFAFHERLPGPVYPFFDVCWHDKGKNAQPLLLVGPEVSGGSGEEA
```

FIG. 10
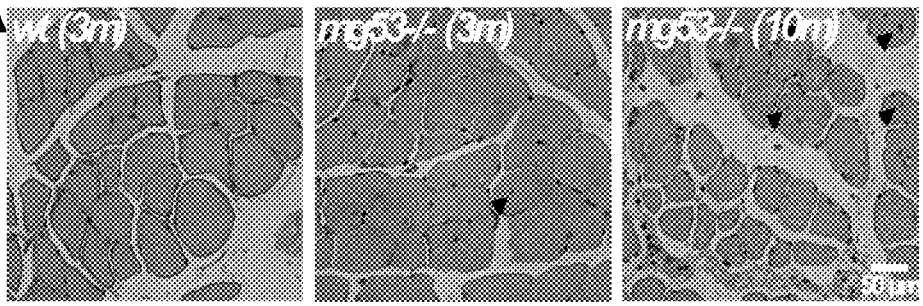
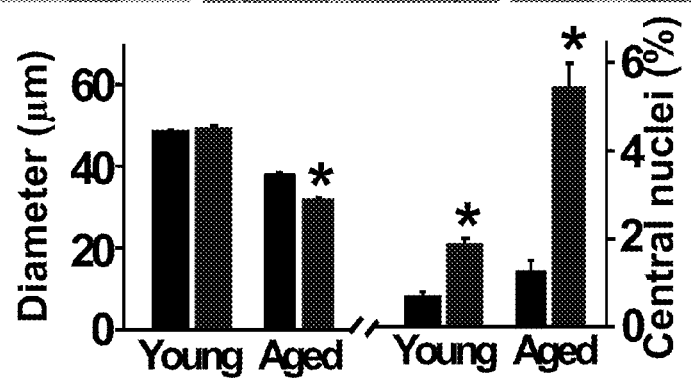
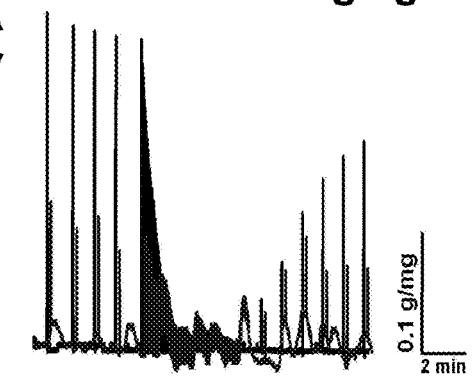
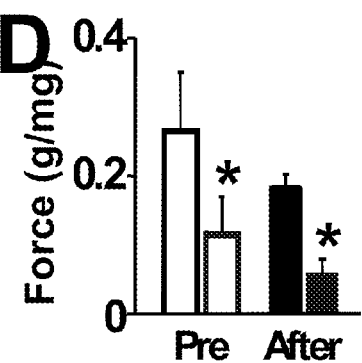
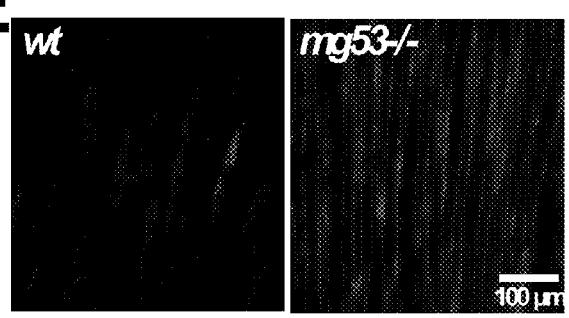
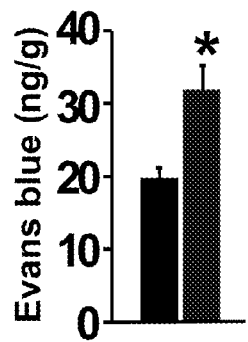

FIG. 13
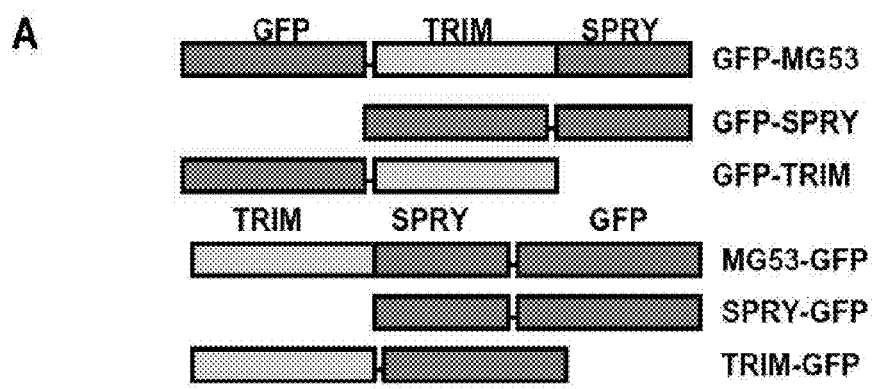
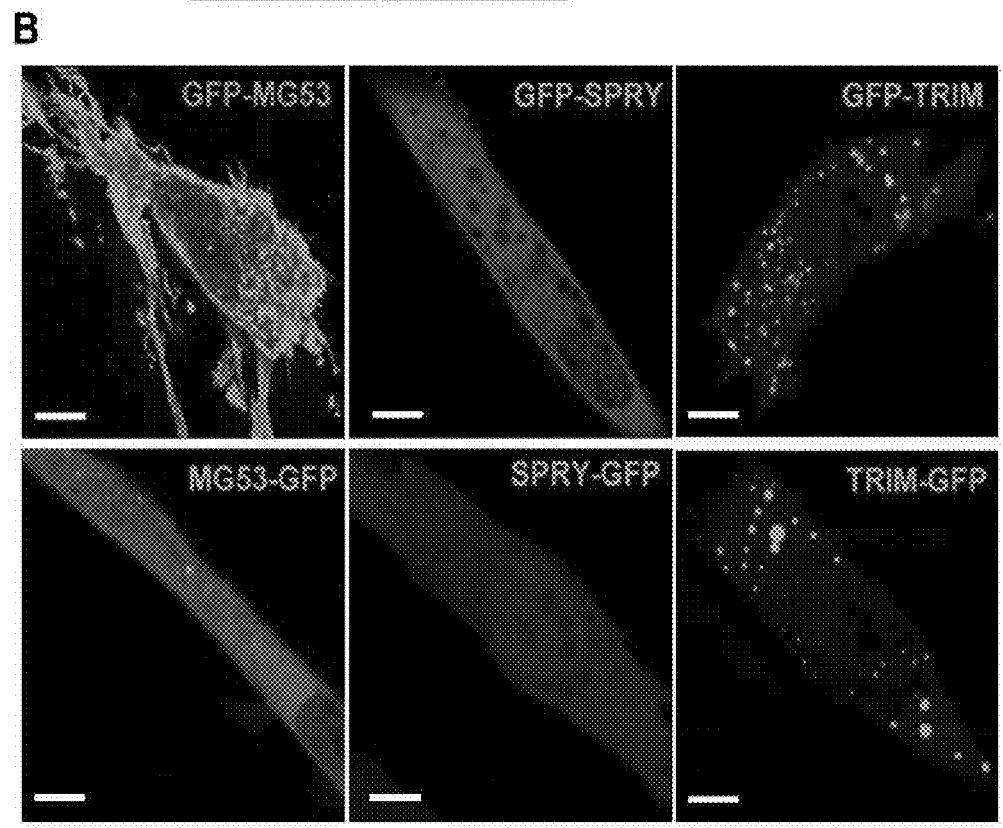
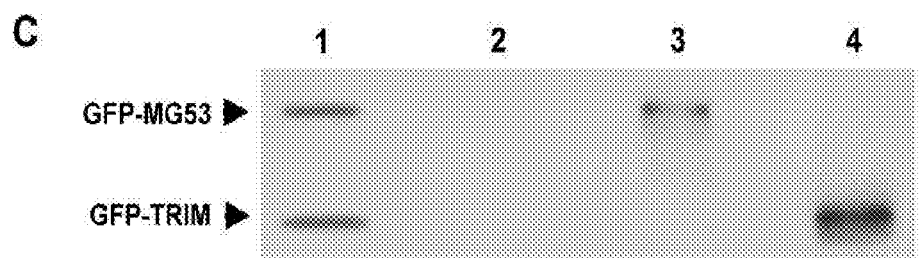

SEQUENCE LISTING

```
<160> NUMBER OF SEQ ID NOS: 25

<210> SEQ ID NO 1
<211> LENGTH: 477
<212> TYPE: PRT
<213> ORGANISM: Homo sapiens
<220> FEATURE:
<221> NAME/KEY: misc_feature
<222> LOCATION: (1)..(477)
<223> OTHER INFORMATION: Human MG53 Polypeptide

<400> SEQUENCE: 1

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30
```

-continued

```
Phe Cys Arg Ala Cys Leu Gly Arg Val Ala Gly Glu Pro Ala Ala Asp
             35                  40                  45

Gly Thr Val Leu Cys Pro Cys Cys Gln Ala Pro Thr Arg Pro Gln Ala
 50                  55                  60

Leu Ser Thr Asn Leu Gln Leu Ala Arg Leu Val Glu Gly Leu Ala Gln
 65                  70                  75                  80

Val Pro Gln Gly His Cys Glu His Leu Asp Pro Leu Ser Ile Tyr
                 85                  90                  95

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
            115                 120                 125

Leu Lys Thr Gln Leu Pro Gln Gln Lys Leu Gln Leu Gln Glu Ala Cys
130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Cys
            180                 185                 190

Glu Ala Glu Arg Val Arg Gly Glu Ala Gly Val Ala Leu Arg Arg Glu
            195                 200                 205

Leu Gly Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
            275                 280                 285

Glu Glu Leu Thr Phe Asp Pro Ser Ser Ala His Pro Ser Leu Val Val
290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
            355                 360                 365

Arg Gly Arg Leu His Ala Val Pro Ser Gln Gly Leu Trp Leu Leu Gly
370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Arg Pro
            435                 440                 445

Val Tyr Pro Phe Phe Asp Val Cys Trp His Asp Lys Gly Lys Asn Ala
450                 455                 460
```

Gln Pro Leu Leu Leu Val Gly Pro Glu Gly Ala Glu Ala
465                 470                 475

<210> SEQ ID NO 2
<211> LENGTH: 1434
<212> TYPE: DNA
<213> ORGANISM: Homo sapiens
<220> FEATURE:
<221> NAME/KEY: misc_feature
<222> LOCATION: (1)..(1434)
<223> OTHER INFORMATION: Human MG53 cDNA

<400> SEQUENCE: 2

| | | | | | |
|---|---|---|---|---|---|
| atgtcggctg | cgcccggcct | cctgcaccag | gagctgtcct | gcccgctgtg | cctgcagctg | 60 |
| ttcgacgcgc | ccgtgacagc | cgagtgcggc | cacagtttct | gccgcgcctg | cctaggccgc | 120 |
| gtggccgggg | agccggcggc | ggatggcacc | gttctctgcc | cctgctgcca | ggcccccacg | 180 |
| cggccgcagg | cactcagcac | caacctgcag | ctggcgcgcc | tggtggaggg | gctggcccag | 240 |
| gtgccgcagg | gccactgcga | ggagcacctg | gacccgctga | gcatctactg | cgagcaggac | 300 |
| cgcgcgctgt | tgtgcggagt | gtgcgcctca | ctcggctcgc | accgcggtca | tcgcctcctg | 360 |
| cctgccgccg | aggcccacgc | acgcctcaag | acacagctgc | acagcagaa | actgcagctg | 420 |
| caggaggcat | gcatgcgtaa | ggagaagagt | gtggctgtgc | tggagcatca | gctggtggag | 480 |
| gtggaggaga | cagtgcgtca | gttccggggg | gccgtggggg | agcagctggg | caagatgcgg | 540 |
| gtgttcctgg | ctgcactgga | gggctccttg | gactgcgagg | cagagcgtgt | acggggtgag | 600 |
| gcaggggtcg | ccttgcgccg | ggagctgggg | agcctgaact | cttacctgga | gcagctgcgg | 660 |
| cagatggaga | aggtcctgga | ggaggtggcg | gacaagccgc | agactgagtt | cctcatgaaa | 720 |
| tactgcctgg | tgaccagcag | gctgcagaag | atcctggcag | agtctccccc | acccgcccgt | 780 |
| ctggacatcc | agctgccaat | tatctcagat | gacttcaaat | tccaggtgtg | gaggaagatg | 840 |
| ttccgggctc | tgatgccagc | gctggaggag | ctgacctttg | acccgagctc | tgcgcacccg | 900 |
| agcctggtgg | tgtcttcctc | tggccgccgc | gtggagtgct | cggagcagaa | ggcgccgccg | 960 |
| gccggggagg | acccgcgcca | gttcgacaag | gcggtggcgg | tggtggcgca | ccagcagctc | 1020 |
| tccgagggcg | agcactactg | ggaggtggat | gttggcgaca | gccgcgctg | ggcgctgggc | 1080 |
| gtgatcgcgc | ccgaggcccc | ccgccgcggg | cgcctgcacg | cggtgccctc | gcagggcctg | 1140 |
| tggctgctgg | ggctgcgcga | gggcaagatc | ctggaggcac | acgtggaggc | caaggagccg | 1200 |
| cgcgctctgc | gcagccccga | gaggcggccc | acgcgcattg | cctttacct | gagcttcggc | 1260 |
| gacggcgtcc | tctccttcta | cgatgccagc | gacgccgacg | cgctcgtgcc | gcttttgcc | 1320 |
| ttccacgagc | gcctgcccag | gcccgtgtac | cccttcttcg | acgtgtgctg | gcacgacaag | 1380 |
| ggcaagaatg | cccagccgct | gctgctcgtg | ggtcccgaag | gcgccgaggc | ctga | 1434 |

<210> SEQ ID NO 3
<211> LENGTH: 477
<212> TYPE: PRT
<213> ORGANISM: Mus musculus
<220> FEATURE:
<221> NAME/KEY: misc_feature
<222> LOCATION: (1)..(477)
<223> OTHER INFORMATION: Mouse MG53

<400> SEQUENCE: 3

Met Ser Ala Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser

```
                    20                  25                  30
Phe Cys Arg Ala Cys Leu Ile Arg Val Ala Gly Glu Pro Ala Ala Asp
                35                  40                  45
Gly Thr Val Ala Cys Pro Cys Gln Ala Pro Thr Arg Pro Gln Ala
     50                  55                  60
Leu Ser Thr Asn Leu Gln Leu Ser Arg Leu Val Glu Gly Leu Ala Gln
 65                  70                  75                  80
Val Pro Gln Gly His Cys Glu His Leu Asp Pro Leu Ser Ile Tyr
                 85                  90                  95
Cys Glu Gln Asp Arg Thr Leu Val Cys Gly Val Cys Ala Ser Leu Gly
                100                 105                 110
Ser His Arg Gly His Arg Leu Leu Pro Ala Ala Glu Ala Gln Ala Arg
                115                 120                 125
Leu Lys Thr Gln Leu Pro Gln Gln Lys Met Gln Leu Gln Glu Ala Cys
    130                 135                 140
Met Arg Lys Glu Lys Thr Val Ala Val Leu Glu His Gln Leu Val Glu
145                 150                 155                 160
Val Glu Glu Thr Val Arg Gln Phe Arg Gly Ala Val Gly Glu Gln Leu
                165                 170                 175
Gly Lys Met Arg Met Phe Leu Ala Ala Leu Glu Ser Ser Leu Asp Arg
                180                 185                 190
Glu Ala Glu Arg Val Arg Gly Asp Ala Gly Val Ala Leu Arg Arg Glu
                195                 200                 205
Leu Ser Ser Leu Asn Ser Tyr Leu Glu Gln Leu Arg Gln Met Glu Lys
    210                 215                 220
Val Leu Glu Glu Val Ala Asp Lys Pro Gln Thr Glu Phe Leu Met Lys
225                 230                 235                 240
Phe Cys Leu Val Thr Ser Arg Leu Gln Lys Ile Leu Ser Glu Ser Pro
                245                 250                 255
Pro Pro Ala Arg Leu Asp Ile Gln Leu Pro Val Ile Ser Asp Asp Phe
                260                 265                 270
Lys Phe Gln Val Trp Lys Lys Met Phe Arg Ala Leu Met Pro Ala Leu
                275                 280                 285
Glu Glu Leu Thr Phe Asp Pro Ser Ala His Pro Ser Leu Val Val
    290                 295                 300
Ser Ser Ser Gly Arg Arg Val Glu Cys Ser Asp Gln Lys Ala Pro Pro
305                 310                 315                 320
Ala Gly Glu Asp Thr Arg Gln Phe Asp Lys Ala Val Ala Val Ala
                325                 330                 335
Gln Gln Leu Leu Ser Gln Gly Glu His Tyr Trp Glu Val Glu Val Gly
                340                 345                 350
Asp Lys Pro Arg Trp Ala Leu Gly Val Met Ala Ala Asp Ala Ser Arg
    355                 360                 365
Arg Gly Arg Leu His Ala Val Pro Ser Gln Gly Leu Trp Leu Leu Gly
    370                 375                 380
Leu Arg Asp Gly Lys Ile Leu Glu Ala His Val Glu Ala Lys Glu Pro
385                 390                 395                 400
Arg Ala Leu Arg Thr Pro Glu Arg Pro Pro Ala Arg Ile Gly Leu Tyr
                405                 410                 415
Leu Ser Phe Ala Asp Gly Val Leu Ala Phe Tyr Asp Ala Ser Asn Pro
                420                 425                 430
Asp Val Leu Thr Pro Ile Phe Ser Phe His Glu Arg Leu Pro Gly Pro
                435                 440                 445
```

Val Tyr Pro Ile Phe Asp Val Cys Trp His Asp Lys Gly Lys Asn Ala
            450                 455                 460

Gln Pro Leu Leu Leu Val Gly Pro Glu Gln Glu Gln Ala
465                 470                 475

<210> SEQ ID NO 4
<211> LENGTH: 1434
<212> TYPE: DNA
<213> ORGANISM: Mus musculus
<220> FEATURE:
<221> NAME/KEY: misc_feature
<222> LOCATION: (1)..(1434)
<223> OTHER INFORMATION: Mouse MG53 cDNA

<400> SEQUENCE: 4

```
atgtcggctg cacccggcct tctgcgtcag gaactgtcct gcccactgtg cttgcagctg      60
ttcgatgcgc cagtgacggc tgagtgtggc cacagtttct gccgtgcctg cctgatccgg     120
gtggcagggg agcctgctgc ggacggcaca gttgcctgtc cctgttgtca ggcacctaca     180
cggccgcagg ctctaagcac taacctccag ttgtcacgcc ttgtggaggg tttggcgcaa     240 gtgcccaag gccactgcga ggaacacctg gatccactga gcatctactg cgagcaggac     300
cgcacacttg tgtgtggtgt gtgtgcctcg ctcggttctc accgtggtca tcgtctcctg     360
cctgccgcta agcccaagc acgcctcaag acacagcttc cacagcagaa gatgcagctg     420
caggaggcat gcatgcgcaa ggagaagact gtagcggtgc tggagcatca gctggtggag     480
gtggaggaga cagtgcgcca gttccgggga gctgtcgggg agcagctggg gaagatgcgg     540
atgttcctgg ctgccctaga aagttctctg gaccgtgaag cagaaagggt tcggggtgat     600
gctggggttg ccttgcgtcg ggagctgtca agcctgaact cttacctaga gcaactgagg     660
cagatggaga aggtgctgga ggaggtggct gacaagccac agacagaatt cctcatgaaa     720
ttctgcctgg taaccagcag gctgcagaag atcctgtcag agtcaccacc accggcaagg     780
ctagatatcc agctgcctgt catctcagat gacttcaaat tccaggtgtg gaagaagatg     840
ttccgggctc tgatgccagc gctggaggaa ctgacttttg accccagctc tgcgcacccg     900
agcctggtgg tgtcctcctc tggtcgccga gtggagtgct cagaccagaa ggcgccgcca     960
gcgggagaag acacgcgtca gttcgacaag gcagtagcgg tggtggcgca gcagctgctg    1020
tcacagggcg agcactattg ggaggtggag gtgggcgaca aaccacgctg ggccctggga    1080
gtgatggcgg ctgacgcttc ccgccgtggc cggctgcacg cggtgccctc acagggctg    1140 tggctgctgg gtctgcgcga tgcaagatc ctggaggcgc acgtggaggc caaggagccg    1200
cgggcactgc gcacccagag gaggcctccg gcgcgcattg gcctctacct aagcttcgca    1260
gatggcgtcc tggcttttcta tgatgcgagc aaccccgacg tacttacgcc aatcttttct    1320
ttccacgagc gtctgcccgg gccggtgtac cccatctttg acgtgtgctg gcacgacaag    1380
ggcaagaatg cccagcccct gctgcttgtg gggccggagc aggaacaggc ctga          1434
```

<210> SEQ ID NO 5
<211> LENGTH: 477
<212> TYPE: PRT
<213> ORGANISM: Oryctolagus cuniculus
<220> FEATURE:
<221> NAME/KEY: misc_feature
<222> LOCATION: (1)..(477)
<223> OTHER INFORMATION: Rabbit MG53

<400> SEQUENCE: 5

Met Ser Ala Ala Pro Gly Leu Leu His Gln Glu Leu Ser Cys Pro Leu
1               5                   10                  15

```
Cys Leu Gln Leu Phe Asp Ala Pro Val Thr Ala Glu Cys Gly His Ser
                20                  25                  30

Phe Cys Arg Ala Cys Leu Ser Arg Val Ala Gly Glu Pro Ala Ala Asp
            35                  40                  45

Gly Thr Val Asn Cys Pro Cys Gln Ala Pro Thr Arg Pro Gln Ala
        50                  55                  60

Leu Ser Thr Asn Leu Gln Leu Ala Arg Leu Val Glu Gly Leu Ala Gln
 65                  70                  75                  80

Val Pro Gln Gly His Cys Glu His Leu Asp Pro Leu Ser Ile Tyr
                85                  90                  95

Cys Glu Gln Asp Arg Val Leu Val Cys Gly Val Cys Ala Ser Leu Gly
                100                 105                 110

Ser His Arg Gly His Arg Leu Leu Pro Ala Ala Glu Ala His Ser Arg
            115                 120                 125

Leu Lys Thr Gln Leu Pro Gln Gln Lys Leu Gln Leu Gln Glu Ala Ser
        130                 135                 140

Met Arg Lys Glu Lys Ser Val Ala Val Leu Glu His Gln Leu Thr Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Ser Glu Ala Gly Val Ala Leu Arg Arg Glu
        195                 200                 205

Leu Gly Gly Leu His Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
290                 295                 300

Ser Pro Thr Gly Arg Arg Val Glu Cys Ser Glu Gln Lys Ala Pro Pro
305                 310                 315                 320

Ala Gly Asp Asp Ala Arg Gln Phe Asp Lys Ala Val Ala Val Val Ala
                325                 330                 335

Gln Gln Leu Leu Ser Asp Gly Glu His Tyr Trp Glu Val Glu Val Gly
            340                 345                 350

Asp Lys Pro Arg Trp Ala Leu Gly Val Met Ala Ser Glu Ala Ser Arg
        355                 360                 365

Arg Gly Arg Leu His Ala Val Pro Ser Gln Gly Leu Trp Leu Leu Gly
370                 375                 380

Leu Arg Asp Gly Lys Thr Leu Glu Ala His Val Glu Ala Lys Glu Pro
385                 390                 395                 400

Arg Ala Leu Arg Thr Pro Glu Arg Pro Thr Arg Leu Gly Leu Tyr
                405                 410                 415

Leu Ser Phe Gly Asp Gly Val Leu Ala Phe Tyr Asp Ala Ser Asp Ala
            420                 425                 430

Asp Ala Leu Glu Leu Leu Phe Ala Phe Arg Glu Arg Leu Pro Gly Pro
```

435                 440                 445
Val Tyr Pro Phe Phe Asp Val Cys Trp His Asp Lys Gly Lys Asn Ala
            450                 455                 460

Gln Pro Leu Leu Leu Val Gly Pro Asp Gly Gln Glu Ala
465                 470                 475

<210> SEQ ID NO 6
<211> LENGTH: 1434
<212> TYPE: DNA
<213> ORGANISM: Oryctolagus cuniculus
<220> FEATURE:
<221> NAME/KEY: misc_feature
<222> LOCATION: (1)..(1434)
<223> OTHER INFORMATION: Rabbit MG53 cDNA

<400> SEQUENCE: 6

```
atgtcggccg cgcccggcct cctgcaccag gagctgtctt gcccgctgtg cctgcagctg      60
ttcgacgcgc ccgtgacagc cgagtgcggc cacagtttct gccgcgcctg cctgagccgc     120
gtggcggggg agccggcggc cgatggcacc gtgaactgcc cgtgctgcca ggcgcccacg     180
cggccgcagg cgctcagcac caacctgcag ctggcgcgcc tggtggaggg gctggcgcag     240
gtgccgcagg gccactgcga ggagcacctg gacccgctga gcatctactg cgagcaggac     300
cgcgttctcg tgtgcggcgt gtgcgcctcg ctcggctcgc accgcggcca ccgcctgctg     360
cccgccgccg aggcccactc gcgtctcaag acgcagctgc cccagcagaa gctgcagctg     420
caggaggcga gcatgcgcaa ggagaagagc gtggccgtgc tggagcacca gctcacggag     480
gtggaggaga cagtgcgtca gttccggggg gcagtggggg agcagctggg caagatgcgg     540
gtgttcctgg ccgccctgga gggctccctg gaccgcgagg cagaacgtgt gcggagcgag     600
gcgggggtgg ccttgcggcg ggagctgggg gcctccact cgtacctgga gcagctgcgg     660
cagatgcaga aggtgttgga ggaggtggct gacaagccac agaccgagtt ccttatgaaa     720
tattgcctgg tgaccagcag gctgcagaag atcctggcgg agtcgccacc acctgctcgt     780
ctggacatcc agctgccat catttcagat gacttcaaat tccaggtgtg gaggaagatg     840
ttccgggctc tgatgccagc gctggaggag ctgaccttg acccgagctc cgcgcacccg     900
agcctcgtgg tgtcacccac gggccgccga gtggagtgct cggagcagaa ggcgccgccc     960
gccggggacg acgcgcgcca gttcgacaag gctgtggccg tggtggcgca gcagctgctg    1020
tccgacggcg agcactactg ggaggtggag gtgggcgaca gccgcgctg ggcgctgggc    1080
gtgatggcct ccgaggcgag ccgccgtggc cggctgcacg ccgtgccctc acagggtttg    1140
tggctgctgg ggctgcgcga cggcaagacc ctggaggcgc acgtggaggc caaggagccg    1200
cgcgcgctgc gcaccccgga gcggcggccc acgcgcctcg gcctctacct cagcttcggc    1260
gatggcgtgc tcgccttcta cgacgccagc gacgccgacg cgctcgagct gctgtttgct    1320
ttccgcgagc gcctgcccgg gccgtgtac cccttcttcg acgtgtgctg gcatgacaag    1380
ggcaagaatg cgcagccgct gctgctcgtg gggccggatg gccaggaggc ctga         1434
```

<210> SEQ ID NO 7
<211> LENGTH: 477
<212> TYPE: PRT
<213> ORGANISM: Homo sapiens
<220> FEATURE:
<221> NAME/KEY: MUTAGEN
<222> LOCATION: (29)..(29)
<223> OTHER INFORMATION: C29L/C242A
<220> FEATURE:
<221> NAME/KEY: MUTAGEN
<222> LOCATION: (242)..(242)

<223> OTHER INFORMATION: C29L/C242A

<400> SEQUENCE: 7

```
Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Leu Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Cys
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Ala Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Gln Lys Ala Pro Pro
305                 310                 315                 320

Ala Gly Glu Asp Pro Arg Gln Phe Asp Lys Ala Val Ala Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
        355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
```

-continued

```
                    405                 410                 415
Leu Ser Phe Gly Asp Gly Val Leu Ser Phe Tyr Asp Ala Ser Asp Ala
                420                 425                 430

Asp Ala Leu Val Pro Leu Phe Ala Phe His Glu Arg Leu Pro Arg Pro
            435                 440                 445

Val Tyr Pro Phe Phe Asp Val Cys Trp His Asp Lys Gly Lys Asn Ala
        450                 455                 460

Gln Pro Leu Leu Leu Val Gly Pro Glu Gly Ala Glu Ala
465                 470                 475

<210> SEQ ID NO 8
<211> LENGTH: 151
<212> TYPE: PRT
<213> ORGANISM: Homo sapiens
<220> FEATURE:
<221> NAME/KEY: misc_feature
<222> LOCATION: (1)..(151)
<223> OTHER INFORMATION: P56539 CAV3_HUMAN CAVEOLIN-3 - HOMO SAPIENS
      (HUMAN).

<400> SEQUENCE: 8

Met Met Ala Glu Glu His Thr Asp Leu Glu Ala Gln Ile Val Lys Asp
1               5                   10                  15

Ile His Cys Lys Glu Ile Asp Leu Val Asn Arg Asp Pro Lys Asn Ile
            20                  25                  30

Asn Glu Asp Ile Val Lys Val Asp Phe Glu Asp Val Ile Ala Glu Pro
        35                  40                  45

Val Gly Thr Tyr Ser Phe Asp Gly Val Trp Lys Val Ser Tyr Thr Thr
    50                  55                  60

Phe Thr Val Ser Lys Tyr Trp Cys Tyr Arg Leu Leu Ser Thr Leu Leu
65                  70                  75                  80

Gly Val Pro Leu Ala Leu Leu Trp Gly Phe Leu Phe Ala Cys Ile Ser
                85                  90                  95

Phe Cys His Ile Trp Ala Val Val Pro Cys Ile Lys Ser Tyr Leu Ile
            100                 105                 110

Glu Ile Gln Cys Ile Ser His Ile Tyr Ser Leu Cys Ile Arg Thr Phe
        115                 120                 125

Cys Asn Pro Leu Phe Ala Ala Leu Gly Gln Val Cys Ser Ser Ile Lys
    130                 135                 140

Val Val Leu Arg Lys Glu Val
145                 150

<210> SEQ ID NO 9
<211> LENGTH: 477
<212> TYPE: PRT
<213> ORGANISM: Didelphis sp.
<220> FEATURE:
<221> NAME/KEY: PEPTIDE
<222> LOCATION: (1)..(477)
<223> OTHER INFORMATION: Opossum MG53

<400> SEQUENCE: 9

Met Ser Gly Ala Pro Ala Leu Met Gln Gly Met Tyr Gln Asp Leu Ser
1               5                   10                  15

Cys Pro Leu Cys Leu Lys Leu Phe Asp Ala Pro Ile Thr Ala Glu Cys
            20                  25                  30

Gly His Ser Phe Cys Arg Asn Cys Leu Leu Arg Leu Ala Pro Asp Pro
        35                  40                  45

Gln Ala Gly Thr Val Leu Cys Pro Ser Cys Gln Ala Pro Thr Lys Pro
    50                  55                  60
```

```
Asp Gly Leu Asn Thr Asn Gln Gln Leu Ala Arg Leu Val Glu Ser Leu
 65                  70                  75                  80

Ala Gln Val Pro Gln Gly His Cys Glu Glu His Leu Asp Pro Leu Ser
                 85                  90                  95

Val Tyr Cys Glu Gln Asp Arg Ala Leu Ile Cys Gly Val Cys Ala Ser
            100                 105                 110

Leu Gly Lys His Arg Gly His Ser Val Val Thr Ala Ala Glu Ala His
        115                 120                 125

Gln Arg Met Lys Lys Gln Leu Pro Gln Gln Arg Leu Gln Leu Gln Glu
    130                 135                 140

Ala Cys Met Arg Lys Glu Lys Thr Val Ala Leu Leu Asp Arg Gln Leu
145                 150                 155                 160

Ala Glu Val Glu Glu Thr Val Arg Gln Phe Gln Arg Ala Val Gly Glu
                165                 170                 175

Gln Leu Gly Val Met Arg Ala Phe Leu Ala Ala Leu Glu Ser Ser Leu
            180                 185                 190

Gly Lys Glu Ala Glu Arg Val Thr Gly Glu Ala Gly Thr Ala Leu Lys
        195                 200                 205

Ala Glu Arg Arg Ile Val Thr Ser Tyr Leu Asp Gln Leu Gln Gln Met
    210                 215                 220

Glu Lys Val Leu Asp Glu Val Thr Asp Gln Pro Gln Thr Glu Phe Leu
225                 230                 235                 240

Arg Lys Tyr Cys Leu Val Ile Ser Arg Leu Gln Lys Ile Leu Ala Glu
                245                 250                 255

Ser Pro Pro Ala Ala Arg Leu Asp Ile Gln Leu Pro Ile Ile Ser Asp
            260                 265                 270

Asp Phe Lys Phe Gln Val Trp Arg Lys Met Phe Arg Ala Leu Met Pro
        275                 280                 285

Gly Met Glu Val Leu Thr Phe Asp Pro Ala Ser Ala His Pro Ser Leu
    290                 295                 300

Leu Val Ser Pro Ser Gly Arg Arg Val Glu Cys Val Glu Gln Lys Ala
305                 310                 315                 320

Pro Pro Ala Gly Asp Pro Gln Gln Phe Asp Lys Ala Val Ala Leu
                325                 330                 335

Val Ala Lys Gln Gln Leu Ser Glu Gly Glu His Tyr Trp Glu Val Glu
            340                 345                 350

Val Gly Asp Lys Pro Arg Trp Gly Leu Gly Leu Ile Ser Ala Asp Val
        355                 360                 365

Ser Arg Arg Gly Lys Leu His Pro Thr Pro Ser Gln Gly Phe Trp Met
    370                 375                 380

Leu Gly Leu Arg Glu Gly Lys Val Tyr Glu Ala His Val Glu Ser Lys
385                 390                 395                 400

Glu Pro Lys Val Leu Lys Val Asp Gly Arg Pro Ser Arg Ile Gly Leu
                405                 410                 415

Tyr Leu Ser Phe Arg Asp Gly Val Leu Ser Phe Tyr Asp Ala Ser Asp
            420                 425                 430

Leu Asp Asn Leu Leu Pro Leu Tyr Ala Phe His Glu Arg Leu Pro Gly
        435                 440                 445

Pro Val Tyr Pro Phe Phe Asp Val Cys Trp His Asp Lys Gly Lys Asn
    450                 455                 460

Ala Gln Pro Leu Leu Leu Leu Gly Pro Asp Gly Glu Gln
465                 470                 475
```

-continued

```
<210> SEQ ID NO 10
<211> LENGTH: 477
<212> TYPE: PRT
<213> ORGANISM: Canis sp.
<220> FEATURE:
<221> NAME/KEY: PEPTIDE
<222> LOCATION: (1)..(477)
<223> OTHER INFORMATION: Dog MG53

<400> SEQUENCE: 10
```

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
                20                  25                  30

Phe Cys Arg Ala Cys Leu Ser Arg Val Ala Gly Glu Pro Ala Ala Asp
            35                  40                  45

Gly Thr Val Pro Cys Pro Cys Cys Gln Ala Leu Thr Arg Pro Gln Ala
        50                  55                  60

Leu Ser Thr Asn Gln Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
            115                 120                 125

Leu Lys Thr Gln Leu Pro Gln Gln Lys Leu Gln Leu Gln Glu Ala Cys
        130                 135                 140

Met Arg Lys Glu Lys Ser Val Ala Leu Leu Glu His Gln Leu Met Glu
145                 150                 155                 160

Val Glu Glu Met Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Val Ile Ser Asp Asp Phe
            260                 265                 270

Lys Phe Gln Val Trp Arg Lys Met Phe Arg Ala Leu Met Pro Val Thr
        275                 280                 285

Lys Glu Leu Thr Phe Asp Pro Ser Ser Ala His Pro Ser Leu Val Leu
    290                 295                 300

Ser Pro Ser Gly Arg Arg Val Glu Cys Ser Asp Gln Lys Ala Pro Pro
305                 310                 315                 320

Ala Gly Glu Asp Pro Cys Gln Phe Asp Lys Ala Val Ala Val Val Ala
                325                 330                 335

Gln Gln Val Leu Ser Asp Gly Glu His Tyr Trp Glu Val Gln Val Gly
            340                 345                 350

Glu Lys Pro Arg Trp Ala Leu Gly Val Ile Ala Ala Gln Ala Ser Arg
        355                 360                 365

```
Arg Gly Arg Leu His Ala Val Pro Ser Gln Gly Leu Trp Leu Leu Gly
        370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Arg Pro Thr Arg Ile Gly Ile Tyr
                405                 410                 415

Leu Ser Phe Gly Asp Gly Val Leu Ser Phe Tyr Asp Ala Ser Asp Pro
                420                 425                 430

Asp Ala Leu Glu Leu Leu Phe Ala Phe His Glu Arg Leu Pro Gly Pro
                435                 440                 445

Val Tyr Pro Phe Phe Asp Val Cys Trp His Asp Lys Gly Lys Asn Ala
        450                 455                 460

Gln Pro Leu Leu Leu Val Gly Pro Asp Gly Glu Glu Ala
465                 470                 475

<210> SEQ ID NO 11
<211> LENGTH: 477
<212> TYPE: PRT
<213> ORGANISM: Pan troglodytes
<220> FEATURE:
<221> NAME/KEY: PEPTIDE
<222> LOCATION: (1)..(477)
<223> OTHER INFORMATION: Chimpanzee MG53

<400> SEQUENCE: 11

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255
```

```
Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
        355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Arg Pro
        435                 440                 445

Val Tyr Pro Phe Phe Asp Val Cys Trp His Asp Lys Gly Lys Asn Ala
    450                 455                 460

Gln Pro Leu Leu Leu Val Gly Pro Glu Gly Ala Glu Ala
465                 470                 475

<210> SEQ ID NO 12
<211> LENGTH: 477
<212> TYPE: PRT
<213> ORGANISM: Macaca mulatta
<220> FEATURE:
<221> NAME/KEY: PEPTIDE
<222> LOCATION: (1)..(477)
<223> OTHER INFORMATION: Rhesus Monkey MG53

<400> SEQUENCE: 12

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
```

```
                130                 135                 140
Met Arg Lys Glu Lys Ser Val Ala Val Leu Glu His Gln Leu Val Glu
145                 150                 155                 160

Val Glu Glu Thr Val Arg Gln Phe Arg Gly Val Gly Glu Gln Leu
                165                 170                 175

Gly Lys Met Arg Val Phe Leu Ala Ala Leu Glu Gly Ser Leu Asp Arg
                180                 185                 190

Glu Ala Glu Arg Val Arg Gly Glu Ala Gly Val Ala Leu Arg Arg Glu
                195                 200                 205

Leu Gly Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
                260                 265                 270

Lys Phe Gln Val Trp Arg Lys Met Phe Arg Ala Leu Met Pro Ala Leu
                275                 280                 285

Glu Glu Leu Thr Phe Asp Pro Ser Ser Ala His Pro Ser Leu Val Val
290                 295                 300

Ser Ser Ser Gly Arg Arg Val Glu Cys Ser Gln Lys Ala Pro Pro
305                 310                 315                 320

Ala Gly Glu Asp Pro Arg Gln Phe Asp Lys Ala Val Ala Val Ala
                325                 330                 335

His Gln Gln Leu Ser Glu Gly Glu His Tyr Trp Glu Val Glu Val Gly
                340                 345                 350

Asp Lys Pro Arg Trp Ala Leu Gly Val Ile Ala Ala Glu Gly Pro Arg
                355                 360                 365

Arg Gly Arg Leu His Ala Val Pro Ser Gln Gly Leu Trp Leu Leu Gly
                370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
                420                 425                 430

Asp Ala Leu Val Pro Leu Phe Ala Phe His Glu Arg Leu Pro Gly Pro
                435                 440                 445

Val Tyr Pro Phe Phe Asp Val Cys Trp His Asp Lys Gly Lys Asn Ser
450                 455                 460

Gln Pro Leu Leu Leu Val Gly Ser Glu Gly Ala Glu Ala
465                 470                 475

<210> SEQ ID NO 13
<211> LENGTH: 482
<212> TYPE: PRT
<213> ORGANISM: Bos sp.
<220> FEATURE:
<221> NAME/KEY: PEPTIDE
<222> LOCATION: (1)..(482)
<223> OTHER INFORMATION: Bovine MG53

<400> SEQUENCE: 13

Met Ser Ala Ala Pro Gly Leu Leu His Gln Glu Leu Ser Cys Pro Leu
1               5                   10                  15
```

```
Cys Leu Gln Leu Phe Asp Ala Pro Val Thr Ala Glu Cys Gly His Ser
         20                  25                  30

Phe Cys Arg Ala Cys Leu Ser Arg Val Ala Gly Glu Pro Ala Ala Asp
             35                  40                  45

Gly Thr Val Leu Cys Pro Ser Cys Gln Ala Pro Thr Arg Pro Gln Ala
 50                  55                  60

Leu Ser Thr Asn Leu Gln Leu Ala Arg Leu Val Glu Gly Leu Ala Gln
 65                  70                  75                  80

Val Pro Gln Gly His Cys Glu His Leu Asp Pro Leu Ser Ile Tyr
                 85                  90                  95

Cys Glu Gln Asp Arg Ala Leu Val Cys Gly Val Cys Ala Ser Leu Gly
             100                 105                 110

Ser His Arg Gly His Arg Leu Leu Pro Ala Ala Glu Ala His Ala Arg
         115                 120                 125

Leu Lys Thr Gln Leu Pro Gln Gln Lys Met Gln Leu Gln Glu Ala Cys
 130                 135                 140

Met Arg Lys Glu Lys Ser Val Ala Leu Leu Glu His Gln Leu Leu Glu
145                 150                 155                 160

Val Glu Glu Thr Val Arg Gln Phe Arg Gly Ala Val Gly Glu Gln Leu
                 165                 170                 175

Gly Lys Met Arg Leu Phe Leu Ala Ala Leu Glu Gly Ser Leu Asp Arg
             180                 185                 190

Glu Ala Glu Arg Val Arg Gly Glu Ala Gly Val Ala Leu Arg Arg Glu
         195                 200                 205

Leu Gly Ser Leu Asn Ser Tyr Leu Glu Gln Leu Arg Gln Met Glu Lys
 210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                 245                 250                 255

Pro Pro Ala Arg Leu Asp Ile Gln Leu Pro Ile Ile Ser Asp Asp Phe
             260                 265                 270

Lys Phe Gln Val Trp Arg Lys Met Phe Arg Ala Leu Met Pro Ala Arg
         275                 280                 285

Gln Glu Leu Thr Phe Asp Pro Ser Thr Ala His Pro Ser Leu Val Leu
 290                 295                 300

Ser Asn Ser Gly Arg Cys Val Glu Cys Ser Glu Gln Lys Ala Pro Pro
305                 310                 315                 320

Ala Gly Glu Asp Pro Arg Gln Phe Asp Lys Ala Val Ala Val Val Thr
                 325                 330                 335

His Gln Leu Leu Ser Glu Gly Glu His Tyr Trp Glu Val Glu Val Gly
             340                 345                 350

Asp Lys Pro Arg Trp Ala Leu Gly Val Ile Gly Ala Gln Ala Gly Arg
         355                 360                 365

Arg Gly Arg Leu His Ala Val Pro Ser Gln Gly Leu Trp Leu Leu Gly
 370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Arg Pro Thr Arg Ile Gly Ile Tyr
                 405                 410                 415

Leu Ser Phe Gly Asp Gly Val Leu Ser Phe Tyr Asp Ala Ser Asp Pro
             420                 425                 430

Asp Ala Leu Glu Leu Leu Phe Ala Phe His Glu Arg Leu Pro Gly Pro
         435                 440                 445
```

Val Tyr Pro Phe Phe Asp Val Cys Trp His Asp Lys Gly Lys Asn Ala
    450                 455                 460

Gln Pro Leu Leu Leu Val Gly Pro Glu Val Ser Gly Gly Ser Gly Ser
465                 470                 475                 480

Glu Ala

<210> SEQ ID NO 14
<211> LENGTH: 477
<212> TYPE: PRT
<213> ORGANISM: Rattus sp.
<220> FEATURE:
<221> NAME/KEY: PEPTIDE
<222> LOCATION: (1)..(477)
<223> OTHER INFORMATION: Rat MG53

<400> SEQUENCE: 14

Met Ser Thr Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ile Arg Val Ala Gly Glu Pro Ala Asp Asp
        35                  40                  45

Gly Thr Val Ala Cys Pro Cys Cys Gln Ala Ser Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Thr Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Ala Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Met Phe Leu Ala Ala Leu Glu Ser Ser Leu Asp Arg
            180                 185                 190

Glu Ala Glu Arg Val Arg Gly Glu Ala Gly Val Ala Leu Arg Arg Glu
        195                 200                 205

Leu Ser Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ser Pro
                245                 250                 255

Pro Pro Ala Arg Leu Asp Ile Gln Leu Pro Val Ile Ser Asp Asp Phe
            260                 265                 270

Lys Phe Gln Val Trp Lys Lys Met Phe Arg Ala Leu Met Pro Glu Leu
        275                 280                 285

Glu Glu Leu Thr Phe Asp Pro Ser Ser Ala His Pro Ser Leu Val Val
    290                 295                 300

Ser Ala Ser Gly Arg Arg Val Glu Cys Ser Glu Gln Lys Ala Pro Pro
305                 310                 315                 320

```
Ala Gly Glu Asp Thr Cys Gln Phe Asp Lys Thr Val Ala Val Ala
            325                 330                 335

Lys Gln Leu Leu Ser Gln Gly Glu His Tyr Trp Val Glu Val Gly
            340                 345                 350

Asp Lys Pro Arg Trp Ala Leu Gly Val Met Ala Ala Asp Ala Ser Arg
            355                 360                 365

Arg Gly Arg Leu His Ala Val Pro Ser Gln Gly Leu Trp Leu Leu Gly
            370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Pro Ala Arg Ile Gly Leu Tyr
                405                 410                 415

Leu Ser Phe Ala Asp Gly Val Leu Thr Phe Tyr Asp Ala Ser Asn Thr
            420                 425                 430

Asp Ala Leu Thr Pro Leu Phe Ser Phe His Glu Arg Leu Pro Gly Pro
            435                 440                 445

Val Tyr Pro Met Phe Asp Val Cys Trp His Asp Lys Gly Lys Asn Ser
            450                 455                 460

Gln Pro Leu Leu Leu Val Gly Pro Asp Ser Glu Gln Ala
465                 470                 475

<210> SEQ ID NO 15
<211> LENGTH: 477
<212> TYPE: PRT
<213> ORGANISM: Xenopus laevis
<220> FEATURE:
<221> NAME/KEY: PEPTIDE
<222> LOCATION: (1)..(477)
<223> OTHER INFORMATION: Xenopus laevis

<400> SEQUENCE: 15

Met Ser Thr Pro Gln Leu Met Gln Gly Met Gln Lys Asp Leu Thr Cys
1               5                   10                  15

Gln Leu Cys Leu Glu Leu Phe Arg Ala Pro Val Thr Pro Glu Cys Gly
            20                  25                  30

His Thr Phe Cys Gln Gly Cys Leu Thr Gly Val Pro Lys Asn Gln Asp
            35                  40                  45

Gln Asn Gly Ser Thr Pro Cys Pro Thr Cys Ser Pro Ser Arg Pro
50                  55                  60

Glu Thr Leu Gln Ile Asn Arg Gln Leu Glu His Leu Val Gln Ser Phe
65                  70                  75                  80

Lys Gln Val Pro Gln Gly His Cys Leu Glu His Met Asp Pro Leu Ser
                85                  90                  95

Val Tyr Cys Glu Gln Asp Lys Glu Leu Ile Cys Gly Val Cys Ala Ser
            100                 105                 110

Leu Gly Lys His Lys Gly His Asn Ile Ile Thr Ala Ser Glu Ala Phe
            115                 120                 125

Ala Lys Leu Lys Arg Gln Leu Pro Gln Gln Val Ile Leu Gln Glu
            130                 135                 140

Ala Arg Leu Lys Lys Glu Lys Thr Val Ala Val Leu Asp Arg Gln Val
145                 150                 155                 160

Ala Glu Val Gln Asp Thr Val Ser Arg Phe Lys Gly Asn Val Lys His
                165                 170                 175

Gln Leu Asn Ala Met Arg Ser Tyr Leu Asn Ile Met Glu Ala Ser Leu
            180                 185                 190

Gly Lys Glu Ala Asp Lys Ala Glu Ser Ala Ala Thr Glu Ala Leu Leu
```

```
            195                 200                 205
Val Glu Arg Lys Thr Met Gly His Tyr Leu Asp Gln Leu Arg Gln Met
210                 215                 220

Glu Gly Val Leu Lys Asp Val Glu Gly Gln Glu Gln Thr Glu Phe Leu
225                 230                 235                 240

Arg Lys Tyr Cys Val Ala Ala Arg Leu Asn Lys Ile Leu Ser Glu
                245                 250                 255

Ser Pro Pro Gly Arg Leu Asp Ile Gln Leu Pro Ile Ile Ser Asp
            260                 265                 270

Glu Phe Lys Phe Gln Val Trp Arg Lys Met Phe Arg Ala Leu Met Pro
        275                 280                 285

Ala Leu Glu Asn Met Thr Phe Asp Pro Asp Thr Ala Gln Gln Tyr Leu
290                 295                 300

Val Val Ser Ser Glu Gly Lys Ser Val Glu Cys Ala Asp Gln Lys Gln
305                 310                 315                 320

Ser Val Ser Asp Glu Pro Asn Arg Phe Asp Lys Ser Asn Cys Leu Val
                325                 330                 335

Ser Lys Gln Ser Phe Thr Glu Gly His Tyr Trp Glu Val Ile Val
            340                 345                 350

Glu Asp Lys Pro Arg Trp Ala Leu Gly Ile Ile Ser Glu Thr Ala Asn
        355                 360                 365

Arg Lys Gly Lys Leu His Ala Thr Pro Ser Asn Gly Phe Trp Ile Ile
370                 375                 380

Gly Cys Lys Glu Gly Lys Val Tyr Glu Ala His Thr Glu Gln Lys Glu
385                 390                 395                 400

Pro Arg Val Leu Arg Val Glu Gly Arg Pro Glu Lys Ile Gly Val Tyr
                405                 410                 415

Leu Ser Phe Ser Asp Gly Val Val Ser Phe Phe Asp Ser Ser Asp Glu
            420                 425                 430

Asp Asn Leu Lys Leu Leu Tyr Thr Phe Asn Glu Arg Phe Ser Gly Arg
        435                 440                 445

Leu His Pro Phe Phe Asp Val Cys Trp His Asp Lys Gly Lys Asn Ser
450                 455                 460

Gln Pro Leu Lys Ile Phe Tyr Pro Pro Ala Glu Gln Leu
465                 470                 475

<210> SEQ ID NO 16
<211> LENGTH: 477
<212> TYPE: PRT
<213> ORGANISM: Xenopus sp.
<220> FEATURE:
<221> NAME/KEY: PEPTIDE
<222> LOCATION: (1)..(477)
<223> OTHER INFORMATION: Xenopus tropicalis MG53

<400> SEQUENCE: 16

Met Ser Thr Pro Gln Leu Met Gln Gly Met Gln Lys Asp Leu Thr Cys
1               5                   10                  15

Pro Leu Cys Leu Glu Leu Phe Arg Ala Pro Val Thr Pro Glu Cys Gly
            20                  25                  30

His Thr Phe Cys Gln Gly Cys Leu Thr Gly Ala Pro Lys Asn Gln Asp
        35                  40                  45

Gln Asn Gly Ser Thr Pro Cys Pro Thr Cys Gln Thr Pro Ser Arg Pro
    50                  55                  60

Glu Thr Leu Gln Ile Asn Arg Gln Leu Glu His Leu Val Gln Ser Phe
65                  70                  75                  80
```

```
Lys Gln Val Pro Lys Gly His Cys Leu Glu His Leu Asp Pro Leu Ser
                85                  90                  95

Val Tyr Cys Glu Gln Asp Lys Glu Leu Ile Cys Gly Val Cys Ala Ser
            100                 105                 110

Leu Gly Lys His Lys Gly His Asn Ile Ile Thr Ala Ala Glu Ala Tyr
        115                 120                 125

Ala Lys Leu Lys Arg Gln Leu Pro Gln Gln Gln Val Ile Leu Gln Glu
    130                 135                 140

Ala Arg Leu Lys Lys Glu Lys Thr Val Ala Val Leu Asp Arg Gln Val
145                 150                 155                 160

Ala Glu Val Gln Asp Thr Val Ser Arg Phe Lys Gly Asn Val Lys His
                165                 170                 175

Gln Leu Asn Ala Met Arg Ser Tyr Leu Ser Ile Met Glu Ala Ser Leu
            180                 185                 190

Ser Lys Glu Ala Asp Asn Ala Glu His Thr Ala Thr Glu Ala Leu Leu
        195                 200                 205

Val Glu Arg Lys Thr Met Gly His Tyr Leu Asp Gln Leu Arg Gln Met
    210                 215                 220

Asp Gly Val Leu Lys Asp Val Glu Ser Gln Glu Gln Thr Glu Phe Leu
225                 230                 235                 240

Arg Lys Tyr Cys Val Ala Ala Arg Leu Asn Lys Ile Leu Ala Glu
                245                 250                 255

Ser Pro Pro Pro Gly Arg Leu Asp Ile Gln Leu Pro Ile Ile Ser Asp
            260                 265                 270

Glu Phe Lys Phe Gln Val Trp Arg Lys Met Phe Arg Ala Leu Met Pro
        275                 280                 285

Ala Leu Glu Asn Leu Thr Phe Asp Pro Asp Thr Ala Gln Gln Asn Leu
    290                 295                 300

Val Val Phe Ser Asp Gly Lys Ser Val Glu Cys Ser Glu Gln Lys Gln
305                 310                 315                 320

Ser Val Ser Asp Glu Pro Asn Arg Phe Asp Lys Ser Asn Cys Leu Val
                325                 330                 335

Ser Lys Glu Ser Phe Thr Glu Gly Glu His Tyr Trp Glu Val Leu Val
            340                 345                 350

Glu Asp Lys Pro Arg Trp Ala Leu Gly Val Ile Ser Glu Thr Ala Asn
        355                 360                 365

Arg Lys Gly Lys Leu His Ala Ser Pro Ser Asn Gly Phe Trp Leu Ile
    370                 375                 380

Gly Cys Lys Glu Gly Lys Val Tyr Glu Ala His Thr Glu Gln Lys Glu
385                 390                 395                 400

Pro Arg Val Leu Arg Val Glu Gly Arg Pro Glu Lys Ile Gly Ile Tyr
                405                 410                 415

Leu Ser Phe Ser Asp Gly Val Val Ser Phe Phe Asp Ser Ser Asp Glu
            420                 425                 430

Asp Asn Ile Lys Leu Leu Tyr Thr Phe Asn Glu Arg Phe Ser Gly Arg
        435                 440                 445

Leu His Pro Phe Phe Asp Val Cys Trp His Asp Lys Gly Lys Asn Ala
    450                 455                 460

Gln Pro Leu Lys Ile Phe Tyr Pro Pro Ala Glu Gln Leu
465                 470                 475

<210> SEQ ID NO 17
<211> LENGTH: 101
<212> TYPE: PRT
<213> ORGANISM: Human immunodeficiency virus type 1
```

```
<220> FEATURE:
<221> NAME/KEY: PEPTIDE
<222> LOCATION: (1)..(101)
<223> OTHER INFORMATION: HIV-1 TAT protein

<400> SEQUENCE: 17

Met Glu Pro Val Asp Pro Asn Leu Glu Pro Trp Lys His Pro Gly Ser
1               5                   10                  15

Gln Pro Pro Thr Ala Cys Ser Lys Cys Tyr Cys Lys Lys Cys Cys Trp
            20                  25                  30

His Cys Gln Leu Cys Phe Leu Lys Lys Gly Leu Gly Ile Ser Tyr Gly
        35                  40                  45

Arg Lys Lys Arg Lys His Arg Arg Gly Thr Pro Gln Ser Ser Lys Asp
    50                  55                  60

His Gln Asn Pro Ile Pro Glu Gln Pro Leu Pro Ile Ile Arg Gly Asn
65                  70                  75                  80

Gln Thr Gly Pro Lys Glu Gln Lys Lys Thr Val Ala Ser Lys Ala Glu
                85                  90                  95

Arg Asp Leu Cys Ala
            100

<210> SEQ ID NO 18
<211> LENGTH: 66
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(66)
<223> OTHER INFORMATION: Scrambled shRNA for MG53 - sense

<400> SEQUENCE: 18
gtacctcgcc tgccgtccaa agttgtaatc aagagttaca actttggacg gcaggctttt    60
tggaaa                                                                66

<210> SEQ ID NO 19
<211> LENGTH: 66
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(66)
<223> OTHER INFORMATION: Scrambled shRNA for MG53 - antisense

<400> SEQUENCE: 19
agcttttcca aaagcctgc cgtccaaagt tgtaactctt gattacaact ttggacggca    60
ggcgag                                                                66

<210> SEQ ID NO 20
<211> LENGTH: 66
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(66)
<223> OTHER INFORMATION: shRNA for MG53

<400> SEQUENCE: 20
gtacctcgag ctgtcaagcc tgaactcttc aagagagagt tcaggcttga cagctctttt    60
```

-continued tggaaa 66

<210> SEQ ID NO 21
<211> LENGTH: 66
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(66)
<223> OTHER INFORMATION: shRNA for MG53

<400> SEQUENCE: 21
agcttttcca aaaagagctg tcaagcctga actctctctt gaagagttca ggcttgacag    60
ctcgag                                                              66

<210> SEQ ID NO 22
<211> LENGTH: 65
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(65)
<223> OTHER INFORMATION: Scrambled shRNA for Cav-3 - sense

<400> SEQUENCE: 22
gatccgcgga gacatagcct gtaattcaag agattacagg ctatgtctcc gcttttttac    60
cggtg                                                               65

<210> SEQ ID NO 23
<211> LENGTH: 65
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(65)
<223> OTHER INFORMATION: Scrambled shRNA for Cav-3 - antisense

<400> SEQUENCE: 23
aattcaccgg taaaaaagcg gagacatagc ctgtaatctc ttgaattaca ggctatgtct    60
ccgcg                                                               65

<210> SEQ ID NO 24
<211> LENGTH: 65
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(65)
<223> OTHER INFORMATION: shRNA for Cav-3 - sense

<400> SEQUENCE: 24
gatccggaca ttcactgcaa ggagttcaag agactccttg cagtgaatgt ccttttttac    60
cggtg                                                               65

<210> SEQ ID NO 25
<211> LENGTH: 65
<212> TYPE: DNA
<213> ORGANISM: Artificial Sequence
<220> FEATURE:

-continued

```
<223> OTHER INFORMATION: Chemically Synthesized
<220> FEATURE:
<221> NAME/KEY: misc_feature
<222> LOCATION: (1)..(65)
<223> OTHER INFORMATION: shRNA for Cav-3 - antisense

<400> SEQUENCE: 25
aattcaccgg taaaaaagga cattcactgc aaggagtctc ttgaactcct tgcagtgaat    60
gtccg                                                                65
```

MG53 COMPOSITIONS AND METHODS OF USE

CROSS-REFERENCE TO RELATED APPLICATIONS

Under 35 U.S.C. §119(e) this application claims the benefit of U.S. Provisional Applications Nos. 60/830,013 filed Jul. 11, 2006; and 60/876,871 filed Dec. 22, 2006, both of which are hereby incorporated by reference in their entirety for all purposes.

STATEMENT REGARDING FEDERALLY SPONSORED RESEARCH

The U.S. Government has certain rights in this invention pursuant to the following grants: RO1-CA095739; RO1-AG015556; RO1-HL069000 awarded to Dr. Jianjie Ma by the United States National Institutes of Health (NIH).

INCORPORATION BY REFERENCE

In compliance with 37 C.F.R. §1.52(e)(5), the sequence information contained on compact disc, file name: Ma_2007utility SEQ List_ST25.txt; size 61 KB; created on: Jun. 29, 2007; using PatentIn-3.4, and Checker 4.4.0 is hereby incorporated by reference in its entirety. The Sequence Listing information recorded in computer readable form (CRF) is identical to the written Sequence Listing provided herewith. The data in the paper copy of the Sequence Listing, and Computer Readable Form of the Sequence Listing submitted herewith contain no new matter, and are fully supported by the priority applications, U.S. Provisional Patent Applications Nos. 60/830,013; and 60/876,871.

FIELD OF THE INVENTION

This invention relates to polypeptides, nucleic acids encoding the same, antibodies that immunospecifically-bind to the polypeptides and associated methods of use.

BACKGROUND

In response to external damage and internal degeneration, the cells of the body must repair the membrane surrounding the each individual cell in order to maintain their function and the health of the organism. Defects in the ability of the cell to repair external membranes have been linked to many diseases and pathological conditions, for example, neurodegenerative diseases (e.g., Parkinson's Disease), heart attacks, heart failure, muscular dystrophy, bed sores, diabetic ulcers, oxidative damage, and tissue damage such as sinusitis that occurs as side effect from the administration of chemotherapeutic agents. Also, the muscle weakness and atrophy associated with various diseases, as well as the normal aging process, has been linked to altered membrane repair. In order for these cells to repair their membranes in response to acute damage they make use of small packets of membrane that are inside of the cell, referred to as vesicles. These vesicles are normally found within the cell, but upon damage to the cell membrane, these vesicles move to the damage site and form a patch to maintain the cell integrity. Without this essential function, the cell can die and the cumulative effect of this cellular injury can eventually result in dysfunction of the tissue or organ.

Many companies are interested in approaches to improve the regenerative capacity of various tissues. For example, the wound repair market, alone, is expected to exceed $11 billion by 2009. Therefore, there exists an ongoing need for the development of pharmaceutical modulators of the cell membrane repair process for the treatment of conditions related to acute and chronic cellular and tissue damage.

SUMMARY

The present invention relates to the surprising and unexpected discovery of proteins involved in the repair of cell membrane damage. The invention generally relates to nucleic acids, and includes polypeptides encoded from nucleic acids of the invention. More specifically, the invention relates to compositions, for example, nucleic acids, which are useful for inhibiting transcription or translation of target nucleic acids; nucleic acids encoding cytoplasmic, nuclear, membrane bound, and secreted polypeptides; as well as vectors, host cells, antibodies, recombinant proteins, pseudopeptides, fusion proteins, chemical compounds, and methods for producing the same.

In certain aspects, the present invention also relates to compositions useful as therapeutics for treating and prevention of diseases and disorders. Therapeutic compositions of the invention comprise nucleic acids, including an interfering nucleic acids, and nucleic acids encoding polypeptides corresponding to the protein of SEQ ID NO. 1 (herein, "MG53"), MG53 polypeptides, homologs and portions thereof, MG53 psuedopeptides, MG53 peptide analogs and MG53 peptidomimetics; as well as compounds that can modulate the activity of MG53 or intermolecular interactions involving MG53, and for example, caveolin-3 (SEQ ID NO. 8). As described herein, MG53 mediates the repair of damage to cellular membranes, and therefore, the targeting and modulating MG53 gene expression, polypeptide synthesis, activity or protein-protein interactions represent a novel therapeutic intervention for tissue repair.

In certain additional aspects the invention relates to compositions and methods related to the treatment of tissue damage. In certain exemplary embodiments, the invention encompasses, for example, the administration of an effective amount of a therapeutic composition of the invention for the promotion of wound healing; for ameliorating surgical trauma, for treatment and/or prevention of age-related deficiencies in tissue repair that occur as a natural side-effect of the aging process; for treatment and/or prevention of injury to any type of muscle tissue, such as those occurring in subjects suffering from cardiovascular diseases and/or sports-related injuries; as well as the repair and regeneration of body tissues through cosmetic or personal care use.

In addition, the invention relates to nucleic acids, including interfering nucleic acids, and polypeptides encoding MG53 interacting proteins, for example, caveolin-3 (SEQ ID NO. 8) polypeptides and homologs thereof; psuedopeptides and peptidomimetics; as well as compounds that can modulate the activity of caveolin-3 or its intermolecular interactions with MG53. Therefore, in additional aspects, the present invention encompasses methods for the targeting of caveolin-3 gene expression, activity, and/or intermolecular interactions for the treatment and/or prevention of a disease or disorder in a subject, for example, for the promotion of tissue repair as described above.

The preceeding general areas of utility are given by way of example only and are not intended to be limiting on the scope of the present disclosure and appended claims. Additional objects and advantages of the present invention will be appreciated by one of ordinary skill in the art in light of the instant claims, description, and examples. These additional objects and advantages are expressly included within the scope of the present invention.

BRIEF DESCRIPTION OF THE DRAWINGS

FIG. 1: MG53 is a muscle specific member of the TRIM protein family. An alignment of the protein sequence of MG53 from various organisms (See SEQ ID NOs.: 1, 3, 5, 9-16) reveals this protein to be a member of the TRIM family. Functional domains are boxed in grey while arrows indicate the domain continues onto another line of the sequence.

FIG. 10. Progressive pathology is seen in mg53−/− skeletal muscle due to increased damage of cell membranes. A. Haematoxylin and Eosin (H/E) staining illustrates increased number of central nuclei (arrows) in aging mg53−/− muscle (10m) versus young (3m) wild type (wt) or mg53−/− mice. B. The diameter of muscle fibers in aged (8-10 month) mg53−/− mice (blue, n=541) decreased compared to aged (8-10 month) wild type controls (black, n=562) while there is no difference in young (3-5 months) wt (n=765) versus mg53−/− (n=673) muscle. Percentage of muscle fibers that display central nuclei in mg53−/− skeletal muscle increases with age when compared to wt. Data is mean±s.e.m., * p<0.05 by ANOVA. C. Trace recordings of contractile performance of intact soleus muscle obtained from mice subjected to 30 min downhill exercise running was assessed using an in vitro voltage stimulation protocol, following described procedures. Black trace represents wt muscle, blue trace corresponds to mg53−/− muscle. D. Prior to fatigue stimulation (Pre, open bars), the maximal tetanic force, normalized in g/mg total protein, was significantly lower in aging mg53−/− muscle (blue) versus wt (black) (n=4). At 6 min after fatigue stimulation (After, closed bars), the wt muscle recovered significantly more than mg53−/− muscle. * p<0.05 by ANOVA. E. Extensive Evans blue staining reveals serve damage in mg53−/− skeletal muscle subjected to down-hill running when compared to minimal staining in wt muscles. F. Chart of the quantity of Evans blue dye extracted by formamide from aging mg53−/− (blue) and wt (black) skeletal muscle following exercise. The data represents mean value of Evans blue (ng) per g of muscle±s.e.m. n=8-12, * p<0.005 by Student's t-test.

FIG. 13. Role of TRIM and SPRY domains in targeting of MG53 to the cell surface membrane of muscle cells. A. Scheme of the MG53 deletion fusion protein constructs with GFP fused to the N-terminus or C-terminus. With reference to SEQ ID NO. 1, "TRIM" represents a.a. 1-287 and "SPRY" represents a.a. 288-477 and includes both the PRY and SPRY motifs. B. Representative confocal images showing intracellular localization of each deletion construct in C2C12 cells. Scale bar is 5 μm. C. MG53 interacts with caveolin-3 through the TRIM motif. Cell lysate from CHO cells co-transfected with GFP-MG53 or GFP-TRIM and pcDNA-Cav-3 was subjected to IP with anti-caveolin-3 (mouse monoclonal antibody). (Lane 1, mixed cell lysate as positive control; Lane 2, normal mouse IgG as negative control; lane 3, lysate from cells overexpressing GFP-MG53; Lane 4, lysate from cells overexpressing GFP-TRIM).

DETAILED DESCRIPTION

Figure 2:
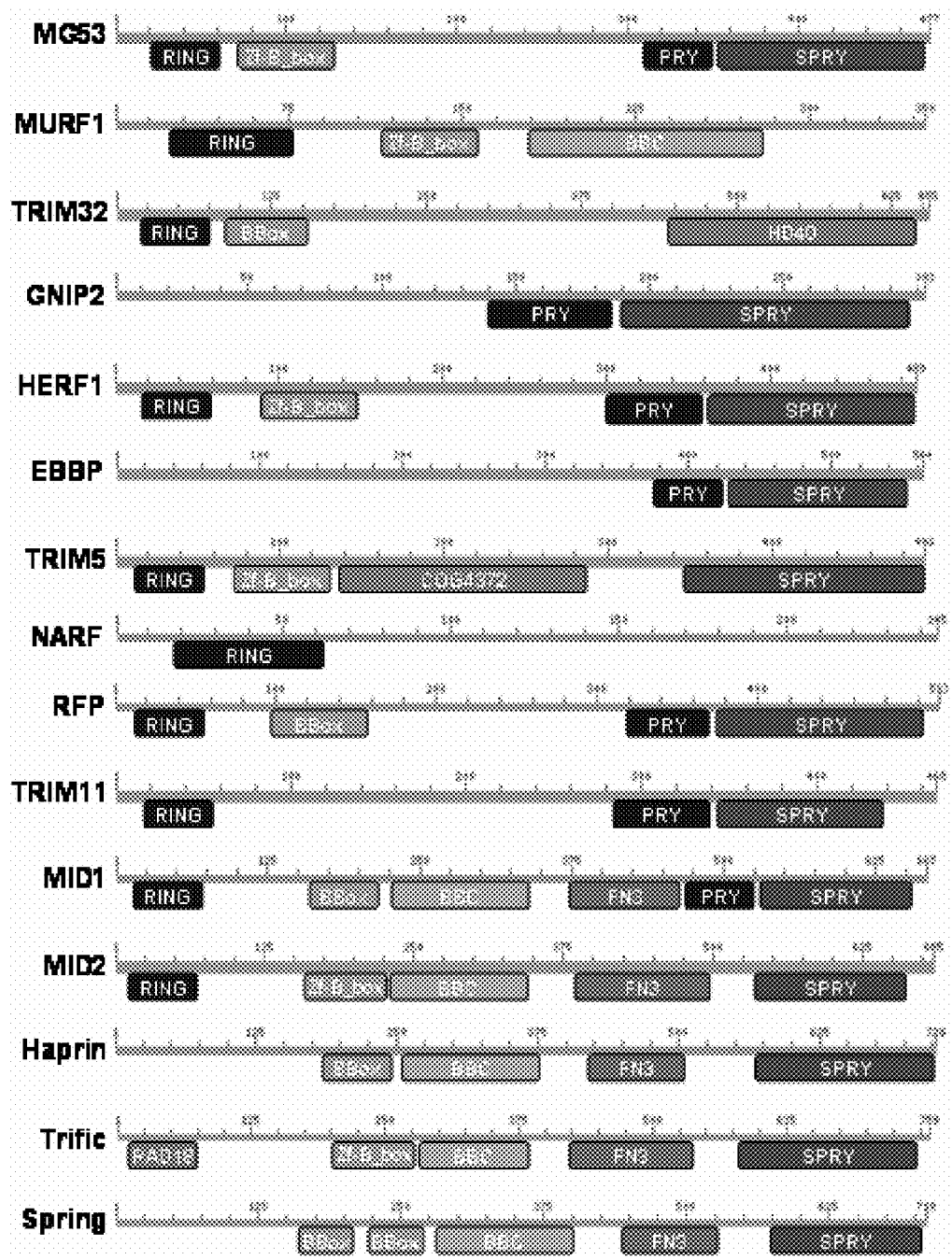
FIG. 2: Illustrates an exemplary domain comparison of some homologous proteins that contain one or more of the conserved tripartite motifs which are present in MG53. MG53 is unique in it's ability to translocate to an injury site at the cell membrane following multiple forms of insult and mediate repair of the damaged membrane—a function which is not exhibited by the other TRIM family proteins listed.

The present invention provides novel nucleotides and polypeptides encoded thereby. Included in the invention are the novel nucleic acid sequences and their encoded polypeptides. The sequences are collectively referred to herein as "MG53 nucleic acids" or "MG53 polynucleotides" and the corresponding encoded polypeptides are referred to as "MG53 polypeptides" or "MG53 proteins." Unless indicated otherwise, "MG53" is meant to refer to any of the novel sequences disclosed herein.

Dynamic membrane repair is essential not only for long-term maintenance of cellular integrity but also for recovery from acute cell injury. Membrane repair defects have been linked to numerous disease states including muscular dystrophy, heart failure and neurodegeneration. Repair of the cell membrane requires intracellular vesicular trafficking that is associated with accumulation of vesicles at the plasma membrane.

The present invention relates to the discovery that vesicular fusion during acute membrane repair is driven by mitsugumin53 (MG53) (SEQ ID NO. 1), a novel muscle-specific tri-partite motif (TRIM) family protein. MG53 expression is necessary to allow intracellular vesicles trafficking to and fusion with the plasma membrane. Acute injury of the cellular membrane leads to recruitment of MG53-containing vesicles to patch the membrane at the injury site. Cells that are null for MG53 display defects in membrane repair in response to multiple stresses, including laser-induced injury, muscle damage induced by exercise, and compromised recovery of muscle contractile function after fatigue. Thus, MG53 is a critical component of the vesicular trafficking events that underlie the acute repair and remodeling of cellular membranes.

The invention is based in part upon the discovery of nucleic acid sequences encoding novel polypeptides. The novel nucleic acids and polypeptides are referred to herein as MG53 nucleic acids and polypeptides.

In one aspect, the invention provides an isolated MG53 nucleic acid molecule encoding a MG53 polypeptide that includes a nucleic acid sequence that has at least 30%, 40%, 50%, 60%, 70%, 80%, 90% or 100% identity to the nucleic acids disclosed in SEQ ID NOS: 2, 4, and 6. In certain embodiments, the isolated MG53 nucleic acid molecule will hybridize under stringent conditions to a nucleic acid sequence complementary to a nucleic acid molecule that includes a protein-coding sequence of a MG53 nucleic acid sequence. The invention also includes an isolated nucleic acid that encodes a MG53 polypeptide, or a fragment, homolog, analog, fusion protein, pseudopeptide, peptidomimetic or derivative thereof. For example, the nucleic acid can encode a polypeptide at least 30%, 40%, 50%, 60%, 70%, 80%, 90% or 100% identity to a polypeptide comprising the amino acid sequences of SEQ ID NOS: 1, 3, 5, and 7. The nucleic acid can be, for example, a genomic DNA fragment or a cDNA molecule that includes the nucleic acid sequence of any of SEQ ID NOS: 2, 4, and 6.

Also included in the invention is an oligonucleotide, e.g., an oligonucleotide which includes at least 6 contiguous nucleotides of a MG53 nucleic acid (e.g., SEQ ID NOS: 2, 4, and 6) or a complement of said oligonucleotide.

Also included in the invention are substantially purified MG53 polypeptides (SEQ ID NOS: 1, 3, 5, and 7). In certain embodiments, the MG53 polypeptides include an amino acid sequence that is substantially identical to the amino acid sequence of a human MG53 polypeptide.

The invention also features antibodies that immunoselectively-bind to MG53 polypeptides, or fragments, homologs, analogs, pseudopeptides, peptidomimetics or derivatives thereof.

In another aspect, the invention includes pharmaceutical compositions that include therapeutically- or prophylactically-effective amounts of a therapeutic and a pharmaceutically-acceptable carrier. The therapeutic can be, e.g., a MG53 nucleic acid, for example, a peptide nucleic acid, a cDNA, or RNA, such as for example, a small inhibitory RNA; a MG53 polypeptide; or an antibody specific for a MG53 polypeptide. In a further aspect, the invention includes, in one or more containers, a therapeutically- or prophylactically-effective amount of this pharmaceutical composition.

In a further aspect, the invention includes a method of producing a polypeptide by culturing a cell that includes an endogenous or exogenously expressed MG53 nucleic acid, under conditions allowing for expression of the MG53 polypeptide encoded by the DNA. If desired, the MG53 polypeptide can then be recovered.

In still another aspect the invention includes a method of producing a polypeptide by culturing a cell that contains an endogenous MG53 nucleic acid disposed upstream or downstream of an exogenous promoter. In certain embodiments, the exogenous promoter is incorporated into a host cell's genome through homologous recombination, strand break or mismatch repair mechanisms.

In another aspect, the invention includes a method of detecting the presence of a MG53 polypeptide in a sample. In the method, a sample is contacted with a compound that selectively binds to the polypeptide under conditions allowing for formation of a complex between the polypeptide and the compound. The complex is detected, if present, thereby identifying the MG53 polypeptide within the sample.

The invention also includes methods to identify specific cell or tissue types based on their expression of a MG53 nucleic acid, polypeptide or MG53 fusion polypeptide. For example, in certain embodiments the invention includes fusion proteins comprising a "tag" or indicator portion and an MG53 portion. In certain aspects the tag or indicator portion can be a peptide adapted for purification purposes, for example, FLAG tag, 6×His tag, or the like. In other aspects, the tag peptide comprises a peptide adapted for providing a signal such as an antibody epitope or a fluorescent peptide. Still other aspects include the fusion of the MG53 with a peptide that is adapted for mediating subcellular localization or translocation across a cellular membrane, for example, a TAT fusion protein from the HIV virus.

Also included in the invention is a method of detecting the presence of a MG53 nucleic acid molecule in a sample by contacting the sample with a MG53 nucleic acid probe or primer, and detecting whether the nucleic acid probe or primer bound to a MG53 nucleic acid molecule in the sample.

In a further aspect, the invention provides a method for modulating the activity of a MG53 polypeptide by contacting a cell sample that includes the MG53 polypeptide with a compound that binds to the MG53 polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

Also within the scope of the invention is the use of a therapeutic of the invention in the manufacture of a medicament for treating or preventing disorders or syndromes including, e.g., cardiovascular disease, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, hypercoagulation, hemophilia, ulcers, wounds, lesions, cuts, abrasions, oxidative damage, age-related tissue degeneration, surgically related lesions, burns, muscle weakness, muscle atrophy, connective tissue disorders, idiopathic thrombocytopenic purpura, heart failure, secondary pathologies caused by heart failure and hypertension, hypotension, angina pectoris, myocardial infarction, tuberous sclerosis, scleroderma, transplantation, autoimmune disease, lupus erythematosus, viral/bacterial/parasitic infections, multiple sclerosis, autoimmune disease, allergies, immunodeficiencies, graft versus host disease, asthma, emphysema, ARDS, inflammation and modulation of the immune response, viral pathogenesis, aging-related disorders, Th1 inflammatory diseases such as rheumatoid arthritis, multiple sclerosis, inflammatory bowel diseases, AIDS, wound repair, heart attacks, heart failure, muscular dystrophy, bed sores, diabetic ulcers, oxidative damage, and tissue damage such as sinusitis or mucositis, wrinkles, eczema or dermatitis, dry skin, obesity, diabetes, endocrine disorders, anorexia, bulimia, renal artery stenosis, interstitial nephritis, glomerulonephritis, polycystic kidney disease, systemic, renal tubular acidosis, IgA nephropathy, nephrological diseases, hypercalceimiai, Lesch-Nyhan syndrome, Von Hippel-Lindau (VHL) syndrome, trauma, regeneration (in vitro and in vivo), Hirschsprung's disease, Crohn's Disease, appendicitis, endometriosis, laryngitis, psoriasis, actinic keratosis, acne, hair growth/loss, allopecia, pigmentation disorders, myasthenia gravis, alpha-mannosidosis, beta-mannosidosis, other storage disorders, peroxisomal disorders such as zellweger syndrome, infantile refsum disease, rhizomelic chondrodysplasia (chondrodysplasia punctata, rhizomelic), and hyperpipecolic acidemia, osteoporosis, muscle disorders, urinary retention, Albright Hereditary Ostoeodystrophy, ulcers, Alzheimer's disease, stroke, Parkinson's disease, Huntington's disease, cerebral palsy, epilepsy, Lesch-Nyhan syndrome, multiple sclerosis, ataxia-telangiectasia, behavioral disorders, addiction, anxiety, pain, neuroprotection, Stroke, Aphakia, neurodegenerative disorders, neurologic disorders, developmental defects, conditions associated with the role of GRK2 in brain and in the regulation of chemokine receptors, encephalomyelitis, anxiety, schizophrenia, manic depression, delirium, dementia, severe mental retardation and dyskinesias, Gilles de la Tourette syndrome, leukodystrophies, cancers, breast cancer, CNS cancer, colon cancer, gastric cancer, lung cancer, melanoma, ovarian cancer, pancreatic cancer, kidney cancer, colon cancer, prostate cancer, neuroblastoma, and cervical cancer, Neoplasm; adenocarcinoma, lymphoma; uterus cancer, benign prostatic hypertrophy, fertility, control of growth and development/differentiation related functions such as but not limited maturation, lactation and puberty, reproductive malfunction, and/or other pathologies and disorders of the like.

The therapeutic composition of the invention comprises, in certain embodiments, for example, an MG53 nucleic acid; a nucleic acid that binds an MG53 encoding nucleic acid; an MG53 polypeptide, peptide analog, pseudopeptide or peptidomimetic based thereon; a small molecule modulator of MG53 or a MG53 protein-protein interaction; or a MG53-specific antibody or biologically-active derivatives or fragments thereof. As described herein, MG53 mediates the repair of damage to cellular membranes. Therefore, targeting the expression and/or activity of these nucleic acids, polypeptides, and homologs thereof will allow for a novel treatment of various acute and chronic diseases and conditions related to tissue repair.

In certain other aspects, the invention includes methods for the treatment of or amelioration of tissue damage and/or disorders related to tissue damage comprising administering an effective amount of the composition of the invention to a subject in need thereof. In certain embodiments, the invention comprises methods for treating tissue damage or wounds, for example, cuts, ebrasions, lesions, ulcers, burns, bed sores, gum diseases, mucositis, and the like, comprising administering an effective amount of the therapeutic composition of the invention to a subject in need thereof.

In still other embodiments, the invention comprises therapeutic compositions useful as a surgical adjuvant. In any of the embodiments described herein, the surgical adjuvant composition of the invention can be used or applied as a stand alone therapeutic directly to the surgical site or it can be integrally associated with a surgical or medical implement, for example, the therapeutic of the invention may be conjugated to a polymer-based stent, tube or other implantable device, such that the therapeutic diffuses to the site of action in a controlled manner to accelerate healing and/or to minimize trauma from an invasive surgical procedure. In another embodiment, the therapeutic composition of the invention is applied as, for example, a film or coating to the medical implement such that the therapeutic diffuses into the blood stream or surrounding tissues and/or wears away, and is thereby delivered directly to the site of tissue damage; minimizing or ameliorating the amount of cellular damage that occurs due to the use of the surgical implement.

In still other embodiments, the invention comprises methods for the treatment and/or prevention of deficiencies in tissue repair that occur as a natural side-effect of the aging process (e.g., skin rejuvenation, receding gums, bone degeneration, arthritis, Alzheimer's, Parkinson's, and the like). In certain aspects of this embodiment, the invention comprises administering an effective amount of a therapeutic composition of the invention to a subject suffering from age-related deficiencies in tissue repair capacity, tissue integrity, and/or tissue elasticity. In certain embodiments, the age-related deficiency is at least one of wrinkles, crows feet, facial lines, pot marks, scars, fibroids, sun spots, and the like, or combinations thereof.

Furthermore, due to the muscle-specific nature of the expression of the endogenous MG53 gene, the invention encompasses methods for the treatment and/or prevention of any type of muscle or vascular cell/tissue injury, for example, tissue injury that occurs as a result of cardiovascular disease, for example, myocardial infarction; or rigorous physical activity, for example, sports-related injuries, comprising administering an effective amount of the therapeutic of the invention to a subject in need thereof.

In still other embodiments, the invention comprises a cosmetic composition useful for the repair, regeneration, or restoration of body tissues comprising the therapeutic of the invention and a cosmetically suitable carrier or excipient. In one aspect of this embodiment, the invention encompasses a method of enhancing the appearance of skin comprising administering an effective amount of the therapeutic composition of the invention in a cosmetic to a subject.

In any aspect of the invention, the therapeutic composition of the invention can be in any pharmaceutically acceptable form and administered by any pharmaceutically acceptable route, for example, the therapeutic composition can be administered as an oral dosage, either single daily dose or unitary dosage form, for the treatment of a muscle damage due to a myocardial infarction, sclerotic lesion, or muscle tear due to sports-related activity to promote the regeneration and repair of the damaged muscle tissue. Such pharmaceutically acceptable carriers and excipients and methods of administration will be readily apparent to those of skill in the art.

In addition, the invention relates to nucleic acids, including interfering nucleic acids, and polypeptides encoding MG53 interacting proteins, for example, caveolin-3 (SEQ ID NO. 8) polypeptides and homologs thereof psuedopeptides and peptidomimetics; as well as compounds that can modulate the activity of caveolin-3 or its intermolecular interactions with MG53. Therefore, in additional aspects, the present invention encompasses methods for the targeting of caveolin-3 gene expression, activity, and/or intermolecular interactions for the treatment and/or prevention of a disease or disorder in a subject, for example, for the promotion of tissue repair as described above.

For example, the compositions of the present invention will have efficacy for treatment of patients suffering from the diseases and disorders disclosed above and/or other pathologies and disorders of the like. The polypeptides can be used as immunogens to produce antibodies specific for the invention, and as vaccines. They can also be used to screen for potential agonist and antagonist compounds. In addition, a cDNA encoding MG53 may be useful in gene therapy, and MG53 may be useful when administered to a subject in need thereof. By way of non-limiting example, the compositions of the present invention will have efficacy for treatment of patients suffering from the diseases and disorders disclosed above and/or other pathologies and disorders of the like.

The invention further includes a method for screening for a modulator of disorders or syndromes including, e.g., the diseases and disorders disclosed above and/or other pathologies and disorders of the like. The method includes contacting a test compound with a MG53 polypeptide and determining if the test compound binds to said MG53 polypeptide. Binding of the test compound to the MG53 polypeptide indicates the test compound is a modulator of activity, or of latency or predisposition to the aforementioned disorders or syndromes.

Also within the scope of the invention is a method for screening for a modulator of activity, or of latency or predisposition to disorders or syndromes including, e.g., the diseases and disorders disclosed above and/or other pathologies and disorders of the like by administering a test compound to a test animal at increased risk for the aforementioned disorders or syndromes. The test animal expresses a recombinant polypeptide encoded by a MG53 nucleic acid. Expression or activity of MG53 polypeptide is then measured in the test animal, as is expression or activity of the protein in a control animal which recombinantly-expresses MG53 polypeptide and is not at increased risk for the disorder or syndrome. Next, the expression of MG53 polypeptide in both the test animal and the control animal is compared. A change in the activity of MG53 polypeptide in the test animal relative to the control animal indicates the test compound is a modulator of latency of the disorder or syndrome.

In yet another aspect, the invention includes a method for determining the presence of or predisposition to a disease associated with altered levels of a MG53 polypeptide, a MG53 nucleic acid, or both, in a subject (e.g., a human subject). The method includes measuring the amount of the MG53 polypeptide in a test sample from the subject and comparing the amount of the polypeptide in the test sample to the amount of the MG53 polypeptide present in a control sample. An alteration in the level of the MG53 polypeptide in the test sample as compared to the control sample indicates the presence of or predisposition to a disease in the subject. Preferably, the predisposition includes, e.g., the diseases and disorders disclosed above and/or other pathologies and disorders of the like. Also, the expression levels of the new polypeptides of the invention can be used in a method to screen for various disorders as well as to determine the stage of particular disorders.

In a further aspect, the invention includes a method of treating or preventing a pathological condition associated with a disorder in a mammal by administering to the subject a MG53 polypeptide, a MG53 nucleic acid, or a MG53-specific antibody to a subject (e.g., a human subject), in an amount sufficient to alleviate or prevent the pathological condition. In preferred embodiments, the disorder, includes, e.g., the diseases and disorders disclosed above and/or other pathologies and disorders of the like.

In yet another aspect, the invention can be used in a method to identity the cellular receptors and downstream effectors of the invention by any one of a number of techniques commonly employed in the art. These include but are not limited to the two-hybrid system, affinity purification, co-precipitation with antibodies or other specific-interacting molecules.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

As used herein, the term "MG53 antagonist" or "antagonist of MG53" is used generally to refer to an agent capable of direct or indirect inhibition of MG53 expression, translation, and/or activity. Also, as used herein "MG53 receptor" relates generally to any protein or fragment thereof capable of undergoing binding to a MG53 protein.

As used herein, the term "caveolin antagonist" or "antagonist of caveolin" is used generally to refer to an agent capable of direct or indirect inhibition of caveolin expression, translation, and/or activity. Also, as used herein "caveolin receptor" relates generally to any protein or fragment thereof capable of undergoing binding to a caveolin protein.

In certain aspects, the modulation of MG53 activity is accomplished by, for example, the use of or modulation of MG53 binding partners, i.e., factors that bind to MG53 and neutralize its biological activities, such as neutralizing anti-MG53, MG53 receptors (for example, or caveolin-3), MG53 receptor fragments, and MG53 receptor analogs; the use of MG53-receptor antagonists, such as anti-caveolin-3 antibodies, pseudopeptides, peptide analogs or peptidomimetics that bind and disrupt the MG53-receptor interaction; small molecules that inhibit MG53 activity or intermolecular interactions, or alter the normal configuration of MG53, or inhibit productive MG53/MG53-receptor binding; or the use of nucleotide sequences derived from MG53 gene and/or MG53 receptor gene, including coding, non-coding, and/or regulatory sequences to prevent or reduce MG53 expression by, for example, antisense, ribozyme, and/or triple helix approaches.

In another aspect, the present invention features a nucleic acid molecule, such as a decoy RNA, dsRNA, siRNA, shRNA, micro RNA, aptamers, antisense nucleic acid molecules, which down regulates expression of a sequence encoding MG53 or a MG53 receptor, for example, caveolin-3. In an embodiment, a nucleic acid molecule of the invention is adapted to treat and/or prevent tissue damage and promote tissue repair. In another embodiment, a nucleic acid molecule of the invention has an endonuclease activity or is a component of a nuclease complex, and cleaves RNA having a MG53 or a MG53 receptor nucleic acid sequence.

In one embodiment, a nucleic acid molecule of the invention comprises between 12 and 100 bases complementary to RNA having a MG53 or a MG53 receptor nucleic acid sequence. In another embodiment, a nucleic acid molecule of the invention comprises between 14 and 24 bases complementary to RNA having a MG53 or a MG53 receptor nucleic acid sequence. In any embodiment described herein, the nucleic acid molecule can be synthesized chemically according to methods well known in the art.

In another aspect the present invention provides a kit comprising a suitable container, the active agent capable of inhibiting MG53 activity, expression or binding in a pharmaceutically acceptable form disposed therein, and instructions for its use.

In another aspect, the invention relates to a method for diagnosing or monitoring disorder or disease or progression comprising detecting for the presence of a nucleotide polymorphism in the MG53 or a MG53 receptor structural gene associated with the disease, through the detection of the expression level of a MG53 or a MG53 receptor gene or protein or both. Polymorphisms have been identified that correlate with disease severity. (See, Zhong et al., Simultaneous detection of microsatellite repeats and SNPs in the macrophage migration inhibitory factor (MG53) gene by thin-film biosensor chips and application to rural field studies. *Nucleic Acids Res.* 2005 Aug. 2; 33(13):e121; Donn et al., A functional promoter haplotype of macrophage migration inhibitory factor is linked and associated with juvenile idiopathic arthritis. *Arthritis Rheum.* 2004 May; 50(5):1604-10; all of which are incorporated herein by reference in their entirety for all purposes.). As used herein, "MG53 or MG53 receptor gene" or "MG53 or MG53 receptor structural gene" may include the 5' UTR, 3' UTR, promoter sequences, enhancer sequences, intronic and exonic DNA of the MG53 or MG53 receptor gene as well as the MG53 or MG53 receptor gene mRNA or cDNA sequence.

As one of ordinary skill will comprehend, the MG53 or MG53 receptor gene polymorphisms associated with tissue repair disorders, and hence useful as diagnostic markers according to the methods of the invention may appear in any of the previously named nucleic acid regions. Techniques for the identification and monitoring of polymorphisms are known in the art and are discussed in detail in U.S. Pat. No. 6,905,827 to Wohlgemuth, which is incorporated herein by reference in its entirety for all purposes.

Certain aspects of the invention encompass methods of detecting gene expression or polymorphisms with one or more DNA molecules wherein the one or more DNA molecules has a nucleotide sequence which detects expression of a gene corresponding to the oligonucleotides depicted in the Sequence Listing. In one format, the oligonucleotide detects expression of a gene that is differentially expressed. The gene expression system may be a candidate library, a diagnostic agent, a diagnostic oligonucleotide set or a diagnostic probe set. The DNA molecules may be genomic DNA, RNA, protein nucleic acid (PNA), cDNA or synthetic oligonucleotides. Following the procedures taught herein, one can identify sequences of interest for analyzing gene expression or polymorphisms. Such sequences may be predictive of a disease state.

Diagnostic Oligonucleotides of the Invention

As used herein, the term "oligonucleotide molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

In certain aspects, the invention relates to diagnostic oligonucleotides and diagnostic oligonucleotide set(s), for which a correlation exists between the health status of an individual, and the individual's expression of RNA or protein products corresponding to the nucleotide sequence. In some instances, only one oligonucleotide is necessary for such detection. Members of a diagnostic oligonucleotide set may be identified by any means capable of detecting expression or a polymorphism of RNA or protein products, including but not limited to differential expression screening, PCR, RT-PCR, SAGE analysis, high-throughput sequencing, microarrays, liquid or other arrays, protein-based methods (e.g., western blotting, proteomics, mass-spectrometry, and other methods described herein), and data mining methods, as further described herein.

In the context of the invention, nucleic acids and/or proteins are manipulated according to well known molecular biology techniques. Detailed protocols for numerous such procedures are described in, e.g., in Ausubel et al. Current Protocols in Molecular Biology (supplemented through 2000) John Wiley & Sons, New York ("Ausubel"); Sambrook et al. Molecular Cloning—A Laboratory Manual (2nd Ed.), Vol. 1-3, Cold Spring Harbor Laboratory, Cold Spring Harbor, N.Y., 1989 ("Sambrook"), and Berger and Kimmel Guide to Molecular Cloning Techniques, Methods in Enzymology volume 152 Academic Press, Inc., San Diego, Calif. ("Berger").

Genotyping

In addition to, or in conjunction with the correlation of expression profiles and clinical data, it is often desirable to correlate expression patterns with the subject's genotype at one or more genetic loci or to correlate both expression profiles and genetic loci data with clinical data. The selected loci can be, for example, chromosomal loci corresponding to one or more member of the candidate library, polymorphic alleles for marker loci, or alternative disease related loci (not contributing to the candidate library) known to be, or putatively associated with, a disease (or disease criterion). Indeed, it will be appreciated, that where a (polymorphic) allele at a locus is linked to a disease (or to a predisposition to a disease), the presence of the allele can itself be a disease criterion.

Numerous well known methods exist for evaluating the genotype of an individual, including southern analysis, restriction fragment length polymorphism (RFLP) analysis, polymerase chain reaction (PCR), amplification length polymorphism (AFLP) analysis, single stranded conformation polymorphism (SSCP) analysis, single nucleotide polymorphism (SNP) analysis (e.g., via PCR, Taqman or molecular beacons), among many other useful methods. Many such procedures are readily adaptable to high throughput and/or automated (or semi-automated) sample preparation and analysis methods. Most, can be performed on nucleic acid samples recovered via simple procedures from the same sample as yielded the material for expression profiling. Exemplary techniques are described in, e.g., Sambrook, and Ausubel, supra.

The invention also features nucleic acid molecules, for example enzymatic nucleic acid molecules, antisense nucleic acid molecules, decoys, double stranded RNA, triplex oligonucleotides, and/or aptamers, and methods to modulate gene expression of, for example, genes encoding a MG53 protein, a MG53 protein or MG53 receptor binding protein or a MG53 receptor protein. In particular, the instant invention features nucleic-acid based molecules and methods to modulate the expression of a MG53 protein or MG53 receptor protein.

The invention features one or more enzymatic nucleic acid-based molecules and methods that independently or in combination modulate the expression of gene(s) encoding a MG53 protein, a MG53 protein or MG53 receptor binding protein, and/or a MG53 receptor protein, for example, caveolin-3.

The description below of the various aspects and embodiments is provided with reference to the exemplary MG53 and MG53 receptor genes. However, the various aspects and embodiments are also directed to genes which encode homologs, orthologs, and paralogs of other MG53 proteins, MG53 binding proteins, and MMG53 receptor genes and include all isoforms, splice variants, and polymorphisms. Those additional genes can be analyzed for target sites using the methods described for MG53 proteins, MG53 binding proteins, and MG53 receptor genes. Thus, the inhibition and the effects of such inhibition of the other genes can be performed as described herein.

By "down-regulate" it is meant that the expression of the gene, or level of RNAs or equivalent RNAs encoding one or more proteins, or activity of one or more proteins, such as MG53 and MG53 receptor genes, is reduced below that observed in the absence of the nucleic acid molecules of the invention. In one embodiment, inhibition or down-regulation with enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of MG53 proteins, MG53 binding proteins, and MG53 receptor genes with the nucleic acid molecule of the instant invention is greater in the presence of the nucleic acid molecule than in its absence.

By "up-regulate" is meant that the expression of the gene, or level of RNAs or equivalent RNAs encoding one or more protein subunits, or activity of one or more protein subunits, such as MG53 proteins, MG53 binding proteins, and MG53 receptor genes, is greater than that observed in the absence of the nucleic acid molecules of the invention. For example, the expression of a gene, such as MG53 proteins, MG53 binding proteins, and MG53 receptor genes, can be increased in order to treat, prevent, ameliorate, or modulate a pathological condition caused or exacerbated by an absence or low level of gene expression. In one embodiment the invention relates to a method for treating or preventing bladder over activity by up-regulating the expression, release, and/or activity of a MG53 proteins, MG53 binding proteins, and MG53 receptor genes.

By "modulate" is meant that the expression of the gene, or level of RNAs or equivalent RNAs encoding one or more proteins, or activity of one or more proteins is up-regulated or down-regulated, such that the expression, level, or activity is greater than or less than that observed in the absence of the nucleic acid molecules of the invention.

By "gene" it is meant a nucleic acid that encodes RNA, for example, nucleic acid sequences including but not limited to a segment encoding a polypeptide.

"Complementarity" refers to the ability of a nucleic acid to form hydrogen bond(s) with another RNA sequence by either traditional Watson-Crick or other non-traditional types.

By "RNA" is meant a molecule comprising at least one ribonucleotide residue. By "ribonucleotide" or "2'-OH" is meant a nucleotide with a hydroxyl group at the 2' position of a D-ribo-furanose moiety.

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra).

By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

By "enzymatic nucleic acid molecule" it is meant a nucleic acid molecule which has complementarity in a substrate binding region to a specified gene target, and also has or mediates an enzymatic activity which is active to specifically cleave target RNA. That is, the enzymatic nucleic acid molecule is able to intermolecularly cleave RNA, alone or as a component of an enzymatic complex, and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50-75% can also be useful in this invention (see for example Werner and Uhlenbeck, 1995, Nucleic Acids Research, 23, 2092 2096; Hammann et al., 1999, Antisense and Nucleic Acid Drug Dev., 9, 25 31). The nucleic acids can be modified at the base, sugar, and/or phosphate groups. The term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, siRNA, micro RNA, short hairpin RNA, endoribonuclease, RNA-induced silencing complexes, endonuclease, minizyme, leadzyme, oligozyme or DNA enzyme. All of these terminologies describe nucleic acid molecules with enzymatic activity.

The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

Several varieties of enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. Thus, a single ribozyme molecule is able to cleave many molecules of target RNA. In addition, the ribozyme is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

By "nucleic acid molecule" as used herein is meant a molecule having nucleotides. The nucleic acid can be single, double, or multiple stranded and can comprise modified or unmodified nucleotides or non-nucleotides or various mixtures and combinations thereof.

By "equivalent" or "related" RNA to MG53 proteins, MG53 binding proteins, and MG53 receptor genes is meant to include those naturally occurring -RNA molecules having homology (partial or complete) to MG53 proteins, MG53 binding proteins, and MG53 receptor genes encoding for proteins with similar function as MG53 proteins, MG53 binding proteins, and MG53 receptor proteins in various organisms, including human, rodent, primate, rabbit, pig, protozoans, fungi, plants, and other microorganisms and parasites. The equivalent RNA sequence also includes in addition to the coding region, regions such as 5'-untranslated region, 3'-untranslated region, introns, intron-exon junction and the like. By "homology" is meant the nucleotide sequence of two or more nucleic acid molecules is partially or completely identical. In certain embodiments the homolgous nucleic acid has 30%, 40%, 50%, 60%, 70%, 80%, 90%, or 95% homology to MG53, MG53 binding protein, and/or MG53 receptor gene.

By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop or hairpin, and/or an antisense molecule can bind such that the antisense molecule forms a loop or hairpin. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol, 40, 1-49, which are incorporated herein by reference in their entirety. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

Long double-stranded RNAs (dsRNAs; typically >200 nt) can be used to silence the expression of target genes in a variety of organisms and cell types (e.g., worms, fruit flies, and plants). Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. In mammalian cells, introduction of long dsRNA (>30 nt) initiates a potent antiviral response, exemplified by nonspecific inhibition of protein synthesis and RNA degradation. The mammalian antiviral response can be bypassed, however, by the introduction or expression of siRNAs.

Injection and transfection of dsRNA into cells and organisms has been the main method of delivery of siRNA. And while the silencing effect lasts for several days and does appear to be transferred to daughter cells, it does eventually diminish. Recently, however, a number of groups have developed expression vectors to continually express siRNAs in transiently and stably transfected mammalian cells. (See, e.g., Brummelkamp T R, Bernards R, and Agami R. (2002). A system for stable expression of short interfering RNAs in mammalian cells. *Science* 296:550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev. 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052, which are herein incorporated by reference in their entirety).

Some vectors have been engineered to express small hairpin RNAs (shRNAs), which get processed in vivo into siRNAs-like molecules capable of carrying out gene-specific silencing. The vectors contain the shRNA sequence between a polymerase III (pol III) promoter (e.g., U6 or H1 promoters) and a 4-5 thymidine transcription termination site. The transcript is terminated at position 2 of the termination site (pol III transcripts naturally lack poly(A) tails) and then folds into a stem-loop structure with 3' UU-overhangs. The ends of the shRNAs are processed in vivo, converting the shRNAs into ~21 nt siRNA-like molecules, which in turn initiate RNAi. This latter finding correlates with recent experiments in *C. elegans, Drosophila*, plants and Trypanosomes, where RNAi has been induced by an RNA molecule that folds into a stem-loop structure. The use of siRNA vectors and expression systems is known and are commercially available from Ambion, Inc.® (Austin, Tex.), Lentigen, Inc. (Baltimore, Md.), Panomics (Fremont, Calif.), and Sigma-Aldrich (St. Louis, Mo.).

In another aspect of the invention, enzymatic nucleic acid molecules or antisense molecules that interact with target RNA molecules, and down-regulate MG53, MG53 binding proteins, and/or a MG53 receptor gene activity are expressed from transcription units inserted into DNA or RNA vectors. The recombinant vectors are preferably DNA plasmids or viral vectors. Enzymatic nucleic acid molecule or antisense expressing viral vectors can be constructed based on, but not limited to, lenti virus, cytomegalovirus, adeno-associated virus, retrovirus, adenovirus, or alphavirus. Preferably, the recombinant vectors capable of expressing the enzymatic nucleic acid molecules or antisense are delivered, and persist in target cells. Alternatively, viral vectors can be used that provide for expression of enzymatic nucleic acid molecules or antisense. Such vectors can be repeatedly administered as necessary. Once expressed, the enzymatic nucleic acid molecules or antisense bind to the target RNA and down-regulate its function or expression. Delivery of enzymatic nucleic acid molecule or antisense expressing vectors can be systemic, such as by intravenous or intramuscular administration, by administration to target cells explanted from the patient or subject followed by reintroduction into the patient or subject, or by any other means that would allow for introduction into the desired target cell. Antisense DNA can be expressed via the use of a single stranded DNA intracellular expression vector.

By "vectors" is meant any nucleic acid-based technique used to deliver a desired nucleic acid, for example, bacterial plasmid, viral nucleic acid, HAC, BAC, and the like.

The nucleic acid molecules of the instant invention, individually, or in combination or in conjunction with other drugs, can be used to treat diseases or conditions discussed above. For example, the subject can be treated, or other appropriate cells can be treated, as is evident to those skilled in the art, individually or in combination with one or more drugs under conditions suitable for the treatment.

The use of specially designed vector constructs for inducing RNA interference has numerous advantages over oligonucleotide-based techniques. The most significant advantages are stability, and induced transcription via inducible promoters. Promoter regions in the vector ensure that shRNA transcripts are constantly expressed, maintaining cellular levels at all times. Thus, the duration of the effect is not as transient as with injected RNA, which usually lasts no longer than a few days. And by using expression constructs instead of oligo injection, it is possible to perform multi-generational studies of gene knockdown because the vector can become a permanent fixture in the cell line.

By "triplex forming oligonucleotides" or "triplex oligonucleotide" is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206).

By "double stranded RNA" or "dsRNA" is meant a double stranded RNA that matches a predetermined gene sequence that is capable of activating cellular enzymes that degrade the corresponding messenger RNA transcripts of the gene. These dsRNAs are referred to as short intervening RNA (siRNA) and can be used to inhibit gene expression. see for example Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.

In one embodiment of the present invention, a nucleic acid molecule of the instant invention can be between about 10 and 100 nucleotides in length. For example, enzymatic nucleic acid molecules of the invention are preferably between about 15 and 50 nucleotides in length, more preferably between about 25 and 40 nucleotides in length (for example see Jarvis et al., 1996, J. Biol. Chem., 271, 29107 29112). Exemplary antisense molecules of the invention are preferably between about 15 and 75 nucleotides in length, more preferably between about 20 and 35 nucleotides in length (see for example Woolf et al., 1992, PNAS., 89, 7305 7309; Milner et al., 1997, Nature Biotechnology, 15, 537 541). Exemplary triplex forming oligonucleotide molecules of the invention are preferably between about 10 and 40 nucleotides in length, more preferably between about 12 and 25 nucleotides in length (see for example Maher et al, 1990, Biochemistry, 29, 8820 8826; Strobel and Dervan, 1990, Science, 249, 73 75). Those skilled in the art will recognize that all that is required is that the nucleic acid molecule be of sufficient length and suitable conformation for the nucleic acid molecule to interact with its target and/or catalyze a reaction contemplated herein. The length of the nucleic acid molecules of the instant invention are not limiting within the general limits stated. Preferably, a nucleic acid molecule that modulates, for example, down-regulates MG53, MG53 binding protein, and/or a MG53 receptor gene expression comprises between 12 and 100 bases complementary to a RNA molecule of a MG53 gene, a MG53 binding protein gene, and/or a MG53 receptor gene.

The invention provides a method for producing a class of nucleic acid-based gene modulating agents which exhibit a high degree of specificity for the RNA of a desired target. For example, the enzymatic nucleic acid molecule is preferably targeted to a highly conserved sequence region of target RNAs encoding a MG53, MG53 binding protein, and/or a MG53 receptor gene such that specific treatment of a disease or condition can be provided with either one or several nucleic acid molecules of the invention. Such nucleic acid molecules can be delivered exogenously to specific tissue or cellular targets as required. Alternatively, the nucleic acid molecules (e.g., ribozymes and antisense) can be expressed from DNA and/or RNA vectors that are delivered to specific cells.

As used in herein "cell" is used in its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The nucleic acid-based inhibitors of the invention are added directly, or can be complexed with cationic lipids, packaged within liposomes, or otherwise delivered to target cells or tissues. The nucleic acid or nucleic acid complexes can be locally administered to relevant tissues in vitro, ex vivo, or in vivo through injection or infusion pump, with or without their incorporation in biopolymers.

In another embodiment, the invention features an enzymatic nucleic acid molecule having one or more non-nucleotide moieties, and having enzymatic activity to cleave an RNA or DNA molecule.

In a further embodiment, the described nucleic acid molecules, such as antisense or ribozymes, can be used in combination with other known treatments to treat conditions or diseases discussed above. For example, the described molecules can be used in combination with one or more known therapeutic agents.

Antisense molecules can be modified or unmodified RNA, DNA, or mixed polymer oligonucleotides and primarily function by specifically binding to matching sequences resulting in inhibition of peptide synthesis (Wu-Pong, November 1994, BioPharm, 20-33). The antisense oligonucleotide binds to target RNA by Watson Crick base-pairing and blocks gene expression by preventing ribosomal translation of the bound sequences either by steric blocking or by activating RNase H enzyme. Antisense molecules can also alter protein synthesis by interfering with RNA processing or transport from the nucleus into the cytoplasm (Mukhopadhyay & Roth, 1996, Crit. Rev. in Oncogenesis 7, 151-190).

In addition, binding of single stranded DNA to RNA can result in nuclease degradation of the heteroduplex (Wu-Pong, supra; Crooke, supra). To date, the only backbone modified DNA chemistry which acts as substrates for RNase H are phosphorothioates, phosphorodithioates, and borontrifluoridates. Recently it has been reported that 2'-arabino and 2'-fluoro-arabino-containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526; Thompson et al., International PCT Publication No. WO 99/54459; Hartmann et al., U.S. Ser. No. 60/101,174 which was filed on Sep. 21, 1998) all of these are incorporated by reference herein in their entirety.

Several varieties of enzymatic RNAs are presently known. In addition, several in vitro selection (evolution) strategies (Orgel, 1979, Proc. R. Soc. London, B 205, 435) have been used to evolve new nucleic acid catalysts capable of catalyzing cleavage and ligation of phosphodiester linkages (Joyce, 1989, Gene, 82, 83 87; Beaudry et al., 1992, Science 257, 635-641; Joyce, 1992, Scientific American 267, 90-97; Breaker et al., 1994, TIBTECH 12, 268; Bartel et al., 1993, Science 261:1411-1418; Szostak, 1993, TIBS 17, 89-93; Kumar et al., 1995, FASEB J., 9, 1183; Breaker, 1996, Curr. Op. Biotech., 7, 442; Santoro et al., 1997, Proc. Natl. Acad. Sci., 94, 4262; Tang et al., 1997, RNA 3, 914; Nakacane & Eckstein, 1994, supra; Long & Uhlenbeck, 1994, supra; Ishizaka et al., 1995, supra; Vaish et al., 1997, Biochemistry 36, 6495; all of these are incorporated by reference herein). Each can catalyze a series of reactions including the hydrolysis of phosphodiester bonds in trans (and thus can cleave other RNA molecules) under physiological conditions.

The enzymatic nature of an enzymatic nucleic acid molecule can allow the concentration of enzymatic nucleic acid molecule necessary to affect a therapeutic treatment to be lower. This reflects the ability of the enzymatic nucleic acid molecule to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to greatly attenuate the catalytic activity of a enzymatic nucleic acid molecule.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieve efficient cleavage in vitro (Zaug et al., 324, Nature 429 1986; Uhlenbeck, 1987 Nature 328, 596; Kim et al., 84 Proc. Natl. Acad. Sci. USA 8788, 1987; Dreyfus, 1988, Einstein Quart. J. Bio. Med., 6, 92; Haseloff and Gerlach, 334 Nature 585, 1988; Cech, 260 JAMA 3030, 1988; and Jefferies et al., 17 Nucleic Acids Research 1371, 1989; Santoro et al., 1997 supra).

Because of their sequence specificity, trans-cleaving enzymatic nucleic acid molecules can be used as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited (Warashina et al., 1999, Chemistry and Biology, 6, 237-250).

Enzymatic nucleic acid molecules of the invention that are allosterically regulated ("allozymes") can be used to modulate MG53, MG53 binding proteins, and/or MG53 receptor gene expression. These allosteric enzymatic nucleic acids or allozymes (see for example George et al, U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842) are designed to respond to a signaling agent, which in turn modulates the activity of the enzymatic nucleic acid molecule and modulates expression of MG53, MG53 binding proteins, and/or MG53 receptor gene. In response to interaction with a predetermined signaling agent, the allosteric enzymatic nucleic acid molecule's activity is activated or inhibited such that the expression of a particular target is selectively down-regulated. The target can comprise MG53, MG53 binding proteins, and/or MG53 receptor gene.

Oligonucleotides (eg; antisense, GeneBlocs) are synthesized using protocols known in the art as described in Caruthers et al., 1992, Methods in Enzymology 211, 3 19, Thompson et al., International PCT Publication No. WO 99/54459, Wincott et al., 1995, Nucleic Acids Res. 23, 2677 2684, Wincott et al., 1997, Methods Mol. Bio., 74, 59, Brennan et al, 1998, Biotechnol Bioeng., 61, 33 45, and Brennan, U.S. Pat. No. 6,001,311. All of these references are incorporated herein by reference. In a non-limiting example, small scale syntheses are conducted on a 394 Applied Biosystems, Inc. synthesizer. Alternatively, the nucleic acid molecules of the present invention can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, TIBS 17, 34; Usman et al., 1994, Nucleic Acids Symp. Ser. 31, 163).

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Nucleic acid molecules are preferably resistant to nucleases in order to function as effective intracellular therapeutic agents. Improvements in the chemical synthesis of RNA and DNA (Wincott et al., 1995 Nucleic Acids Res. 23, 2677; Caruthers et al., 1992, Methods in Enzymology 211, 3-19 (incorporated by reference herein) have expanded the ability to modify nucleic acid molecules by introducing nucleotide modifications to enhance their nuclease stability as described above. The use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules and/or other chemical or biological molecules). The treatment of subjects with nucleic acid molecules can also include combinations of different types of nucleic acid molecules.

In one embodiment, nucleic acid catalysts having chemical modifications that maintain or enhance enzymatic activity are provided. Such nucleic acids are also generally more resistant to nucleases than unmodified nucleic acid.

In one embodiment, the invention features modified enzymatic nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, Nucleic Acid Analogues: Synthesis and Properties, in Modern Synthetic Methods, VCH, 331 417, and Mesmaeker et al., 1994, Novel Backbone Replacements for Oligonucleotides, in Carbohydrate Modifications in Antisense Research, ACS, 24 39. These references are hereby incorporated by reference herein. Various modifications to nucleic acid (e.g., antisense and ribozyme) structure can be made to enhance the utility of these molecules. For example, such modifications can enhance shelf-life, half-life in vitro, bioavailability, stability, and ease of introduction of such oligonucleotides to the target site, including e.g., enhancing penetration of cellular membranes and conferring the ability to recognize and bind to targeted cells.

Administration of Nucleic Acid Molecules. Methods for the delivery of nucleic acid molecules are described in Akhtar et al., 1992, Trends Cell Bio., 2, 139; and Delivery Strategies for Antisense Oligonucleotide Therapeutics, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by a incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. For a comprehensive review on drug delivery strategies including CNS delivery, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400.

The molecules of the instant invention can be used as pharmaceutical agents. Pharmaceutical agents prevent, inhibit the occurrence, or treat (alleviate a symptom to some extent, preferably all of the symptoms) a disease state in a subject.

The negatively charged polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose or pharmaceutically effective amount is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the negatively charged polymer.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono-or diglycerides. In addition, fatty acids such as oleic acid find use in the preparation of injectables.

Nucleic acid molecules of the invention can also be administered in the form of suppositories, e.g., for rectal administration of the drug or via a catheter directly to the bladder itself. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The amount of active ingredient that can be combined with the carrier materials to produce a single dosage form varies depending upon the host treated and the particular mode of administration. Dosage unit forms generally contain between from about 1 mg to about 1000 mg of an active ingredient.

It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The composition can also be administered to a subject in combination with other therapeutic compounds to increase the overall therapeutic effect. The use of multiple compounds to treat an indication can increase the beneficial effects while reducing the presence of side effects.

Alternatively, certain of the nucleic acid molecules of the instant invention can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591 5; Kashani-Sabet et al., 1992, Antisense Res. Dev., 2, 3 15; propulic et al., 1992, J. Virol., 66, 1432 41; Weerasinghe et al., 1991, J. Virol., 65, 5531 4; Ojwang et al., 1992, Proc. Natl. Acad. Sci. USA, 89, 10802 6; Chen et al., 1992, Nucleic Acids Res., 20, 4581 9; Sarver et al., 1990 Science, 247, 1222 1225; Thompson et al, 1995, Nucleic Acids Res., 23, 2259; Good et al., 1997, Gene Therapy, 4, 45; all of these references are hereby incorporated in their totalities by reference herein). Those skilled in the art realize that any nucleic acid can be expressed in eukaryotic cells from the appropriate DNA/RNA vector.

In one aspect the invention features an expression vector comprising a nucleic acid sequence encoding at least one of the nucleic acid molecules of the instant invention. The nucleic acid sequence encoding the nucleic acid molecule of the instant invention is operably linked in a manner which allows expression of that nucleic acid molecule.

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743 7; Gao and Huang 1993, Nucleic Acids Res., 21, 2867 72; Lieber et al., 1993, Methods Enzymol., 217, 47 66; Zhou et al., 1990, Mol. Cell. Biol., 10, 4529 37). All of these references are incorporated by reference herein. Several investigators have demonstrated that nucleic acid molecules, such as ribozymes expressed from such promoters can function in mammalian cells (e.g. Kashani-Sabet et al., 1992, Antisense Res. Dev., 2, 3 15; Ojwang et al., 1992, Proc. Natl. Acad. Sci. USA, 89, 10802 6; Chen et al, 1992, Nucleic Acids Res., 20, 4581 9; Yu et al., 1993, Proc. Natl. Acad. Sci. USA, 90, 6340 4; L'Huillier et al., 1992, EMBO J., 11, 4411 8; Lisziewicz et al., 1993, Proc. Natl. Acad. Sci. U.S.A, 90, 8000 4; Thompson et al., 1995, Nucleic Acids Res., 23, 2259; Sullenger & Cech, 1993, Science, 262, 1566).

In another aspect the invention features an expression vector comprising nucleic acid sequence encoding at least one of the nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule.

A further object of the present invention is to provide a kit comprising a suitable container, the therapeutic of the invention in a pharmaceutically acceptable form disposed therein, and instructions for its use.

In another embodiment, an isolated nucleic acid molecule of the invention comprises a nucleic acid molecule that is a complement of the nucleotide sequence of MG53, a MG53 binding protein, and/or a MG53 receptor. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect.

As used herein, "fragments" are defined as sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence.

The term "host cell" includes a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

"Derivatives" are compositions formed from the native compounds either directly, by modification, or by partial substitution.

"Analogs" are nucleic acid sequences or amino acid sequences that have a structure similar to, but not identical to, the native compound.

Derivatives or analogs of the nucleic acids or proteins of the invention include, but are not limited to, molecules comprising regions that are substantially homologous to the nucleic acids or proteins of the invention, in various embodiments, by at least about 30%, 40%, 50%, 60%, 70%, 80%, 90%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30% at the primary amino acid structure level, it is concluded that they share a common ancestor. For purposes of the present invention, genes are homologous if the nucleic acid sequences are sufficiently similar to allow recombination and/or hybridization under low stringency conditions.

As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA.

Furthermore, one of ordinary skill will recognize that "conservative mutations" also include the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing Methionine (M), Cysteine (C). In addition, sequences that differ by conservative variations are generally homologous.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) C&EN 36-47; Lueng, et al.

In yet another embodiment, a nucleic acid of the invention is expressed in mammalian cells using a mammalian expression vector. For suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

A polynucleotide can be a DNA molecule, a cDNA molecule, genomic DNA molecule, or an RNA molecule. A polynucleotide as DNA or RNA can include a sequence wherein T (thymidine) can also be U (uracil). If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process.

Transformation of a host cell with recombinant DNA may be carried out by conventional techniques as are well known to those skilled in the art. By "transformation" is meant a permanent or transient genetic change induced in a cell following incorporation of new DNA (i.e., DNA exogenous to the cell).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

In any of the embodiments, the nucleic acids encoding the MG53, MG53 binding protein, and/or MG53 receptor can be present as: one or more naked DNAs; one or more nucleic acids disposed in an appropriate expression vector and maintained episomally; one or more nucleic acids incorporated into the host cell's genome; a modified version of an endogenous gene encoding the components of the complex; one or more nucleic acids in combination with one or more regulatory nucleic acid sequences; or combinations thereof. The nucleic acid may optionally comprise a linker peptide or fusion protein component, for example, His-Tag, FLAG-Tag, fluorescent protein, GST, TAT, an antibody portion, a signal peptide, and the like, at the 5' end, the 3' end, or at any location within the ORF.

In a preferred embodiment, the nucleic acid of the invention comprises a polynucleotide encoding the soluble (i.e., the extracellular) portion of a MG53 receptor. Any of the embodiments described herein, can be achieved using standard molecular biological and genetic approaches well known to those of ordinary skill in the art.

Where the host is prokaryotic, such as $E.\ coli$, competent cells which are capable of DNA uptake can be prepared from cells harvested after exponential growth phase and subsequently treated by the $CaCl_2$ method by procedures well known in the art. Alternatively, $MgCl_2$, RbCl, liposome, or liposome-protein conjugate can be used. Transformation can also be performed after forming a protoplast of the host cell or by electroporation. These examples are not limiting on the present invention; numerous techniques exist for transfecting host cells that are well known by those of skill in the art and which are contemplated as being within the scope of the present invention.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. The eukaryotic cell may be a yeast cell (e.g., *Saccha-*

*romyces cerevisiae*) or may be a mammalian cell, including a human cell. For long-term, high-yield production of recombinant proteins, stable expression is preferred.

Polypeptides

By "MG53," "MG53 binding protein," and "MG53 receptor" proteins is meant, a peptide or protein comprising a full length MG53, MG53 binding protein or a MG53 receptor protein, domain, fusion protein, chimera, or fragment thereof.

In other embodiments, the invention pertains to isolated nucleic acid molecules that encode MG53, MG53 binding proteins, and/or MG53 receptor polypeptides, antibody polypeptides, or biologically active portions thereof. The polypeptides of the complex can be formed, for example, using a peptide synthesizer according to standard methods; or by expressing each polypeptide separately in a cell or cell extract, then isolating and purifying the polypeptide.

Antibodies

The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')2 fragments, and an Fab expression library. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids of MG53, MG53 binding protein, or MG53 receptor protein. In one embodiment, the peptide is located in a non-transmembrane domain of the polypeptide, e.g., in an extracellular or intracellular domain. An exemplary antibody or antibody fragment binds to an epitope that is accessible from the extracellular milieu and that alters the functionality of the protein. In certain embodiments, the present invention comprises antibodies that recognize and are specific for one or more epitopes of a MG53 protein, MG53 binding protein, and/or MG53 receptor protein, variants, portions and/or combinations thereof. In alternative embodiments antibodies of the invention may target and interfere with the MG53/MG53 receptor interaction to inhibit signaling.

The preparation of monoclonal antibodies is well known in the art; see for example, Harlow et al., Antibodies: A Laboratory Manual, page 726 (Cold Spring Harbor Pub. 1988). Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind to MG53, MG53 binding proteins, and/or MG53 receptor proteins or fragments thereof (as described in, e.g., Ladner et al. U.S. Pat. No. 5,223,409; Fuchs et al. (1991) Bio/Technology 9:1370-1372; Hay et al. (1992) Hum Antibod Hybridomas 3:81-85; Huse et al. (1989) Science 246:1275-1281; Clackson et al. (1991) Nature 352:624-628; Gram et al. (1992) PNAS 89:3576-3580.

Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855).

A therapeutically useful antibody to the components of the complex of the invention or the complex itself may be derived from a "humanized" monoclonal antibody. Humanized monoclonal antibodies are produced by transferring mouse complementarity determining regions from heavy and light variable chains of the mouse immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found in Jones et al., Nature 321: 522, 1986 and Singer et al., J. Immunol. 150: 2844, 1993. The antibodies can also be derived from human antibody fragments isolated from a combinatorial immunoglobulin library; see, for example, Barbas et al., Methods: A Companion to Methods in Enzymology 2, 119, 1991. In addition, chimeric antibodies can be obtained by splicing the genes from a mouse antibody molecule with appropriate antigen specificity together with genes from a human antibody molecule of appropriate biological specificity; see, for example, Takeda et al., Nature 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

In certain embodiments of the invention, at least one epitope encompassed by the antigenic peptide is a region of MG53, a MG53 binding protein, and/or a MG53 receptor that is located on the surface of the protein, e.g., a hydrophilic region. A hydrophobicity analysis of the protein sequence will indicate which regions of a polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824-3828; Kyte and Doolittle 1982, *J. Mol. Biol.* 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, *J. Mol. Biol.* 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology*, 10:779-783 (1992)); Lonberg et al. (*Nature*, 368: 856-859 (1994)); Morrison (*Nature*, 368:812-13 (1994)); Fishwild et al, (*Nature Biotechnology*, 14:845-51 (1996)); Neuberger (*Nature Biotechnology*, 14:826 (1996)); and Lonberg and Huszar (*Intern. Rev. Immunol.*, 13:65-93 (1995)).

Human antibodies may additionally be produced using transgenic nonhuman animals which are modified so as to produce fully human antibodies rather than the animal's endogenous antibodies in response to challenge by an antigen. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096.

Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., *Science* 246:1275-1281 (1989)) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) Fv fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537-539 (1983)). Because of the random assortment of immunoglobulin heavy and light chains, these hybridomas (quadromas) produce a potential mixture of ten different antibody molecules, of which only one has the correct bispecific structure. Similar procedures are disclosed in WO 93/08829, published May 13, 1993, and Traunecker et al., *EMBO J.*, 10:3655-3659 (1991).

Antibody variable domains with the desired binding specificities (antibody-antigen combining sites) can be fused to immunoglobulin constant domain sequences. For further details of generating bispecific antibodies see, for example, Suresh et al., *Methods in Enzymology,* 121:210 (1986); and Brennan et al., *Science* 229:81 (1985).

Additionally, Fab' fragments can be directly recovered from *E. coli* and chemically coupled to form bispecific antibodies. Shalaby et al., *J. Exp. Med.* 175:217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The "diabody" technology described by Hollinger et al., *Proc. Nall. Acad. Sci. USA* 90:6444-6448 (1993) has provided an alternative mechanism for making bispecific antibody fragments. Another strategy for making bispecific antibody fragments by the use of single-chain Fv (sFv) dimers has also been reported. See, Gruber et al., *J. Immunol.* 152:5368 (1994). Antibodies with more than two valencies are contemplated. For example, trispecific antibodies can be prepared. Tutt et al., *J. Immunol.* 147:60 (1991). Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a chemical agent, or a radioactive isotope (i.e., a radioconjugate). Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Immunoliposomes

The antibodies disclosed herein can also be formulated as immunoliposomes. Liposomes containing the antibody are prepared by methods known in the art, such as described in Epstein et al., *Proc. Natl. Acad. Sci. USA,* 82: 3688 (1985); Hwang et al., *Proc. Natl. Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide-interchange reaction.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 500 mg/kg body weight. Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., Fab or $F(ab)_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques intracavity, or transdermally, alone or with effector cells.

Preparations for administration of the therapeutic of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The compounds, nucleic acid molecules, polypeptides, and antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the therapeutic complex of the invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

A therapeutically effective dose refers to that amount of the therapeutic sufficient to result in amelioration or delay of symptoms. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Also disclosed according to the present invention is a kit or system utilizing any one of the methods, selection strategies, materials, or components described herein. Exemplary kits according to the present disclosure will optionally, additionally include instructions for performing methods or assays, packaging materials, one or more containers which contain an assay, a device or system components, or the like.

Additional objects and advantages of the present invention will be appreciated by one of ordinary skill in the art in light of the current description and examples of the preferred embodiments, and are expressly included within the scope of the present invention.

EXAMPLES

Discovery of MG53, a muscle specific TRIM family protein. MG53 was isolated using a previously established an immuno-proteomic approach that allows identification of novel proteins involved in myogenesis, $Ca^{2+}$ signaling and maintenance of membrane integrity in striated muscle cells. Briefly, this approach uses a monoclonal antibody library containing ~6500 clones that was generated from mice immunized with triad-enriched membranes from rabbit skeletal muscle. Antibodies of interest were selected based on the z-line staining patterns of striated muscle sections observed under an immunofluorescence microscope. The target-proteins were purified through antibody-affinity column, and partial amino acid sequences of the purified proteins were obtained. Based on the partial amino acid sequence, the complete cDNA coding for the target gene was isolated from a skeletal muscle cDNA library. Homologous gene screening was then used to search for the presence of different isoforms of the identified genes in other excitable tissues. Finally, transgenic or knockout mouse models were generated to study the in vivo physiological function of genes of interest.

Figure 3:
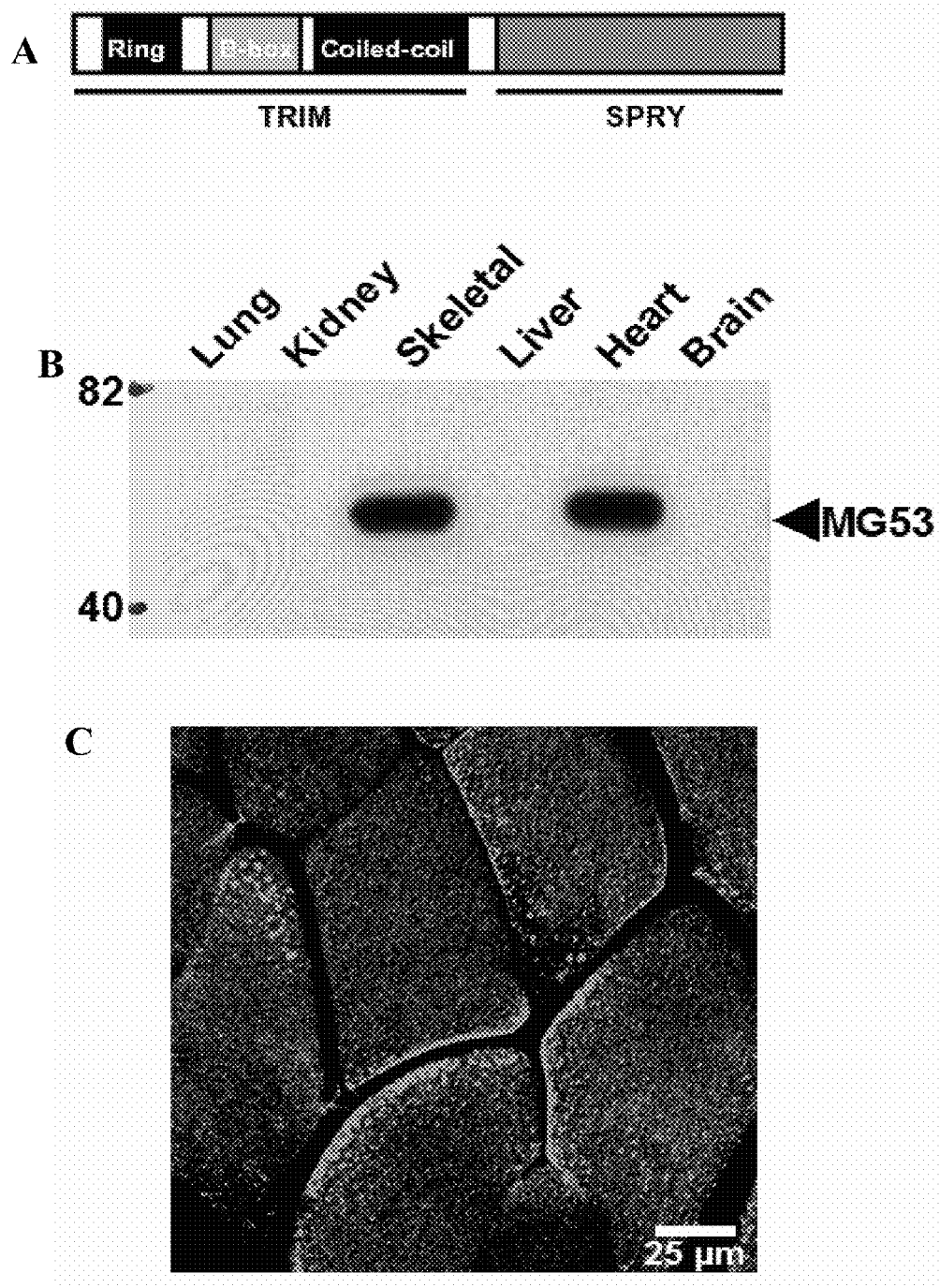
FIG. 3: MG53 contains unique TRIM and SPRY motifs and is predominantly expressed in muscle cells. A. Diagram of motif structure of MG53. From the results of cDNA cloning and homology searches, several motif sequences are detected in MG53 as shown. The sequences of rabbit and mouse MG53 cDNAs have been deposited in the databases under accession numbers AB231473 and AB231474, respectively. B. Western blot analysis shows the specific expression of MG53 in skeletal and cardiac muscles. Lysate (20 μg total protein per lane) from mouse tissues (lung, kidney, skeletal muscle, liver, heart, brain) were analyzed using anti-mouse MG53 polyclonal antibody. C. Immunofluorescence staining of longitudinal transverse sections from mouse skeletal muscle cells. Scale bar is 125 μm.

Screening of this immuno-proteomic library for muscle specific proteins led to the identification of an antigen recognized by mAb5259 with a molecular size of 53 kilodaltons (kDa) specifically with striated muscle tissues (FIG. 3B). The protein, "MG53", was partially purified from rabbit skeletal muscle by a mAb5259 immunoaffinity column and subjected to amino acid sequencing. Skeletal muscle cDNA library screening and genomic database searches identified the predicted amino acid sequences for MG53 and the corresponding mg53 gene on the human 16p11.2 locus. Northern blotting for the mg53 mRNA confirmed specific expression with skeletal and cardiac muscle (FIG. 3C). Domain homology analysis revealed that MG53 contains the prototypical tripartite motifs that include a Ring, B-box and Coiled-Coil (RBCC) moieties, as well as a SPRY domain at the carboxyl-terminus (FIGS. 1, 2, and 3A). The SPRY domain is a conserved sequence first observed in the ryanodine receptor $Ca^{2+}$ release channel in the sarcoplasmic reticulum of excitable cells. Of the approximately 60 TRIM family members so far identified in various mammalian genomes, 15 members carry a similar SPRY domain following the RBCC domain, and MG53 shows a conserved primary structure with these TRIM sub-family proteins.

Figure 4:
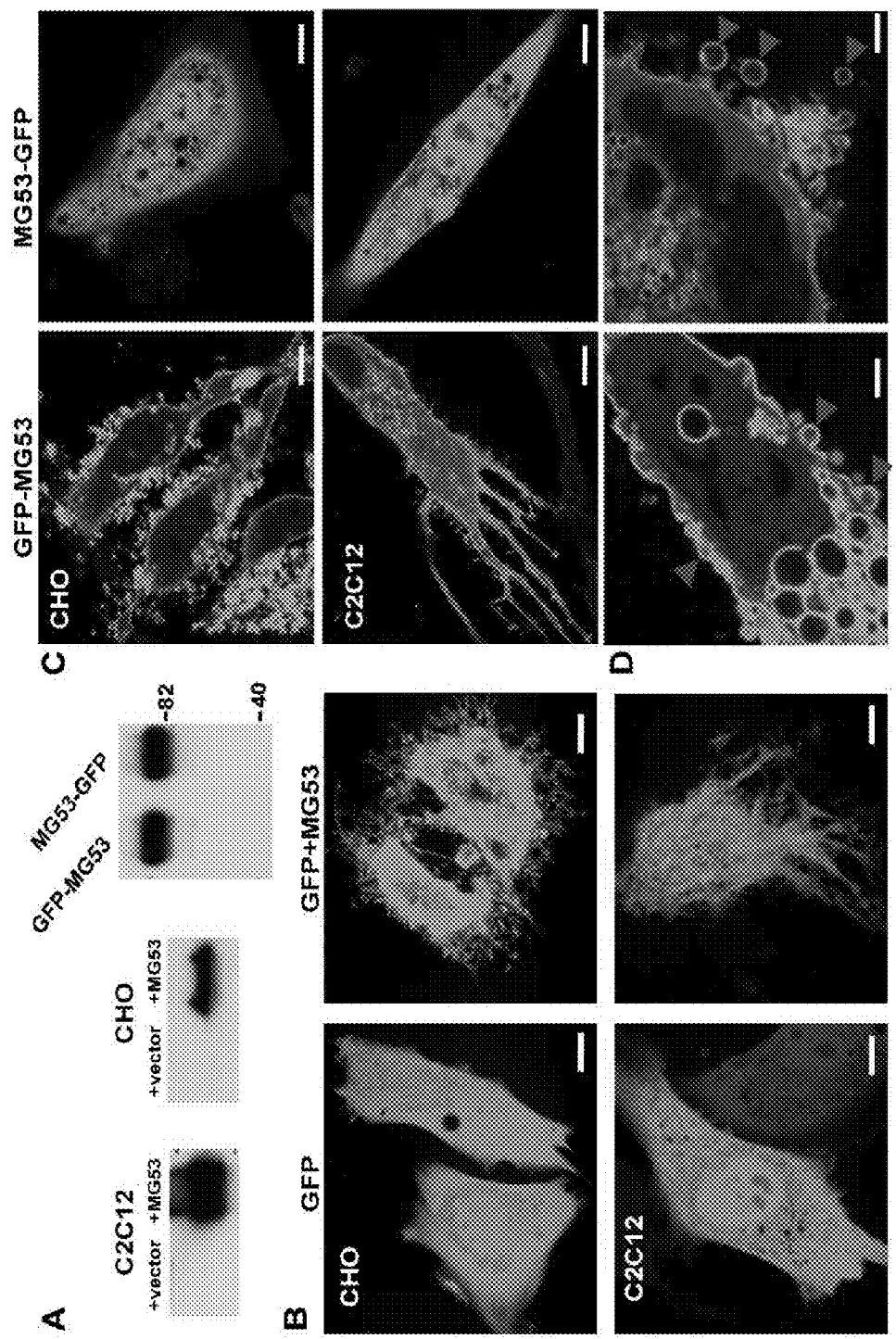
FIG. 4. Induction of filapodia-like structure with overexpression of MG53 in both muscle and non-muscle cells A. Western blot analysis shows the overexpression level of MG53 in C2C12 myoblasts (left panel) and CHO (middle panel) cells, and also GFP-MG53 and MG53-GFP (right panel) in C2C12 myoblasts (20 μg total protein per lane). B. Typical confocal images of CHO (upper panel) and C2C12 myoblasts (lower panel) transfected with GFP (left panel), or GFP+MG53 (right panel), revealing filapodia-like structures after overexpression of MG53. Scale bar is 5 μm. C. Confocal images of GFP-MG53 (left panel) and MG53-GFP (right panel) expressed in CHO cells (upper panel) and C2C12 (lower panel) myoblasts, revealing membrane targeting and intracellular vesicular distribution of MG53, as well as the appearance of filapodia-like structure. Scale bar is 5 μm. D. Magnified confocal images illustrating the intracellular vesicles, budding vesicles (left panel) on the plasma membrane and extracellular vesicles (right panel). Scale bar is 1 μm FIG. 5. MG53 contributes to skeletal muscle myogenesis by regulating myoblast differentiation. A. Western blot analysis shows the shRNA mediated down regulation of MG53 in CHO cells. Lysates were prepared from CHO cells transfected with a MG53 expression vector and either shRNA or scrambled shRNA plasmids targeting MG53. Immunoblotting was performed with polyclonal anti-mouse antibody for MG53 (upper panel) or monoclonal antibody for •-actin (lower panel). B. Representative fluorescent microscope images of C2C12 cells at different days of differentiation (Day 0, upper panel; Day 5, middle panel; Day 10, lower panel.) to illustrate the absence of myotube formation in cells transfected with shRNA against MG53 (right panel) compared to the scrambled shRNA as control (left panel). Scale bar is 50 μm. C. Statistical analysis of the down-regulation of MG53 inhibiting myotube formation at 5 days or 10 days (*p<0.01 and **p<0.001 by t test) compared to the control. The ratio of green myotubes to all green cells was defined as the percentage of myotubes. Data are represented as mean with SEM.

MG53 mediates vesicle trafficking in muscle cells. Although there is no membrane-spanning segment or lipid-modification motif in its primary structure, MG53 appears to be primarily restricted to membrane structures in skeletal muscle. Immunohistochemical analysis revealed specific labeling for MG53 in the sarcolemma membrane and intracellular vesicles (FIG. 3D). Overexpression of MG53 in the C2C12 myogenic cell line leads to dramatic morphological changes. Cells transiently transfected with MG53 and GFP displayed extensions of the plasma membrane with distinct filapodia-like structures that were not present in cells expressing GFP alone (FIGS. 4A-D). Using a GFP-MG53 fusion construct, it was found that MG53 is localized to both intracellular vesicles and the plasma membrane of C2C12 myoblasts (FIG. 4B). Live cell fluorescence imaging revealed dynamic intracellular trafficking and fusion events in C2C12 cells overexpressing GFP-MG53. This GFP-MG53 mediated vesicle fusion at the cell surface membrane results in budding of GFP-MG53 vesicles off the cell membrane (FIG. 4D). This is confirmed by imaging of vesicle fusion events at the plasma membrane using total internal reflection fluorescence (TIRF) microscopy, which showed that vesicle fusion event are greatly enhanced by co-expression of MG53 (data not shown). As a whole, these experiments illustrate that endogenous MG53 is a muscle-specific TRIM family protein that mediates trafficking of intracellular vesicles to the sarcolemmal membrane.

MG53 is a muscle-specific protein that contains TRIM and SPRY motifs. In previous studies we have established a monoclonal antibody (mAb) library that targets proteins associated with the triad junction in skeletal muscle. Screening of this immuno-proteomic library for muscle specific proteins led to the identification of an antigen named MG53 with a molecular size of 53 kilodaltons (kDa), which was recognized by mAb5259. MG53 was partially purified from rabbit skeletal muscle by an immunoaffinity column conjugated with mAb5259, and subjected to amino acid sequencing. Based on the obtained partial amino acid sequences, cDNAs encoding MG53 were isolated from rabbit and mouse skeletal muscle libraries. Genomic library search identified the corresponding MG53 gene on the human 16p11.2 locus. The predicted amino acid sequences for MG53 in several species are shown in FIG. 1.

Domain homology analysis revealed that MG53 contains the prototypical TRIM signature sequence of RBCC plus a SPRY domain at the carboxyl-terminus, and thus belongs to the TRIM/RBCC family (FIG. 1). Of the approximately 60 TRIM family members so far identified in the mammalian genomes, 15 members carry a similar SPRY domain following the RBCC domain, and MG53 shows a conserved primary structure with these TRIM sub-family proteins (FIG. 2). However, surprisingly and unexpectedly our studies indicate that MG53 is the only TRIM family protein of those in FIG. 2 that demonstrate membrane repair function.

Western blot assay confirms the muscle-specific expression of MG53 in mouse tissues (FIG. 3B). Although there is no membrane-spanning segment or lipid-modification motif in its primary structure, MG53 appears to be primarily restricted to membrane structures in skeletal muscle. Immunohistochemical analysis with mAb5259 showed specific labeling for MG53 in the sarcolemmal and TT membranes in transverse sections of skeletal muscle fibers (FIG. 3C). Moreover, transverse sections revealed localized concentration of MG53 near the sarcolemmal membrane, with a broader staining pattern than is typically observed for integral membrane proteins of the sarcolemma. Thus, MG53 is a muscle specific TRIM family protein that displays a unique subcellular distribution pattern for a TRIM family protein.

Overexpression of MG53 produces filapodia-like structures in both excitable and non-excitable cells. To elucidate the cell biological function of MG53, mouse MG53 cDNA was expressed in C2C12 myogenic cells, as well as Chinese hamster ovary (CHO) cells. C2C12 cells at the myoblast stage do not express endogenous MG53 protein, however differentiated C2C12 myotubes do express MG53. CHO cells are non-excitable epithelial cells that contain no endogenous MG53 protein. As shown in FIG. 4A (left panel), transient transfection of MG53 cDNA into C2C12 myoblasts or CHO cells produced the expression of a recombinant protein of 53 kDa that could be recognized by mAb5259. The molecular size of the recombinant protein is identical to the endogenous MG53 present in both rabbit and mouse muscles, thus confirming the identity of the isolated cDNA clone as MG53. Co-transfection of cells with two plasmids containing cDNAs that encode either EGFP or MG53 at a ratio of 10:1 provided a convenient method to identify transfected cells by fluorescence microscopy. With confocal microscopic imaging, we observed dramatic changes in morphology of cells transiently transfected with MG53 (FIG. 4B). Specifically, extensions of the cell surface membranes formed distinct filapodia-like structures in both CHO cells and C2C12 myoblasts that transiently overexpress MG53.

To further examine the MG53-induced changes in cell morphology, two GFP-fusion constructs of MG53 were generated: GFP-MG53 and MG53-GFP, with attachment of GFP to the amino-terminus and carboxyl-terminus of MG53, respectively. Although both fusion proteins can be expressed in CHO cells and C2C12 myoblasts (FIG. 4C, right panel), the subcellular distribution and functional effects of GFP-MG53 and MG53-GFP were dramatically and surprisingly different. Using confocal microscopy, it was found that GFP-MG53 fusion proteins were localized to both intracellular vesicles and cell surface membranes in both CHO and C2C12 cells (FIG. 4C, left panels). This result is consistent with immunostaining localization of MG53 in skeletal muscle fibers (FIG. 3C), and suggests that MG53 participates in membrane trafficking events in muscle cells.

Unexpectedly, the distribution pattern of MG53-GFP fusion protein was mostly cytosolic in both CHO and C2C12 cells (FIG. 4C, right panels), which is in sharp contrast to the membrane-attached distribution of GFP-MG53. In addition, the extensive filapodia-like membrane extensions induced by overexpression of MG53 or GFP-MG53 were completely absent in cells transfected with MG53-GFP. Since shielding the carboxyl-terminus of MG53 by fusion with GFP alters the subcellular distribution of MG53, it is likely that the SPRY motif at the carboxyl-terminal end of MG53 plays a role in anchoring MG53 to the different membrane compartments and is essential for MG53 function (see FIGS. 13 and 14).

Live cell fluorescence imaging identified dynamic trafficking of intracellular vesicles, and active exocytotic fusion and vesicle budding at the cell surface membrane, in cells overexpressing GFP-MG53 (FIG. 4D). Close examination revealed the occurrence of vesicle fusion events at the surface membrane (FIG. 4D, left panel). Budding of vesicles containing GFP-MG53 could be clearly identified, as well as released extracellular vesicles observed in the vicinity of transfected cells (FIG. 4D, right panel).

Taken together, cell imaging studies suggest that MG53 can localize to both intracellular vesicles and target to cell surface membranes, and that it is a key mediator of membrane fusion and vesicle budding.

Figure 12:
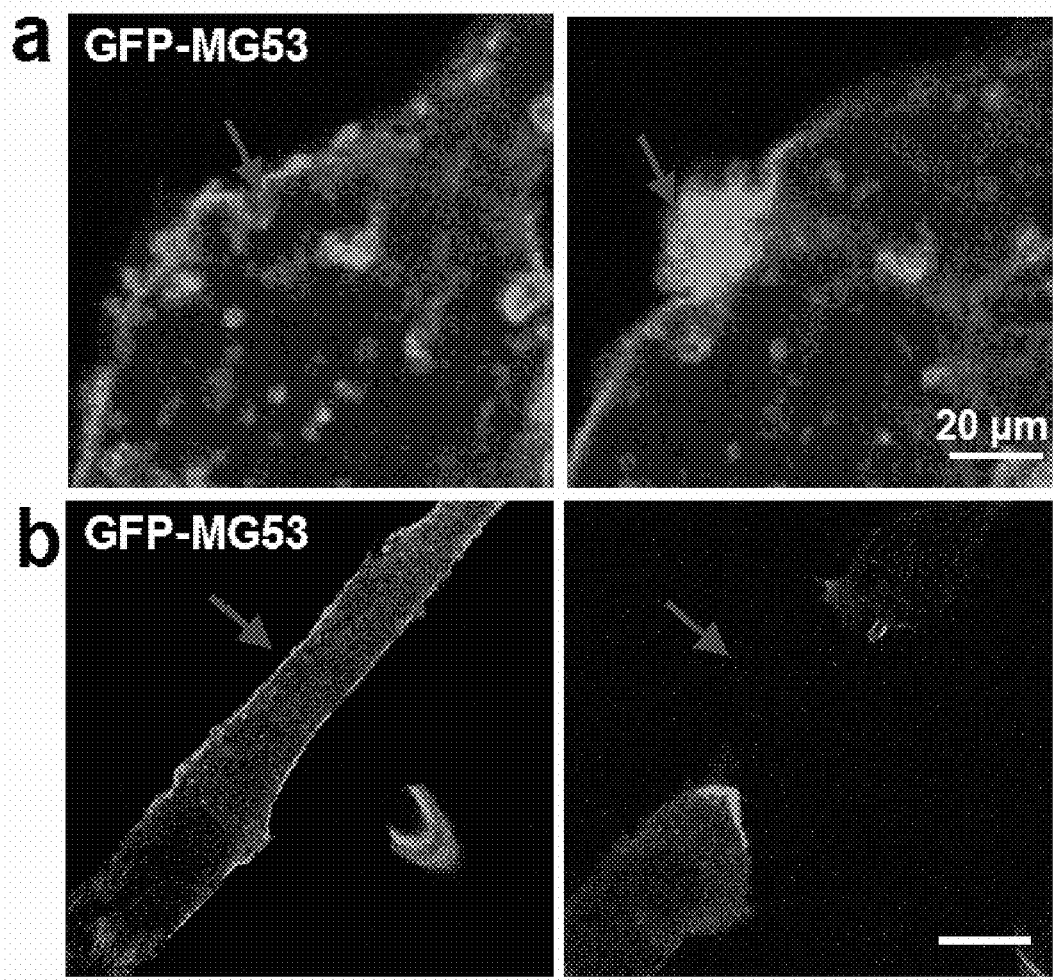
FIG. 12. MG53 containing vesicles form a patch in the plasma membrane following physical insult. A. Damage of a C2C12 myoblast membrane using a micropipette leads to rapid accumulation of GFP-MG53 at the injury site (arrow). Images were representative of n=40 separate cells. B. Recovery of a mature C2C12 myotube in response to a severe damage, e.g. separation of the cell membrane, is associated with recruitment of GFP-MG53 toward the healing site (n=28).

MG53 mediates acute membrane repair in skeletal muscle fibers following cellular injury. Vesicle fusion with the plasma membrane is required for membrane repair and previous studies indicate a role for dysferlin in maintenance of skeletal muscle membrane integrity. Our findings indicate that MG53 is capable of driving the trafficking of vesicles to the plasma membrane, perhaps to mediate the repair process following membrane disruption. Acute cellular injury generated by physical penetration of the plasma membrane with a microelectrode leads to rapid recruitment of GFP-MG53 vesicles toward the injury site (FIG. 12A). When more severe damage that results in fracture of the cell occurs, the repair site is densely labeled with GFP-MG53 (FIG. 12B). In addition, this acute membrane repair also was observed in mature C2C12 myotubes (see movies 2 and 3). This data indicates that MG53-mediated vesicle trafficking play an active role in acute repair of cell membrane.

Figure 9:
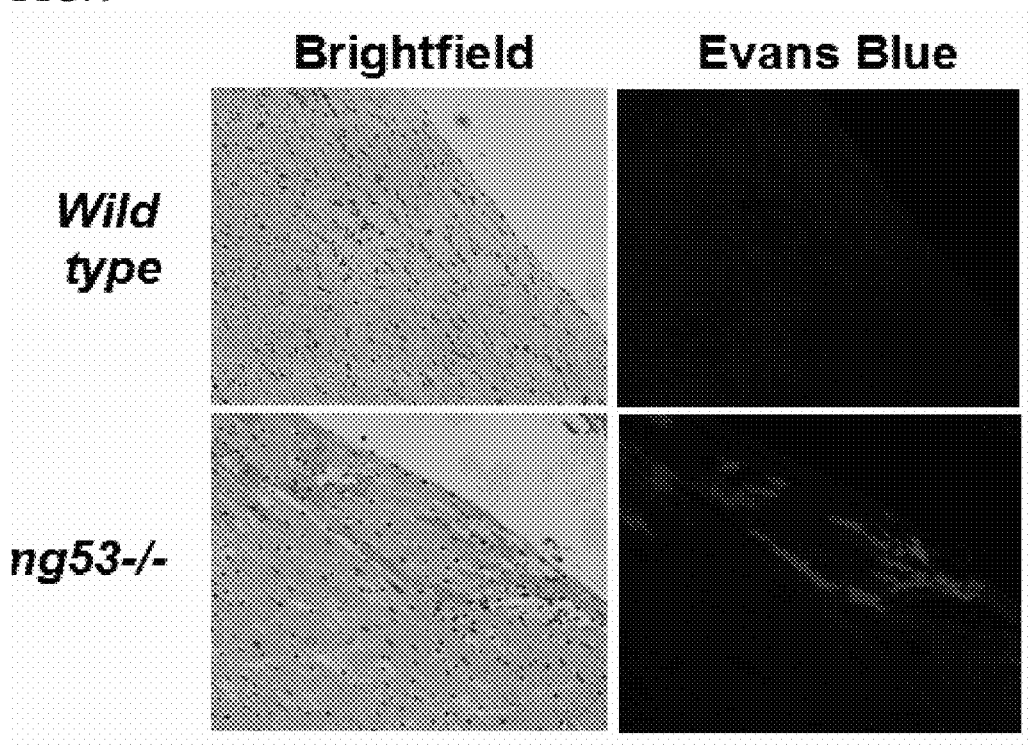
FIG. 9. MG53 knockout mice are susceptible to cardiac damage. Paraffin-embedded sections of myocardium from unexercised wild type mice show normal morphology (left) and no Evans blue staining (right). In contrast, and mg53−/− mice display a Evans blue infiltration into myocytes, indicating that there are significant defects in membrane integrity in the mg53−/− heart.
Figure 11:
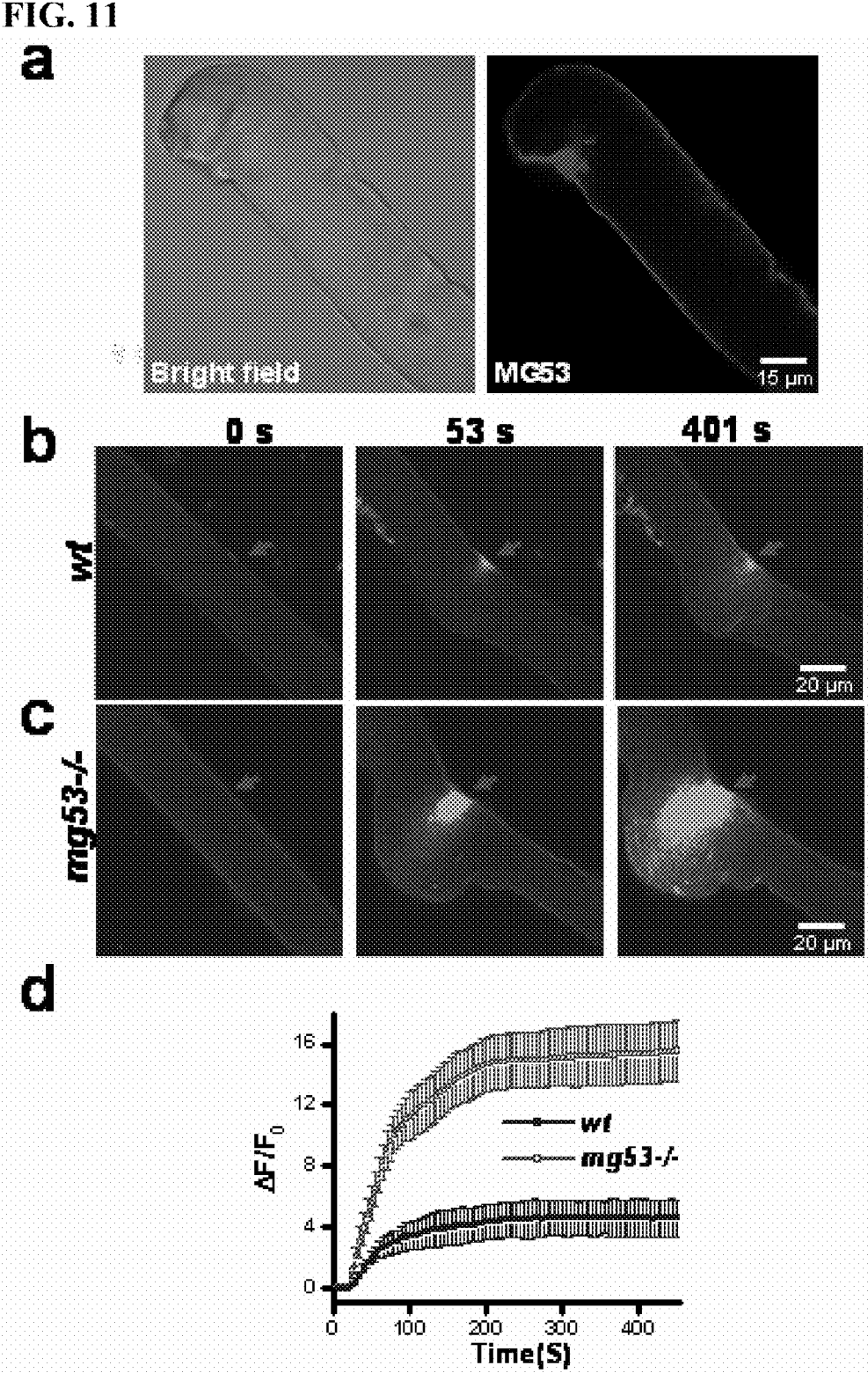
FIG. 11. Ablation of MG53 leads to defective muscle membrane repair function. (a) Immunostaining of MG53 in isolated wt FDB fibers to illustrate their co-localization at the injury site. These are representative images from >20 different muscle fibers which display damage during isolation. (b) Exclusion of membrane-impermeable FM-143 fluorescent dye in a FDB muscle fibers isolated from the wt mice following laser-induced damage of the sarcolemmal membrane. (c) Entry of FM-143 fluorescent dye into a FDB muscle fiber isolated from the mg53−/− mice following laser-induced damage. Times after laser injury were indicated. (d) Time-dependent accumulation of FM-143 inside the FDB muscle fiber induced by a laser damage of the sarcolemmal membrane. Data are means±s.e.m. for n=30 fibers obtained from wt mice and n=18 fibers from mg53−/− mice.

To further define the physiological function of MG53 in muscle membrane repair, a mouse model null for MG53 was generated (FIGS. 9-11). The mg53−/− mice are viable up to 11 month of age under unstressed conditions. In vivo stress tests revealed severe defects in membrane repair function of the mg53−/− muscle. As shown in FIG. 10C, membrane injury induced by down-hill running exercise revealed severely compromised contractile function of the soleus muscle from the mg53−/− mice. Without the strenuous exercise, mg53−/− soleus muscles displayed some difficulty in recovery of contractile function after ex vivo fatigue stimulation, compared with the wild type (wt) controls (not shown). These differences can be drastically exaggerated following exercise-induced damages at 8-10 month of age. Clearly, more severe damage could be found with the mg53−/− muscle, where weaker and fluctuating contractile function was observed in comparison with the wt muscle (FIG. 10D).

Injection of Evans blue dye into the intraperitoneal space of mice directly monitors sarcolemmal membrane integrity after down-hill exercise-induced muscle damage. As shown in FIG. 10E, muscle fibers isolated from the mg53−/− mice showed significantly more Evans blue staining than the wt muscle, revealing extensive degree of exercise-induced muscle damage. This was confirmed by H/E staining that illustrated increased dystrophy in the mg53−/− muscle that was increased in aged mg53−/− mice compared to young mg53−/− mice (FIG. 10A). Quantitative assay of total absorbance of Evans blue extracted from muscle bundles provided direct support for the increased muscle damage in the mg53−/− mice after down-hill running (FIG. 10F).

Consistent with the role of MG53 in membrane repair, elevated concentrations of MG53 was observed at the site of injury with immunostaining of individual flexor digitorum brevis (FDB) muscle fibers that were damaged during isolation (FIG. 11A). These membrane patches would frequently co-localize with staining for dysferlin. We directly evaluated the MG53-mediated membrane repair function through measurement of FM-143 fluorescent dye entry after laser-induced membrane damage to individual FDB muscle fibers. The wt muscle fibers possessed intrinsic membrane repair function and were fairly resistant to laser-induced damage of the sarcolemmal membrane, as they displayed effective exclusion of the FM-143 fluorescent dye (FIG. 11B). Significant entry of FM-143 fluorescent dye into the mg53−/− FDB muscle fibers could be observed following laser-induced damage (FIG. 11C). The time-dependent accumulation of FM-143 inside the FDB muscle fibers following laser damage of the sarcolemmal membrane provides direct support for a defective membrane repair function of the mg53−/− muscle (FIG. 11D).

Expression of MG53 is essential to maintain normal cardiac membrane integrity. Defects in in mg53−/− mice are not limited to skeletal muscle fibers. During injection of Evans blue dye ~50% of the mg53−/− mice would die within 16 hours of injection compared to none of the wild type animals injected. Postmortem examination of mg53−/− hearts revealed extensive labeling of cardiac muscle fibers with Evans blue, even in absence of exercise stress (FIG. 9). We also found that exercise would greatly exacerbate the extent of Evans blue staining in mg53−/− hearts.

Figure 5:
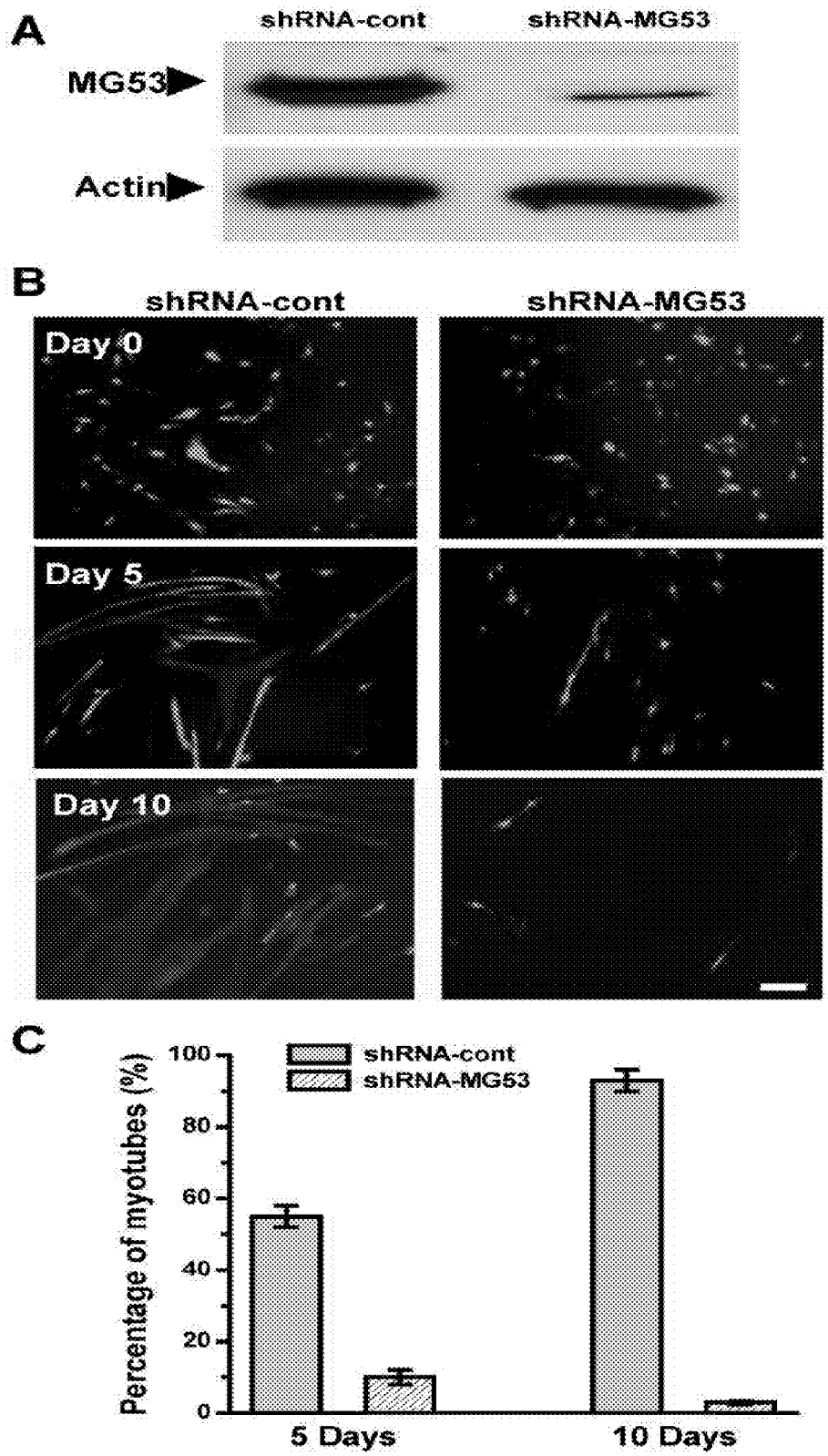

Role for MG53 in myotube formation during muscle development. Membrane repair is only one of the cellular processes that require dynamic trafficking of intracellular vesicles to allow reorganization of cellular membranes. One such process in skeletal muscle occurs during myogenesis. During the differentiation of myoblasts into myotubes, the mononuclear myoblasts must fuse together to form multinucleated myotubes. To directly examine the role of MG53-mediated membrane fusion on the myogenesis of skeletal muscle, a specific RNA interference probe was used to knockdown the expression of endogenous MG53 in differentiating C2C12 myotubes. A small hairpin (sh)RNA probe recognizing the nucleotide sequence 632-652 of the mouse MG53 cDNA suppressed greater than 80% of MG53 expression in cells transfected with shRNA-MG53, as compared with cells transfected with a non-specific shRNA probe for a scrambled version of the MG53 target sequence (FIG. 5A). Acute suppression of MG53 resulted in a marked decrease in C2C12 myotube differentiation (FIG. 5B). C2C12 myoblasts transfected with the shRNA-MG53 probe formed significantly fewer myotubes at both day 5 and day 10 after serum deprivation-induced differentiation (FIG. 5C). These results suggest that normal expression of MG53 is necessary for the differentiation of C2C12 myoblasts into myotubes.

Because caveolin-3 is developmentally regulated (FIG. 6A) and can interact with MG53 (FIG. 6B), we tested whether MG53-induced filapodia-like structure in C2C12 myoblasts could be influenced by the overexpression of caveolin-3. As shown in FIG. 6D, concurrent overexpression of caveolin-3 and MG53 in either C2C12 myoblasts lead to remarkable inhibition of the appearance of filapodia-like structures associated with GFP-MG53 overexpression. On average, C2C12 myoblasts transfected with caveolin-3 and GFP-MG53 (in a ratio of 10:1) exhibited an 82±6% reduction in the appearance of filapodia-like structures, respectively (FIGS. 6E and F). These results suggest that caveolin-3 represents one of the molecular regulators of MG53-mediated membrane fusion events.

To further investigate the role of caveolin-3 in the subcellular distribution of MG53 and the formation of filapodia-like structures, a caveolin-3 shRNA plasmid (Table 1) was constructed that includes an independent red fluorescence protein expression cassette to provide a marker for shRNA transfected cells. Western blot analysis shown in FIG. 7A reveals that the shRNA-cav3 probe is highly efficient at suppressing the caveolin-3 expression in CHO cells transiently transfected with the caveolin-3 cDNA without affecting the expression of caveolin-1.

TABLE 1

Oligos for constructing the shRNA for MG53 and Caveolin-3.

| Plasmid | | Inserted oligos |
|---|---|---|
| Scrambled shRNA for MG53 | sense (SEQ ID NO. 18) | 5'-GTA CCT CGC CTG CCG TCC AAA GTT GTA ATC AAG AGT TAC AAC TTT GGA CGG CAG GCT TTT TGG AAA-3' |
| | antisense (SEQ ID NO. 19) | 5'-AGC TTT TCC AAA AAG CCT GCC GTC CAA AGT TGT AAC TCT TGA TTA CAA CTT TGG ACG GCA GGC GAG-3' |
| shRNA for MG53 | sense (SEQ ID NO. 20) | 5'-GTA CCT CGA GCT GTC AAG CCT GAA CTC TTC AAG AGA GAG TT CAG GCT TGA CAG CTC TTT TTG GAA A-3' |
| | antisense | 5'-AGC TTT TCC AAA AAG AGC TGT CAA GCC TGA |

TABLE 1-continued

Oligos for constructing the shRNA for MG53 and Caveolin-3.

| Plasmid | | Inserted oligos |
|---|---|---|
| | (SEQ ID NO. 21) | ACT CTC TCT TGA AGA GTT CAG GCT TGA CAG CTC GAG-3' |
| Scrambled shRNA for Cav-3 | sense (SEQ ID NO. 22) | 5'-GAT CCG CGG AGA CAT AGC CTG TAA TTC AAG AGA TTA CAG GCT ATG TCT CCG CTT TTT TAC GGG TG -3' |
| | antisense (SEQ ID NO. 23) | 5'- AAT TCA CCG GTA AAA AAG CGG AGA CAT AGC CTG TAA TCT CTT GAA TTA CAG GCT ATG TCT CCG CG -3' |
| shRNA for Cav-3 | sense (SEQ ID NO. 24) | 5'- GAT CCG GAC ATT CAC TGC AAG GAG TTC AAG AGA CTC CTT GCA GTG AAT GTC CTT TTT TAC GGG TG -3' |
| | antisense (SEQ ID NO. 25) | 5'- AAT TCA CCG GTA AAA AAG GAC ATT CAC TGC AAG GAG TCT CTT GAA CTC CTT GCA GTG AAT GTC CG -3' |

Figure 7:
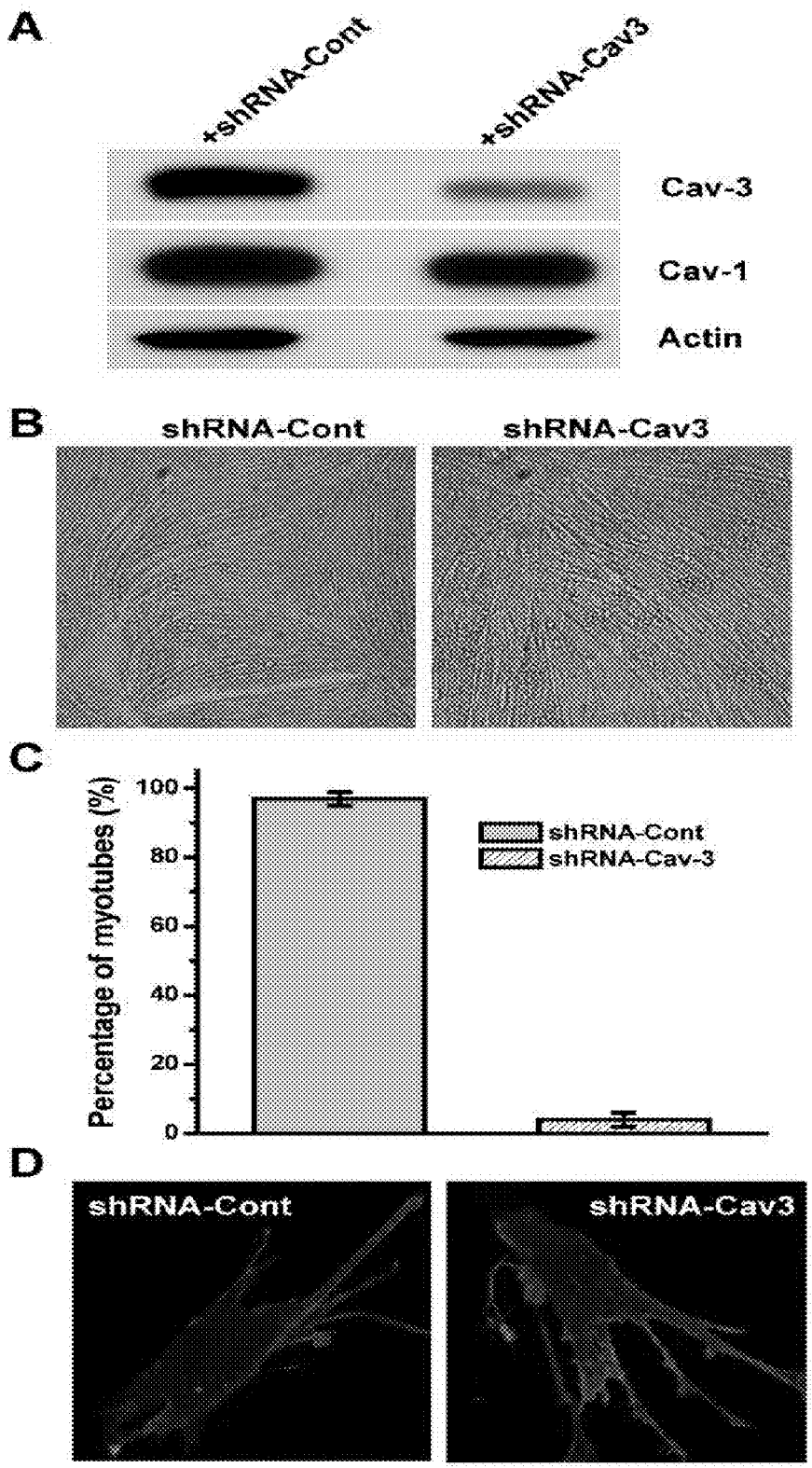
FIG. 7. shRNA-mediated suppression of caveolin-3 expression affects the myotube formation. A. The down-regulation level of caveolin-3 was analyzed by Western blot after transfection with shRNA plasmid for caveolin-3 in C2C12 myotubes (6 days after differentiation). Cells transfected with the scrambled shRNA plasmid acted as a control. B. Down-regulation of caveolin-3 (right panel) by shRNA inhibits myotube formation compared to the control shRNA (left panel). Red fluorescence indicates the transfected cells. Fluorescence microscopy images were taken at 6 days after differentiation induction. Scale bar is 20 μm C. Statistical analysis shows that down-regulation of caveolin-3 significantly inhibits myotube formation at 6 days (*p<0.001 by t test) compared to the control. The ratio of red fluorescent myotubes to all red fluorescent cells served as the percentage of myotubes. Data are represented as mean with SEM. D. Confocal images of C2C12 myoblasts with co-expression of both GFP-MG53 and shRNA for caveolin-3 (right panel) reveal no affect on the filapodia-like structures induced by GFP-MG53 or on the distribution of GFP-MG53 compared to the control shRNA (left panel). Scale bar is 5 μm.

While C2C12 myoblasts transfected with a non-specific shRNA exhibit a normal differentiation pattern as shown by the abundant red-fluorescent labeled myotubes in the left panel of FIG. 7B, acute suppression of caveolin-3 could significantly inhibit the differentiation of C2C12 myoblasts into myotubes (FIG. 7B, right panel). On average, less than 10% of the shRNA-cav3 transfected myoblasts marked by red-fluorescence could differentiate into mature myotubes at day 6 after application of differentiation media (FIG. 7C). This result is consistent with previous studies by other investigators, which showed that the expression of caveolin-3 is essential for differentiation of C2C12 myotubes.

Confocal microscopic imaging showed that transfection of shRNA-cav3 into C2C12 myoblasts did not appear to affect the subcellular distribution of GFP-MG53 expressed in these cells (FIG. 7D). In particular, the distinct pattern of vesicular distribution of GFP-MG53 and filapodia-like membrane structures remained unaffected by the transient transfection with either shRNA-cav3 or the non-specific shRNA. This result is consistent with the lack of expression of caveolin-3 in the myoblast stage of C2C12 cells.

Figure 8:
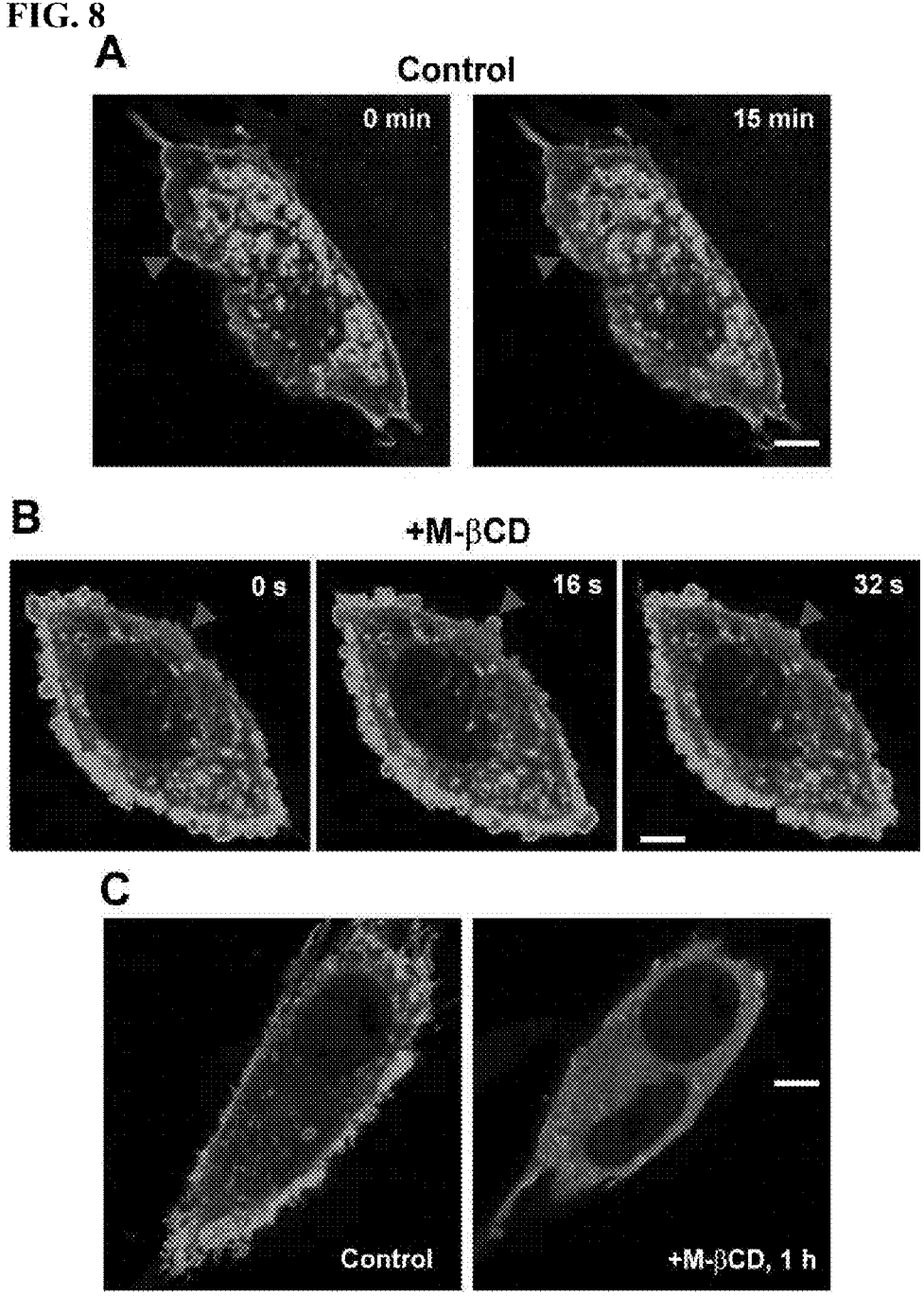
FIG. 8. Treatment of cells with methyl-•-cyclodextrin leads to increased exocytosis and solubilization of GFP-MG53 in C2C12 myoblasts. A. Representative confocal images that illustrate the spontaneous vesicles fusion and budding off from the membrane at the indicated time points (0 minute, left panel; 15 minutes, right panel). Scale bar is 5 μm. B. Confocal images to illustrate the GFP-MG53 induced vesicles budding off from the membrane quickly after treatment with 10 mM M-•CD at the indicated time points (0 second, left panel; 16 seconds, middle panel; 32 seconds, right panel). C. Confocal images to show the solubilization of GFP-MG53 after prolonged treatment with 10 mM M-•CD at room temperature for 1 hour (right panel) compared to the same cell before treatment (left panel). Scale bar is 5 μm.

Due to the essential nature of caveolin-3 in myotube differentiation, the effect of methyl-•-cyclodextrin (M-•CD) on C2C12 myoblasts overexpressing GFP-MG53 was tested to further assay the functional impact of MG53-caveolin interaction on membrane recycling. M-•CD can extract cholesterol from cell membranes and has been widely used as an agent to disrupt caveolae structures. As shown in FIG. 8A, myoblasts overexpressing GFP-MG53 exhibited spontaneous fusion of vesicles both intracellularly as well as at the sarcolemmal membrane. These spontaneous fusion events are slow and occur in the order of minutes. Following treatment with M-•CD, exocytotic events become greatly enhanced resulting in accelerated membrane fusion and massive budding of membrane vesicles (FIG. 8B). These initial alterations are rapidly induced, and extended incubation with M-•CD results in solubilization of GFP-MG53 within the myoblast (FIG. 8C).

Caveolin-mediated internalization of membrane vesicles likely play a regulatory role in restraining that excessive exocyotic events generated by overexpression of MG53. Furthermore, interaction of MG53 with caveolin is necessary to maintain subcellular localization of MG53. This conclusion is supported by results from additional experiments using mutant forms of caveolin-3 (SEQ ID NO. 8).

Role of TRIM and SPRY motifs in MG53 function. Structure/function assessment of the domains of MG53 (FIG. 13) revealed a remarkable polarity of GFP fusion to MG53 in the intracellular distribution of MG53. In particular, fusion of GFP to the carboxyl-terminal end of MG53 alters the ability of MG53 to partition to the vesicular compartment and to target to the sarcolemmal membrane. To further test the function of the TRIM and SPRY domains in facilitating the membrane-fusion function of MG53, a series of deletion mutants coupled to GFP (FIG. 13A) were generated.

To analyze the subcellular localization of these mutant constructs of MG53, confocal microscopic imaging was applied to C2C12 myoblasts following transient expression. As shown in FIG. 13B (right panels), GFP-TRIM or TRIM-GFP were predominantly localized to intracellular vesicles without apparent labeling of the sarcolemmal membrane. This result suggests that the SPRY domain, which is absent from GFP-TRIM or TRIM-GFP, is necessary for targeting of MG53 to the sarcolemmal membrane. The fact that MG53-GFP exhibited a predominantly cytosolic distribution (FIG. 13B, left panel), further supports the role of SPRY in targeting MG53 to the cell surface membrane.

Interestingly, although GFP-SPRY or SPRY-GFP displayed a predominantly cytosolic pattern of distribution, they are clearly excluded from intracellular vesicles (FIG. 13B, middle panels). The cytosolic distribution pattern coupled with the exclusion of localization at intracellular vesicles of GFP-SPRY and SPRY-GFP likely reflects the role of TRIM. Presumably, the TRIM motif can mediate the adherence of MG53 to intracellular vesicles (FIG. 13B, right panels). The SPRY domain is insufficient to target to the sarcolemma by itself, therefore the TRIM domain must be present in tandem with the SPRY domain for proper trafficking of MG53 to the sarcolemmal membrane. In addition, our co-immunoprecipitation data shows that caveolin-3 interacts with the TRIM motif of MG53 (FIG. 13C). Thus, it is possible that the functional interaction between MG53 and caveolin-3 may underlie some of the cellular factors contributing to the diffuse pattern of GFP-SPRY and SPRY-GFP in C2C12 myoblasts. Overall, the regulated distribution of MG53 to the cell surface and intracellular compartments would likely result from coordinated action between the TRIM and SPRY domains. This requirement for both TRIM and SPRY for proper MG53 subcellular localization also has apparent functional significance, as none of these deletion mutants display the filapodia-like structures or the robust vesicle budding events observed from overexpression of full-length MG53.

Figure 6:
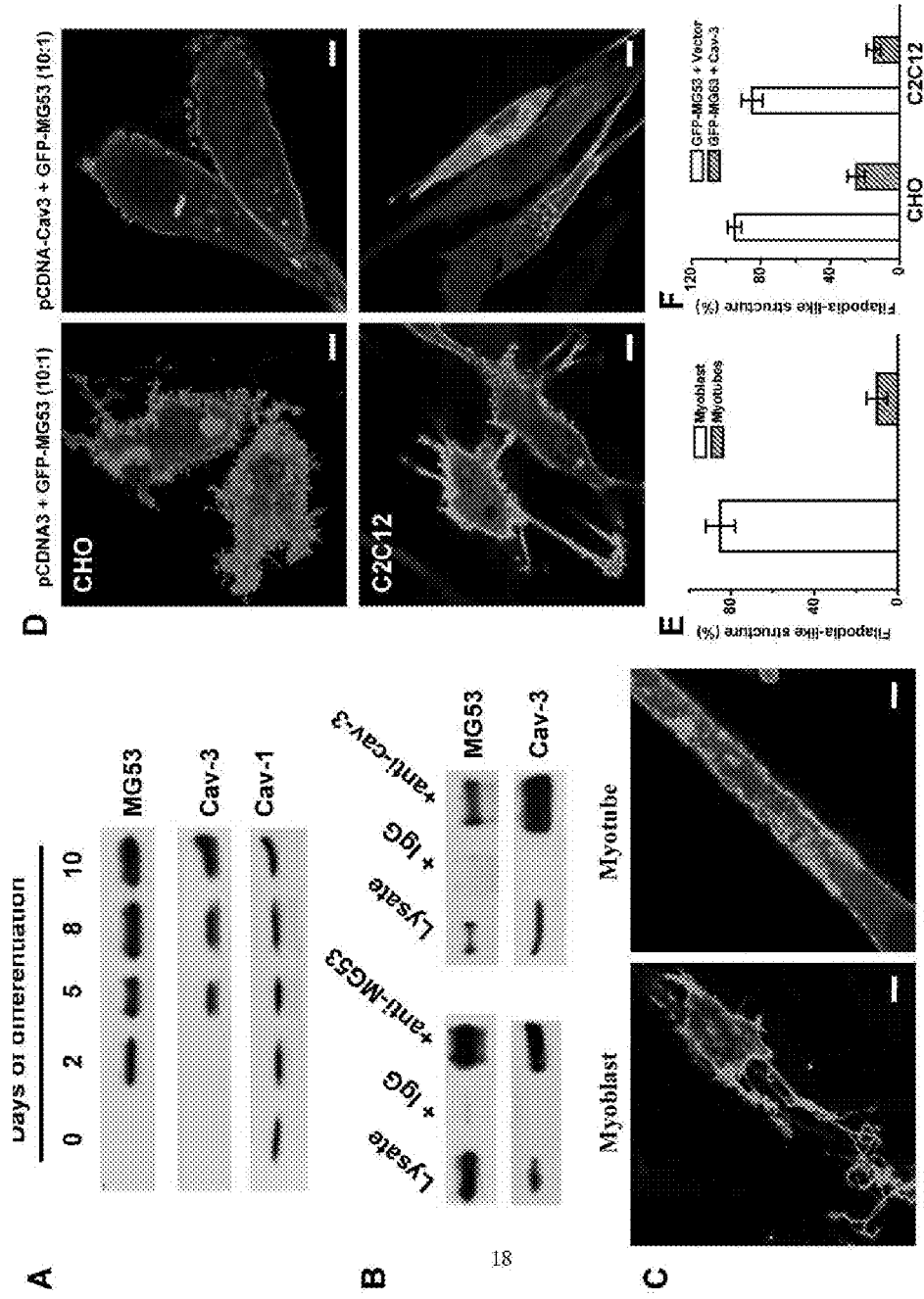
FIG. 6. Functional interaction between MG53 and caveolin-3 regulates dynamic membrane budding process in skeletal muscle. A. Western blot analysis of the expression level of MG53 (upper panel), caveolin-3 (middle panel) and caveolin-1 (lower panel) during C2C12 cell differentiation at the indicated time following induction of differentiation (day 0, 2, 5, 8, 10). B. Whole cell lysate from mouse gastrocnemius skeletal muscle was subjected to co-IP with anti-MG53 (rabbit polyclonal antibody), anti-caveolin-3 (mouse monoclonal antibody), normal rabbit IgG as a negative control and cell lysate as a positive control. C. Confocal images to illustrate the disappearance of filapodia-like structures during the process of C2C12 myotube formation (right panel) compared to myoblasts (left panel). Notice that intracellular vesicles positive for GFP-MG53 are still present in transfected C2C12 myotubes. D. Overexpression of caveolin-3 in C2C12 myoblast cells prevents MG53-induced filapodia-like structures from forming. CHO cells (upper panel) or C2C12 myoblast cells (lower panel) were co-transfected with pcDNA-Cav-3 and GFP-MG53 (10:1) (right panel), or co-transfected with pcDNA vector and GFP-MG53 (10:1) as control (left panel). Confocal images were taken at 48 hours after transfection. Scale bar is 10 μm. E and F. Statistical analysis for C and D. The ratio of cells displaying filapodia-like structures to all green cells was defined as the filapodia-like structure percentage. Data are represented as mean with SEM. (*p<0.01 by t test).
Figure 14:
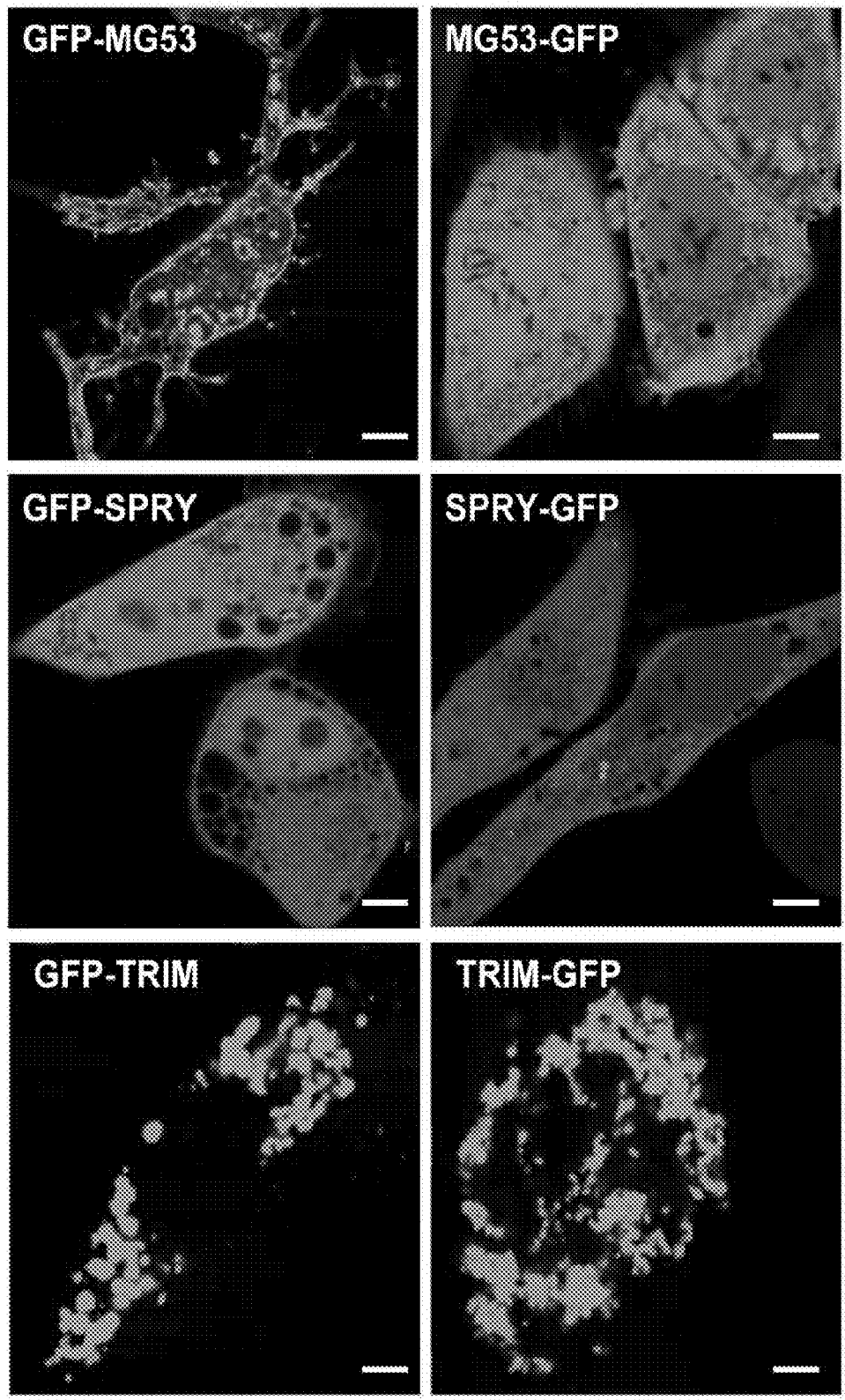
FIG. 14. Role of TRIM and SPRY domains in targeting of MG53 to the cell surface membrane in non-muscle CHO cells. Representative confocal images showing that GFP-MG53 exhibits intracellular vesicle, membrane targeting and budding, however MG53-GFP is mainly soluble in nature (upper panel); SPRY-GFP and GFP-SPRY are cytosolic (middle panel); TRIM-GFP and GFP-TRIM are mainly intracellular vesicle, and do not target to plasma membrane (lower panel). "TRIM" represents a.a. 1-287 and "SPRY" represents a.a. 288-477 and includes both the PRY and SPRY motifs. Scale bar is 5 μm.

MG53 can fully function in non-muscle cell types. Analysis of MG53 function in myogenic C2C12 cells and in isolated skeletal muscle fibers reveals an essential role for MG53 in vesicle trafficking and membrane repair in striated muscle. Considering that membrane repair is an essential to maintain cellular homeostasis, it is likely that similar repair mechanisms in other non-muscle cell types could use similar molecular machinery to facilitate this process. To test this possibility, several of the previous experiments conducted with C2C12 myogenic cells were replicated with non-muscle Chinese hamster ovary (CHO) cells. In these cells, a very similar phenotype to that seen in the C2C12 cells was found. First, GFP-MG53 could produce filapodia-like protrusions of the plasma membrane and localize to both intracellular vesicles and to the plasma membrane (FIGS. 6 and 14). Second, MG53 deletion proteins behaved in an identical fashion to that seen in C2C12 cells. Finally, caveolin-3 can also control the activity of MG53 expressed in CHO cells (FIG. 14). As a result, these studies indicate that MG53 acts through a conserved molecular mechanism that is present in other cell types besides muscle.

Figure 15:
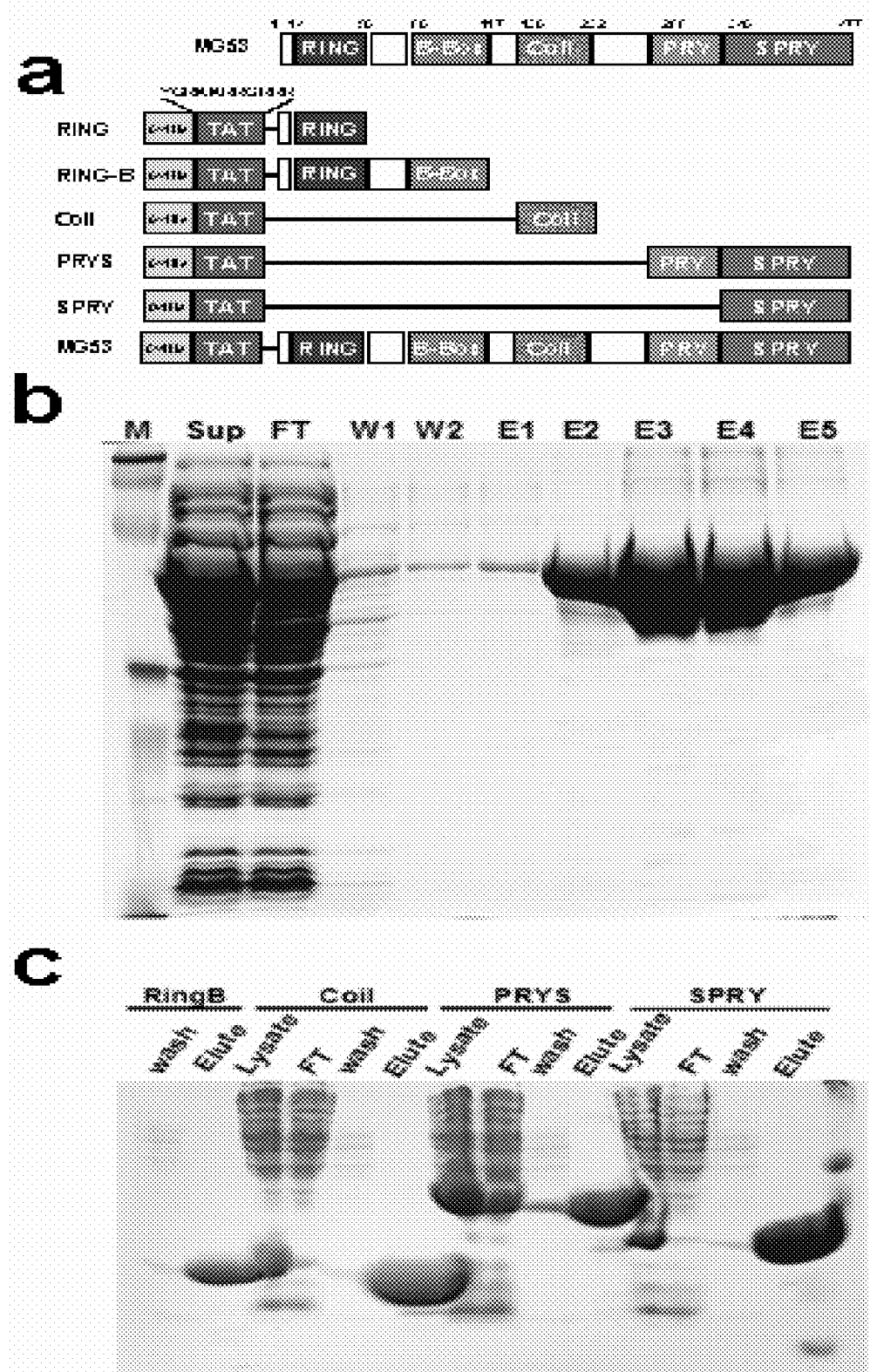
FIG. 15. Purification of recombinant TAT-MG53 and mutant constructs. (a) Representation of the TAT-MG53 recombinant protein construct and associated deletion constructs. (b) Coomassie blue staining of a denaturing gel showing the purification steps for TAT-MG53. Gel lanes were loaded with a molecular weight marker (M), E. coli supernatant (Sup), immunoaffinity column flow through (FT), wash flow through (W1,2) and elution fractions (E1-5). (c) Coomassie stained denaturing gel of recombinant mutant TAT-MG53 proteins isolated from E. coli.

Purification of recombinant MG53 and TAT-MG53. To supply MG53 to the target cell to facilitate improved cellular regeneration a cell penetrating peptide sequence derived from the TAT gene in HIV is coupled with full-length MG53(TAT-MG53) and with several MG53 deletion mutants (FIG. 15A). These fusion proteins can be expressed in *E. coli* bacteria and effectively purified using affinity chromatography (FIGS. 15B and 15C). We have previously shown that the application of such fusion proteins to cell monolayers results in effective translocation of recombinant proteins into mammalian cells. Generation of these fusion proteins should allow us to increase the amount of MG53 within target cells so that we can resolve the therapeutic effects of MG53 on dermal tissue.

Figure 18:
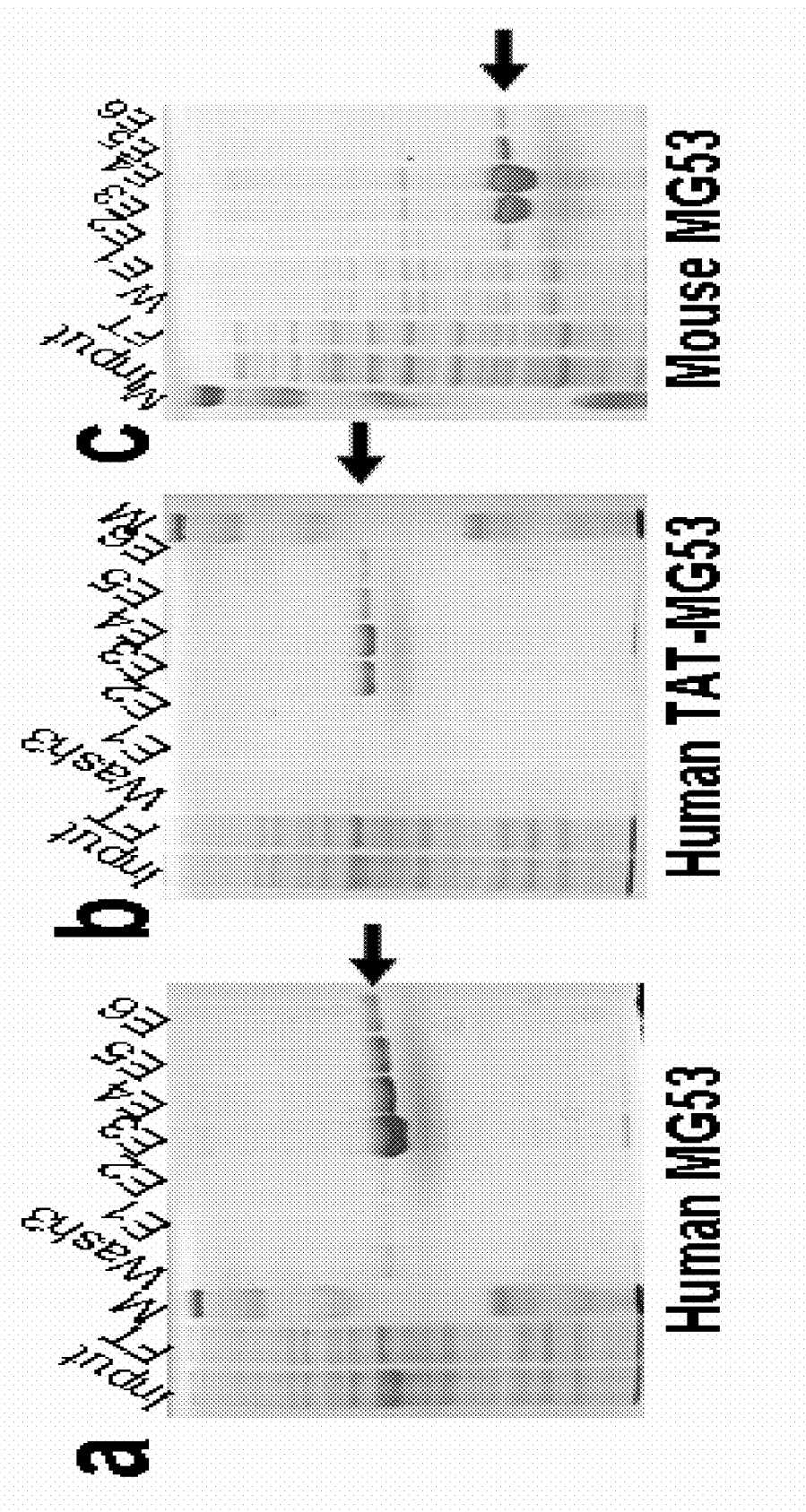
FIG. 18: Recombinant expression of MG53. (a) Coomassie blue stained gel of recombinant human MG53 protein (arrow) fractions isolated from Sf9 cells with a Ni-NTA column. Input=cell extract, FT=flow through, M=marker, E=elution number. (b) Coomassie blue stained gel of recombinant human TAT-MG53 (arrow) isolated from Sf9 cells. (c) Coomassie blue stained gel of recombinant mouse TAT-MG53 (arrow) isolated from E. coli.

Expression of recombinant MG53 can be performed in eukaryotic or prokaryotic cells. FIG. 18 illustrates that recombinant MG53 can be expressed in either eukaryotic or prokaryotic systems. Briefly, recombinant MG53 is expressed in Sf9 cells as a fusion protein containing both a TAT peptide portion and a six-histidine tag (6-HIS tag). This histidine tag can be used to isolate and purify recombinant protein using filtration chromatography techniques well known in the art. Panel (A) shows the Coomassie blue stained gel of recombinant human MG53 protein (arrow) fractions isolated from Sf9 cells with a Ni-NTA column. Input=cell extract, FT=flow through, M=marker, E=elution number. (B) Coomassie blue stained gel of recombinant human TAT-MG53 (arrow) isolated from Sf9 cells. The Coomassie blue stained gel in (C) represents recombinant mouse TAT-MG53 (arrow) expressed and isolated from *E. coli*.

Figure 17:
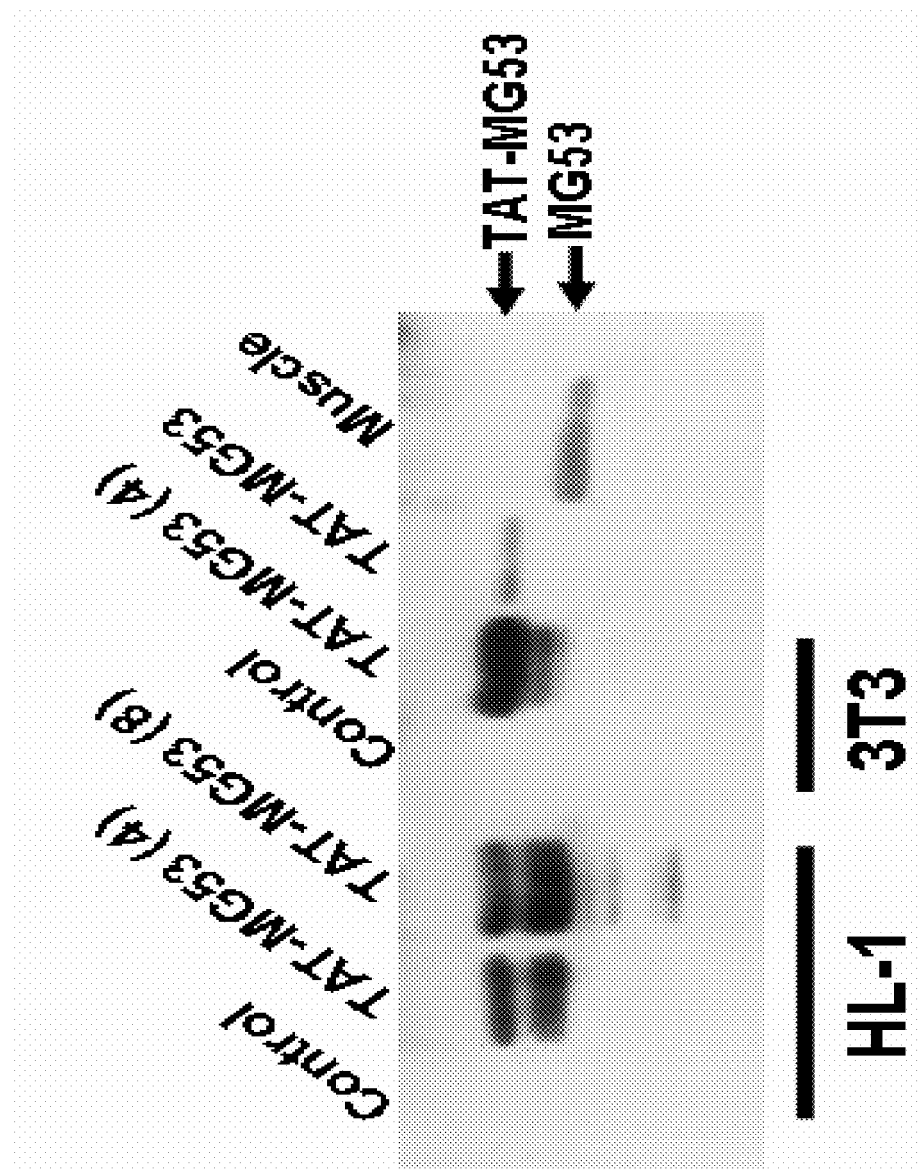
FIG. 17: Recombinant human TAT-MG53 (See HIV-1 TAT protein, SEQ ID NO. 17) can penetrate cells of different origins. HL-1 cardiomyocytes and 3T3 fibroblasts were incubated with 4 or 8 μg/mL recombinant human TAT-MG53 for 15 minutes at 37° C. Cells were washed three times in a buffered salt solution and then lysed for western blot analysis. Western blot shows that control cells (control) do not contain endogenous MG53, however those incubated with TAT-MG53 contain ample intracellular TAT-MG53. Note that TAT-MG53 is slightly larger than MG53 visualized from skeletal muscle extract (muscle) due to the addition of the TAT cell penetrating peptide to the protein.

Recombinant human TAT-MG53 can penetrate cells of different origins. In order for MG53 to function it must be present intracellularly. In order to demonstrate that recombinant MG53 can be translocated across the cellular membrane in therapeutically significant amounts HL-1 cardiomyocytes and 3T3 fibroblasts were incubated with about 4 or 8 μg/mL recombinant human TAT-MG53 for 15 minutes at 37° C. (FIG. 17). The cells were washed three times in a buffered salt solution and then lysed for western blot analysis. Western blot shows that control cells (control) do not contain endogenous MG53, however those incubated with TAT-MG53 contain ample intracellular TAT-MG53. Note that TAT-MG53 is slightly larger than MG53 visualized from skeletal muscle extract (muscle) due to the addition of the TAT cell penetrating peptide to the protein. Multiple bands may be generated by intracellular processing of the TAT-MG53 fusion protein. Therefore, in a preferred embodiment of the MG53 polypeptide therapeutic, the present invention comprises a recombinant polypeptide comprising a TAT polypeptide portion and an MG53 polypeptide portion, wherein the TAT and MG53 polypeptide portions are present in a single, contiguous polypeptide chain.

Figure 16:
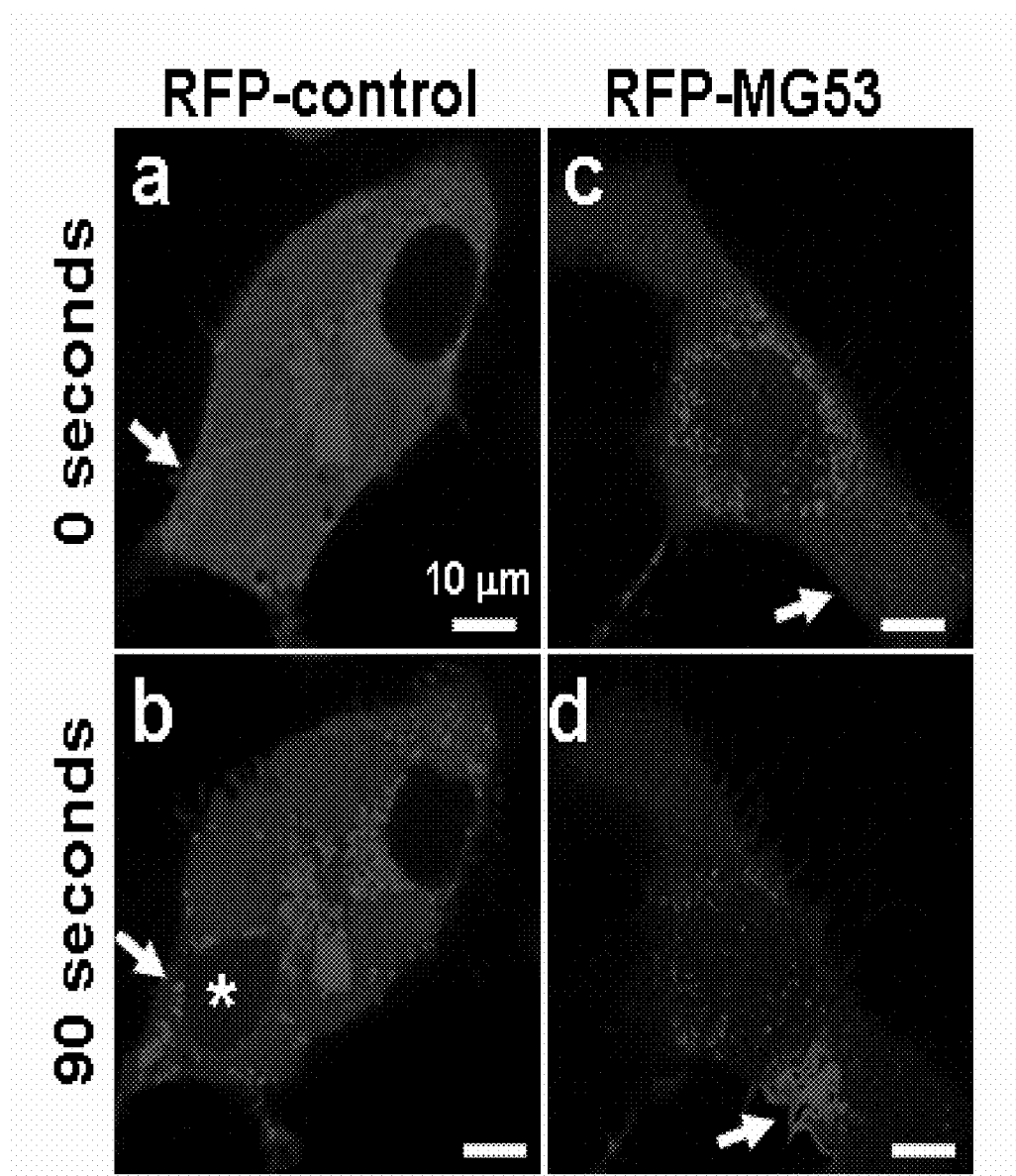
FIG. 16: Stable HEK293 (Human Embryonic Kidney) cell lines were generated that express RFP-MG53. (a) Cell lines that stably express an RFP (red fluorescent protein) control protein that shows a cytosolic expression pattern. (b) Injury of HEK293 cells expressing RFP only with a microelectrode results in no translocation of RFP to the injury site (arrow). Some bleaching of RFP fluorescence occurs from excessive entry of extracellular buffer (*). (c) HEK293 cells that are stably expressing RFP-MG53 show localization to intracellular vesicles. (d) Injury of HEK293 cells expressing RFP-MG53 results in massive translocation of MG53 to the injury site (arrow) in less than 90 seconds. Limited buffer entry into the cell by rapid repair of the plasma membrane prevents bleaching of the RFP-MG53 fluorescence.

Heterologous expression of MG53 in a human cell line results in membrane repair in response to acute injury. FIG. 16 demonstrates that recombinant MG53 can be expressed in a heterologous expression system and retain its ability to repair cell membrane damage without the expression of additional proteins. Specifically, MG53 was cloned into an expression vectors as a fusion protein with red fluorescent protein (RFP). The fusion protein was expressed in a human embryonic kidney cell line (HEK293 fibroblast cell line) and the cell's ability to repair membrane damage was compared to cells expressing only RFP. Panel (a) demonstrates that cell lines stably expressing an RFP (red fluorescent protein) control protein show a cytosolic expression pattern. However, in HEK293 cells expressing RFP only (FIG. 16A); injury with a microelectrode results in no translocation of RFP to the injury site (arrow). Some bleaching of RFP fluorescence occurs from excessive entry of extracellular buffer (*). In contrast, HEK293 cells that are stably expressing RFP-MG53 (c) show localization to intracellular vesicles. Microelectrode injury of HEK293 cells expressing RFP-MG53 (d) results in massive translocation of MG53 to the injury site (arrow) in less than 90 seconds. This result demonstrates that recombinant MG53 can be useful for repairing cellular and/or tissue damage in any cellular environment. Although recombinant MG53 is able to repair injury to cellular membranes when expressed in a heterologous system the invention is not so limited. In certain embodiments, the invention encompasses methods of co-expression of MG53 and caveolin-3 in order to promote membrane repair in order to treat or prevent tissue damage. In another embodiment, the present invention relates to a therapeutic composition comprising a TAT-MG53 polypeptide and a TAT-caveolin-3 polypeptide.

Figure 19:
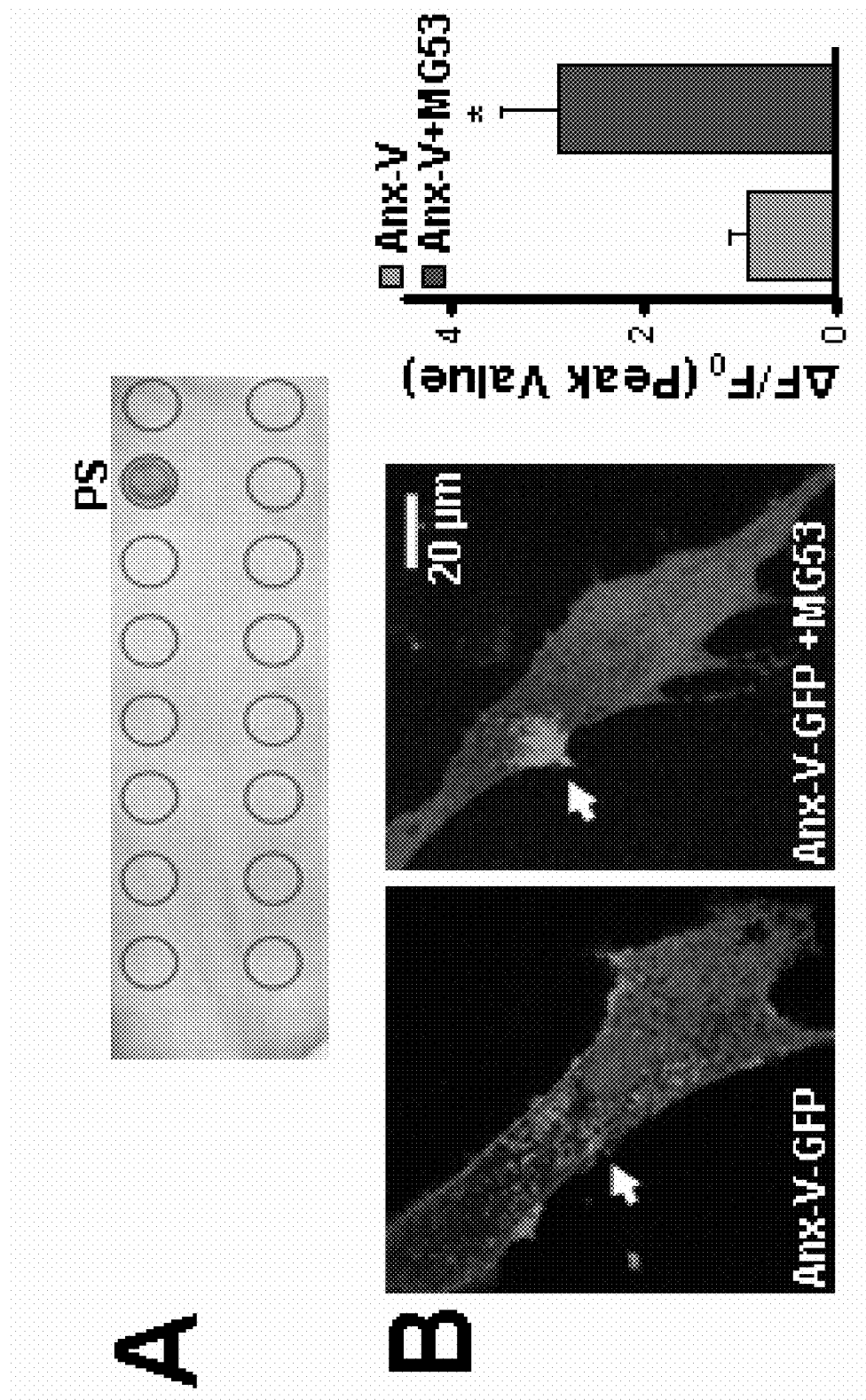
FIG. 19: MG53 interacts with cellular membranes through an association with phosphatidylserine to mediate vesicular trafficking. (A) PIP$_2$-Strip lipid dot blot analysis reveals recombinant MG53 (1 μg/ml) specifically binds phosphatidylserine (PS) and not other membrane lipids, including sphingosine-1-P, phosphatidic acid, phosphotidylcholine, phosphatidylethanolamine and various phosphainositol metabolites. (B) Annexin-V-GFP (a molecule with well defined ability to bind PS) transfected into C2C12 myoblasts (left) displays minimal translocation following cell wounding with a microelectrode (arrow), while co-expression of Annexin-V-GFP with RFP-MG53 (right) results in accelerated accumulation of Annexin-V-GFP. Data represent mean±s.e.m. (n=10). * p<0.01 by Student's t-test.
Figure 20:
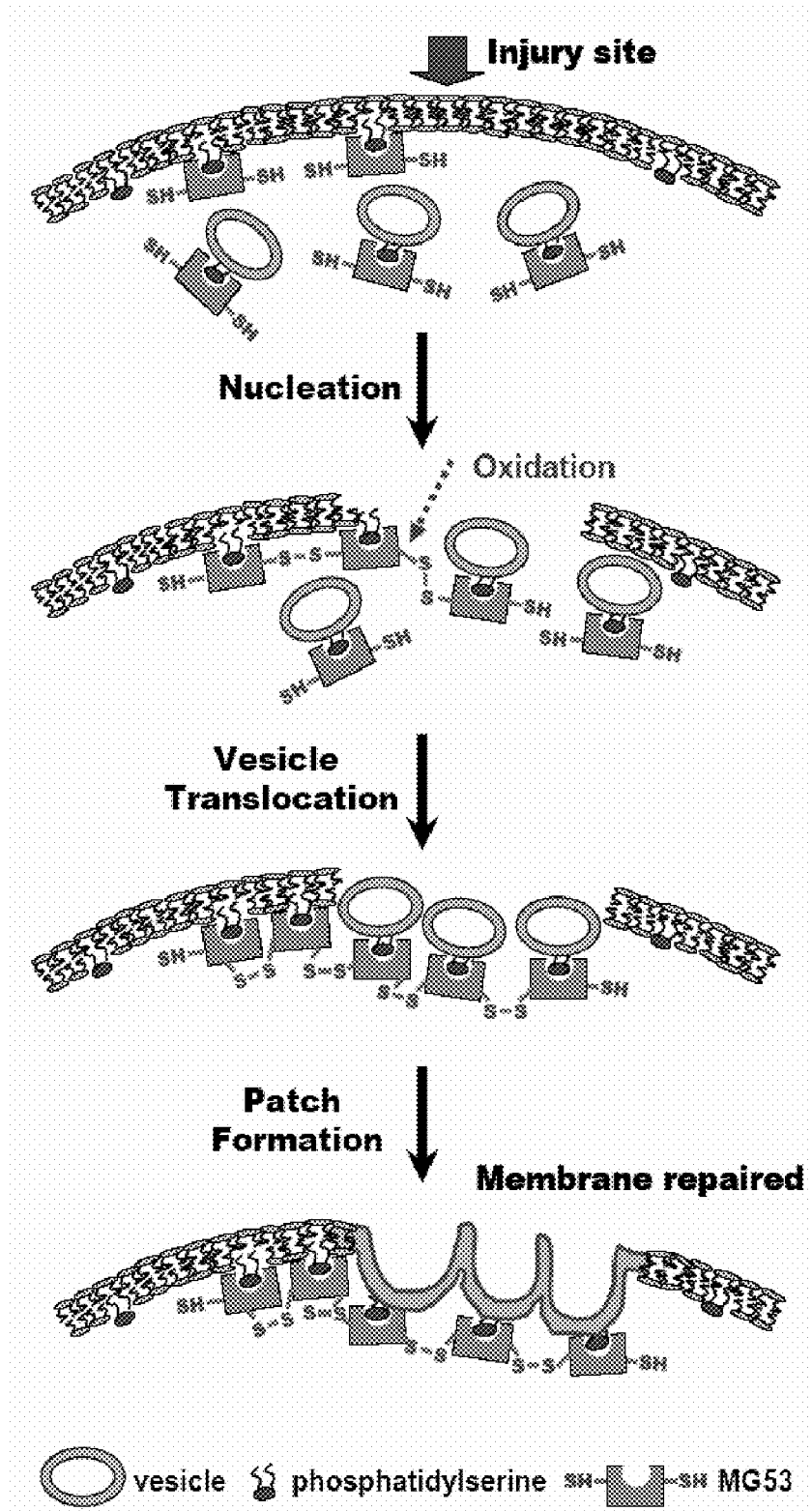
FIG. 20: Illustration demonstrating the inventors' current hypothesis on the mechanism of membrane repair mediated by MG53. While not being limited to any particular theory, experimental evidence indicates that MG53 is likely localized to the inner surface of the plasma membrane due to its association with phosphatidylserine-containing vesicles. Under normal conditions MG53 is likely monomeric and sequestered proximal to the membrane surface due to associations with caveolin-3. Following damage to the cellular membrane MG53, which is normally in its reduced form, is exposed to a localized oxidative environment which triggers the formation of disulfide cross-bridges and intermolecular MG53 oligomerization. The oligomerization of MG53 brings phosphatidylserine-containing vesicles together at the damage site. The lipid vesicles are then able to patch the damaged membrane—likely mediated by simple hydrophobic forces.

MG53 association with membranes and membrane repair depends on interaction with phosphatidylserine. Lipid profiling (FIG. 19) revealed that the purified recombinant MG53 could interact specifically with phosphatidylserine (PS), lipids that preferentially appear at the inner leaflet of the plasma membrane and the cytoplasmic face of intracellular vesicles (FIG. 19A). If this interaction allows MG53 to tether to intracellular membranes, then vesicular accumulation following membrane disruption could be monitored by the movement of Annexin-V, a protein known to interact with PS. Using Annexin-V-GFP, we observed rapid labeling of Annexin-V-GFP at the C2C12 myoblast injury site (FIG. 19B). The accumulation of Annexin-V-GFP was accelerated by co-expression of RFP-MG53, consistent with a role for MG53 in mediating the acute membrane repair process. Live cell imaging demonstrated coordinated movement of RFP-MG53 and Annexin-V-GFP toward the injury site.

Exemplary Methods

Identification and cloning of MG53—The preparation and screening of a mAb library for microsomal proteins of rabbit skeletal muscle were described previously(21). The preparation of mAb5259 (IgG1 subclass) and immunoaffinity purification was carried out as described previously(21). Purified MG53 was subjected to amino acid sequence analysis and all sequences determined were encoded in the rabbit MG53 cDNA (data not shown). Homology searches in the databases found mouse and human MG53 using the rabbit partial amino acid sequences. An exon region of the mouse MG53 gene was amplified from mouse genomic DNA, and rabbit and mouse skeletal muscle libraries were screened using the $^{32}$P-labeled exon fragment to yield full-length cDNAs.

Immunohistochemical and Immunostaining analysis—Immunochemical analyses using mAb5259 were carried out as described previously(21) Immunoelectron-microscopy using secondary antibody conjugated with 15 nm gold particles was conduced as described previously(17).

Cell culture—The C2C12 murine myoblast cell line used for all studies was purchased from the American Type Culture Collection (Manassas, Va.). Cells were grown in a humidified environment at 37° C. and 5% $CO_2$ in DMEM medium for C2C12 or Ham's F12 medium for CHO cells supplemented with 10% fetal bovine serum, 100 units/ml penicillin and 100 ug/ml streptomycin. In order to induce myotube differentiation, C2C12 myoblasts were grown to confluence and the medium was switched to DMEM containing 2% horse serum, penicillin (100 U/ml), streptomycin (100 μg/ml). For transient transfections, C2C12 myoblasts or CHO cells were plated at 70% confluence in glass-bottom dishes. After 24 hours, cells were transfected with plasmids described above using GeneJammer reagent (Stratagene). Cells were visualized by live cell confocal imaging at 24-48 hours after transfection or at times indicated for individual experiments. In some experiments, C2C12 myoblasts were allowed to differentiate into myotubes for the indicated time before observation.

Plasmids construction—The full-length mouse MG53 cDNA and associated truncation mutants were generated by PCR using the primers described in supplemental table 1. For construction of pCMS-MG53, after digestion by the appropriate restriction enzymes, the PCR-amplified cDNA was inserted into pCMS-EGFP vector (Invitrogen) at Nhe I/Xba I sites. For construct the GFP-MG53, GFP-TRIM, GFP-SPRY, MG53-GFP, TRIM-GFP and SPRY-GFP, PCR products were inserted into pEGFP-C1 at the XhoI/XbaI sites, or pEGFP-N1 at the XhoI/KpnI sites.

Live cell imaging—To monitor intracellular trafficking of GFP-MG53 either CHO or C2C12 cells were cultured in glass-bottom dishes (Bioptechs Inc.) and transfected with the plasmids described above. Fluorescence images (512×512) were captured at 3.18 s/frame using a BioRad 2100 Radiance laser scanning confocal microscope with a 63×1.3NA oil immersion objective.

RNAi assay—The target sequence for shRNA knockdown of MG53 is at position 622-642 (GAG CTG TCA AGC CTG AAC TCT) in the mouse MG53 cDNA. For caveolin-3, the target sequence is at position 363-380 (GAC ATT CAC TGC AAG GAG ATA). Complementary sense and antisense oligonucleotides were synthesized. To construct the MG53 shRNA and control plasmids, annealed oligonucleotides were inserted into psiRNA-hH1GFPzeo G2 (InvivoGene) at the Acc 65I/Hind III restriction enzyme sites. For caveolin-3 shRNA and control plasmids, annealed oligonucleotides were inserted into pRNAiDsRed vector (BD Biosciences) at the EcoR I/BamH I restriction enzyme sites. Each vector has as independent fluorescent protein expression cassette (green or red) to act as markers of cell transfection. All plasmids were confirmed by direct sequencing with flanking primers and the down-regulation of MG53 and caveolin-3 protein expression was examined by Western blot analysis.

Western blot and Co-immunoprecipitation—Immunoblots were using standard techniques. Briefly, C2C12 or CHO cells were harvested and lysed with ice-cold modified RIPA buffer (150 mM NaCl, 5 mM EDTA, 1% NP40, 20 mM Tris-HCl, pH 7.5) in the presence of a cocktail of protease inhibitors (Sigma). 20 μg of total protein were separated on a 4-12% SDS-polyacrylamide gel. A standard protocol was used for co-immunoprecipitation studies of MG53 and Caveolin-3. In brief, skeletal muscle tissue or C2C12 myotubes were lysed in 0.5 ml modified RIPA buffer. The whole cell lysate (500 μg) was incubated overnight with 5 μg polyclonal anti-MG53 (polyclonal antibody), or anti-caveolin-3 antibody (mAb). As a negative control, 500 μg whole cell lysate was incubated with 5 μg normal rabbit and mouse IgG and processed as described above. The immune complexes were collected on protein G-Sepharose beads by incubating for 2 hours and washed four times with RIPA buffer.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

The invention claimed is:

1. A composition comprising an effective amount of an MG53 polypeptide and a pharmaceutically acceptable excipient or carrier.

2. A method for the treatment or prevention of cellular damage comprising administering a therapeutically or prophylactically effective amount of the composition of claim 1.

3. The method of claim 2, wherein the method further comprises administering, contemporaneously, another polypeptide comprising SEQ ID NO. 8 or a portion thereof.

4. The method of claim 2, wherein the cellular damage is due to a cardiovascular disorder.

5. The method of claim 2, wherein the cellular damage is due to exercise or rigorous physical activity.

6. The method of claim 2, wherein the cellular damage is due to a surgical procedure or device.

7. A method of treating or preventing muscle cell damage comprising administering a therapeutically or prophylactically effective amount of the composition of claim 1.

8. The composition of claim 1, wherein the MG53 polypeptide is a polypeptide having at least 95% identity to at least one of SEQ ID NO. 1, 3, 5 or 7, wherein the peptide is effective for repairing cell membrane damage.

9. The composition of claim 1, wherein the MG53 polypeptide comprises a polypeptide as set forth in SEQ ID NO:1.

10. The composition of claim 1, wherein the MG53 polypeptide comprises a polypeptide as set forth in SEQ ID NO:3.

11. The composition of claim 1, wherein the MG53 polypeptide comprises a polypeptide as set forth in SEQ ID NO:5.

12. The composition of claim 1, wherein the MG53 polypeptide comprises a polypeptide as set forth in SEQ ID NO:7.

13. The composition of claim 8, wherein the MG53 polypeptide is joined covalently in a single, contiguous polypeptide chain with an additional polypeptide.

14. The composition of claim 13, wherein the additional polypeptide comprises at least one of a MG53 polypeptide, TAT polypeptide, RFP, GFP, FLAG tag, 6×His tag, maltose bind tag (MBP) or combination thereof.

15. The composition of claim 13, wherein an additional polypeptide is located at either of the amino terminus, the carboxyl terminus, or both, and wherein all of the polypeptides are joined covalently in a single, contiguous polypeptide chain.

16. An isolated MG53 polypeptide comprising an amino acid sequence having at least 95% sequence identity with at least one of SEQ ID NO.: 1, 3, 5, or 7, wherein the MG53 polypeptide is effective for promoting repair of a damaged cell membrane or resisting cell membrane damage.

17. A composition comprising the isolated MG53 polypeptide of claim 16, further comprising a pharmaceutically acceptable carrier.

18. A method for the treatment or prevention of cellular damage comprising administering a composition comprising a therapeutically or prophylactically effective amount of the composition of claim 1.

19. The method of claim 18, wherein the cellular damage comprises at least one of muscle cell damage, epithelial cell damage, fibroblast cell damage, stromal cell damage, kidney cell damage or a combination thereof.

20. The method of claim 19, wherein the muscle cell damage is skeletal muscle cell damage.

21. The method of claim 18, wherein the composition is administered topically.

22. The method of claim 18, wherein the composition is administered locally.

23. The method of claim 18, wherein the composition is administered systemically.

24. A method of treating or preventing muscle cell damage comprising administering a composition comprising a therapeutically or prophylactically effective amount of an MG53 polypeptide having at least 95% identity to SEQ ID NO. 1, 3, 5 or 7, and a pharmaceutically acceptable carrier, wherein the composition is effective for promoting repair of a damaged muscle cell membrane or resisting cell membrane damage.

25. A therapeutic composition comprising an effective amount of an MG53 polypeptide and a pharmaceutically acceptable excipient or carrier, wherein the composition is effective for promoting repair of a damaged cell membrane or resisting cell membrane damage.

* * * * *